United States Patent [19]

Mühlebach et al.

[11] Patent Number: 5,973,085
[45] Date of Patent: *Oct. 26, 1999

[54] MONOMERS AND COMPOSITION WHICH CAN BE CROSSLINKED AND CROSSLINKED POLYMERS

[75] Inventors: Andreas Mühlebach, Belfaux; Andreas Hafner, Laupen; Paul Adriaan Van Der Schaaf, Fribourg, all of Switzerland

[73] Assignee: Ciba Specialty Chemicals Corporation, Tarrytown, N.Y.

[ * ] Notice: This patent issued on a continued prosecution application filed under 37 CFR 1.53(d), and is subject to the twenty year patent term provisions of 35 U.S.C. 154(a)(2).

[21] Appl. No.: 08/836,461
[22] PCT Filed: Nov. 6, 1995
[86] PCT No.: PCT/EP95/04359
   § 371 Date: May 14, 1997
   § 102(e) Date: May 14, 1997
[87] PCT Pub. No.: WO96/16008
   PCT Pub. Date: May 30, 1996

[30] Foreign Application Priority Data

Nov. 17, 1994 [CH] Switzerland .............................. 3466/94

[51] Int. Cl.$^6$ ................................ C08F 4/80; C07C 13/61
[52] U.S. Cl. ........................... 526/171; 526/280; 526/281; 585/22; 585/361
[58] Field of Search ...................... 585/22, 361; 526/104, 526/283, 171, 280, 281

[56] References Cited

U.S. PATENT DOCUMENTS

| | | | |
|---|---|---|---|
| 3,187,018 | 6/1965 | Tinsley et al. | 260/348 |
| 4,203,930 | 5/1980 | Myers, Jr. | 585/22 |
| 4,426,502 | 1/1984 | Minchak et al. | 526/172 |
| 5,182,360 | 1/1993 | Jacobine et al. | 528/205 |
| 5,198,511 | 3/1993 | Brown-Wensley et al. | 526/113 |
| 5,296,566 | 3/1994 | Brown-Wensley et al. | 526/171 |

FOREIGN PATENT DOCUMENTS

0287762  10/1988  European Pat. Off. .

OTHER PUBLICATIONS

Journal of Chemical Engineering Data, vol. 9, No. 2, Apr. 1964, p. 240, Medved et al.

*Primary Examiner*—Michael Lewis
*Assistant Examiner*—Alexander G. Ghyka
*Attorney, Agent, or Firm*—Luther A. R. Hall; David R. Crichton; Victoria M. Malia

[57] ABSTRACT

Compounds of the formula I $$(A)_n-B \qquad (I)$$

in which A is the radical of a strained cycloolefin, B is a direct bond or an n-valent bridging group and n is an integer from 2 to 8, with the exception of 1,2-bisnorbornenyl-ethane and norbornenecarboxylic acid norbornenemethyl ester. The compounds of the formula I can be polymerized with one-component catalysts (ring-opening metathesis polymerization).

32 Claims, No Drawings

MONOMERS AND COMPOSITION WHICH CAN BE CROSSLINKED AND CROSSLINKED POLYMERS

The present invention relates to compounds having at least two strained cycloolefins bonded directly or via a bridging group; compositions comprising these compounds and a one-component catalyst for thermally induced and/or radiation-induced metathesis polymerization; a polymerization process, crosslinked polymers from the compounds mentioned and, if appropriate, other olefins and/or cycloolefins suitable for metathesis polymerization; carrier materials coated with these crosslinked polymers; and a polymerization process.

WO 93/13171 describes air- and water-stable one-component and two-component catalysts based on molybdenum compounds and tungsten compounds containing carbonyl groups and ruthenium compounds and osmium compounds with at least one polyene ligand for the thermal metathesis polymerization and a photoactivated metathesis polymerization of strained cycloolefins, in particular norbornene and norbornene derivatives. No other polycyclic— above all non-fused polycyclic cycloolefins are mentioned. The one-component catalysts of the ruthenium compounds used, that is to say $[(C_6H_6)\,Ru(CH_3CN)_2Cl]^+PF_6^-$ and $[Ru(cumene)Cl_2]_2$, can indeed be activated by UV irradiation; however, the storage stability of the compositions with norbornene are [sic] completely inadequate. These catalysts are capable of replacing the known two-component catalysts only inadequately.

Demonceau et al. [Demonceau, A., Noels A. F., Saive, E., Hubert, A. J., J. Mol. Catal. 76:123–132(1992)] describe $(C_6H_5)_3]_3PRuCl_2$ [sic], (p-cumene)$RuCl_2P(C_6H_{11})_3$ and $(C_6H_5)_3]_3PRuHCl$ [sic] as thermal catalysts for ring-opening metathesis polymerization of norbornene, a fused polycycloolefin. These catalysts have not found acceptance in industrial preparation because their activity is too low. It is therefore proposed to increase the activity by the addition of diazo esters. It is also mentioned that only (p-cumene) $RuCl_2P(C_6H_{11})_3$ is capable of polymerizing norbornene in a relatively short time at 60° C. Cyclooctene is also mentioned as a further monomer. No other cycloolefins for methatesis [sic] polymerization are mentioned.

Petasis and Fu [Petasis, N. A., Fu, D., J. Am. Chem. Soc. 115:7208–7214 (1993)] describe thermal ring-opening metathesis polymerization of norbornene using biscyclopentadienyl-bis(trimethylsilyl)methyl-titanium(IV) as a thermally active catalyst. No other cycloolefins for metathesis polymerization are mentioned. EP 287,762 describes crosslinked copolymers of a mixture of 1,2-bisnorbornenyl-ethane of the formula

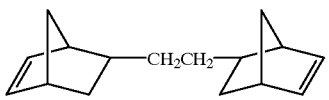

and a compound of the fromula [sic]

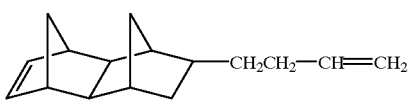

which are prepared using catalyst systems for thermal metathesis polymerization comprising a catalyst and an activator. A disadvantage of these systems is the need to separate the catalyst and activator, so that no storage-stable polymerizable compositions can be provided. The catalyst and activator can be combined only directly before the polymerization, highly reactive compositions which rapidly gel with evolution of heat being formed. The production of shaped articles is therefore limited to certain processes, such as, for example, the RIM process. The resulting crosslinked polymers have high softening temperatures. No coated materials are mentioned.

It has now been found that compositions of compounds comprising at least two strained cycloolefins bonded directly or via a bridge group and a one-component catalyst are storage-stable and have an outstanding processability, even in the presence of oxygen and moisture, depending on the choice of catalyst. These compositions can be processed by means of the most diverse shaping processes to give crosslinked metathesis polymers without special safety precautions. The polymers have high crosslinking densities and outstanding mechanical and electrical properties as well as surface properties, for example low ε values and tan δ values, and a very low absorption of water. The monomers used are outstanding film-forming agents and the polymer films have outstanding properties. It has furthermore been found that coatings in the form of crosslinked polymers which have exceptionally high adhesive strengths even on smooth metal surfaces are obtained with the compositions. The storage stability enables the use as coatings, paints, photoresists and adhesives and the production of all types of shaped articles. The preparation of rubber-like or thermoplastic polymers which can be crosslinked further is also possible.

The invention relates to compounds of the formula I $$(A)_n\text{—B} \qquad\qquad (I),$$

in which A is the radical of a strained cycloolefin, B is a direct bond or an n-valent bridging group and n is an integer from 2 to 8, with the exception of 1,2-bisnorbornenyl-ethane and norbornenecarboxylic acid norbornenemethyl ester.

The cyclic olefins can be monocyclic or polycyclic fused and/or bridged ring systems, for example with two to four rings, which are unsubstituted or substituted and can contain heteroatoms, such as, for example, O, S, N or Si, in one or more rings and/or fused alicyclic, aromatic or heteroaromatic rings, such as, for example, o-cyclopentylene, o-phenylene, o-naphthylene, o-pyridinylene or o-pyrimidinylene. The individual cyclic rings can contain 3 to 16, preferably 3 to 12, and particularly preferably 3 to 8 ring members. The cyclic olefins can contain other non-aromatic double bonds, preferably 2 to 4 such additional double bonds, depending on the ring size. The ring substituents are those which are inert, i.e. which do not impair the chemical stability of the one-component catalysts.

Fused-on alicyclic rings preferably contain 3 to 8, particularly preferably 4 to 7, and especially preferably 5 or 6 ring C atoms.

In a preferred embodiment, the radicals a in formula I correspond to cycloolefin radicals of the formula II

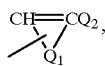 (II)

in which

Q₁ is a radical having at least one carbon atom which, together with the —CH═CQ₂ group, forms an at least 3-membered alicyclic ring which optionally contains one or more heteroatoms chosen from the group consisting of silicon, phosphorus, oxygen, nitrogen and sulfur; and which is unsubstituted or substituted by halogen, ═O, —CN, —NO₂, $R_1R_2R_3Si$—$(O)_u$—, —COOM, —SO₃M, —PO₃M, —$COO(M_1)_{1/2}$, —$SO_3(M_1)_{1/2}$, —$PO_3(M_1)_{1/2}$, $C_1$–$C_{20}$alkyl, $C_1$–$C_{20}$hydroxyalkyl, $C_1$–$C_{20}$haloalkyl, $C_1$–$C_6$cyanoalkyl, $C_3$–$C_8$cycloalkyl, $C_6$–$C_{16}$aryl, $C_7$–$C_{16}$aralkyl, $C_3$–$C_6$heterocycloalkyl, $C_3$–$C_{16}$heteroaryl, $C_4$–$C_{16}$heteroaralkyl or $R_4$-X-; or in which two adjacent C atoms are substituted by —CO—O—CO— or —CO—NR₅—CO—; or in which an aromatic or heteroaromatic ring and/or further alicyclic rings which is [sic] unsubstituted or substituted by halogen, —CN, —NO₂, $R_6R_7R_8Si$—$(O)_u$—, —COOM, —SO₃M, —PO₃M, —$COO(M_1)_{1/2}$, —$SO_3(M_1)_{1/2}$, —$PO_3(M_1)_{1/2}$, $C_1$–$C_{20}$alkyl, $C_1$–$C_{20}$haloalkyl, $C_1$–$C_{20}$hydroxyalkyl, $C_1$–$C_6$cyanoalkyl, $C_3$–$C_8$cycloalkyl, $C_6$–$C_{16}$aryl, $C_7$–$C_{16}$aralkyl, $C_3$–$C_6$heterocycloalkyl, $C_3$–$C_{16}$heteroaryl, $C_4$–$C_{16}$heteroaralkyl or $R_{13}$-$X_1$- are optionally fused onto adjacent carbon atoms of the alicyclic ring;

X and X₁ independently of one another are —O—, —S—, —CO—, —SO—, -SO₂—, —O—C(O)—, —C(O)—O—, —C(O)—NR₅—, —NR₁₀ —C(O)—, —SO₂—O— or —O—SO₂—;

R₁, R₂ and R₃ independently of one another are $C_1$–$C_{12}$alkyl, $C_1$–$C_{12}$perfluoroalkyl, phenyl or benzyl;

R₄ and R₁₃ independently are $C_1$–$C_{20}$alkyl, $C_1$–$C_{20}$haloalkyl, $C_1$–$C_{20}$hydroxyalkyl, $C_3$–$C_8$cycloalkyl, $C_6$–$C_{16}$aryl or $C_7$–$C_{16}$aralkyl;

R₅ and R₁₀ independently of one another are hydrogen, $C_1$–$C_{12}$alkyl, phenyl or benzyl, where the alkyl groups in turn are unsubstituted or substituted by $C_1$–$C_{12}$alkoxy or $C_3$–$C_8$cycloalkyl;

R₆, R₇ and R₈ independently of one another are $C_1$–$C_{12}$alkyl, $C_1$–$C_{12}$perfluoroalkyl, phenyl or benzyl;

M is an alkali metal and M₁ is an alkaline earth metal; and u is 0 or 1;

where the alicyclic ring formed with Q₁ optionally contains further non-aromatic double bonds;

Q₂ is hydrogen, $C_1$–$C_{20}$alkyl, $C_1$–$C_{20}$haloalkyl, $C_1$–$C_{12}$alkoxy, halogen, —CN or $R_{11}$-$X_2$;

R₁₁ is $C_1$–$C_{20}$alkyl, $C_1$–$C_{20}$haloalkyl, $C_1$–$C_{20}$hydroxyalkyl, $C_3$–$C_8$cycloalkyl, $C_6$–$C_{16}$aryl or $C_7$–$C_{16}$aralkyl;

X₂ is —C(O)—O— or —C(O)—NR₁₂—;

R₁₂ is hydrogen, $C_1$–$C_{12}$alkyl, phenyl or benzyl;

where the abovementioned cycloalkyl, heterocycloalkyl, aryl, heteroaryl, aralkyl and heteroaralkyl groups are unsubstituted or substituted by $C_1$–$C_{12}$alkyl, $C_1$–$C_{12}$alkoxy, —NO₂, —CN or halogen, and where the heteroatoms of the abovementioned heterocycloalkyl, heteroaryl and heteroaralkyl groups are chosen from the group consisting of —O—, —S—, —NR₉— and —N═; and R₉ is hydrogen, $C_1$–$C_{12}$alkyl, phenyl or benzyl.

The position of the double bond in the ring of the formula II in relation to the free bond essentially depends on the ring size and the preparation method for the compounds of the formula I.

If an asymmetric centre is present in the compounds of the formula II, the compounds can occur in optically isomeric forms as a result. Some compounds of the formula II can occur in tautomeric forms (for example keto-enol tautomerism). If an aliphatic C═C double bond is present, geometric isomerism (E form or Z form) can also occur. Exo-endo configurations are furthermore also possible. Formula II thus includes all the possible stereoisomers which are present in the form of enantiomers, tautomers, diastereomers, E/Z isomers or mixtures thereof.

In the definitions of the substituents, the alkyl, alkenyl and alkynyl groups can be straight-chain or branched. The same also applies to the alkyl moiety or each alkyl moiety of alkoxy, alkylthio, alkoxycarbonyl and further alkyl-containing groups. These alkyl groups preferably contain 1 to 12, more preferably 1 to 8, and particularly preferably 1 to 4 C atoms. These alkenyl and alkynyl groups preferably contain 2 to 12, more preferably 2 to 8, and particularly preferably 2 to 4 C atoms.

Alkyl includes, for example, methyl, ethyl, isopropyl, n-propyl, n-butyl, iso-butyl, sec-butyl, tert-butyl and the various isomeric pentyl, hexyl, heptyl, octyl, nonyl, decyl, undecyl, dodecyl, tridecyl, tetradecyl, pentadecyl, hexadecyl, heptadecyl, octadecyl, nonadecyl and eicosyl radicals.

Hydroxyalkyl includes, for example, hydroxymethyl, hydroxyethyl, 1-hydroxyisopropyl, 1-hydroxy-n-propyl, 2-hydroxy-n-butyl, 1-hydroxy-iso-butyl, 1-hydroxy-sec-butyl, 1-hydroxy-tert-butyl and the various isomeric pentyl, hexyl, heptyl, octyl, nonyl, decyl, undecyl, dodecyl, tridecyl, tetradecyl, pentadecyl, hexadecyl, heptadecyl, octadecyl, nonadecyl and eicosyl radicals.

Haloalkyl includes, for example, fluoromethyl, difluoromethyl, trifluoromethyl, chloromethyl, dichloromethyl, trichloromethyl, 2,2,2-trifluoroethyl, 2-fluoroethyl, 2-chloroethyl, 2,2,2-trichloroethyl and halogenated, in particular fluorinated or chlorinated, alkanes, such as, for example, the isopropyl, n-propyl, n-butyl, iso-butyl, sec-butyl and tert-butyl and the various isomeric pentyl, hexyl, heptyl, octyl, nonyl, decyl, undecyl, dodecyl, tridecyl, tetradecyl, pentadecyl, hexadecyl, heptadecyl, octadecyl, nonadecyl and eicosyl radicals.

Alkenyl includes, for example, propenyl, isopropenyl, 2-butenyl, 3-butenyl, isobutenyl, n-penta-2,4-dienyl, 3-methyl-but-2-enyl, n-oct-2-enyl, n-dodec-2-enyl, iso-dodecenyl, n-octadec-2-enyl and n-octadec-4-enyl.

Cycloalkyl is preferably $C_5$–$C_8$cycloalkyl, in particular $C_5$- or $C_6$cycloalkyl. Some examples are cyclopropyl, dimethylcyclopropyl, cyclobutyl, cyclopentyl, methylcyclopentyl, cyclohexyl, cycloheptyl and cyclooctyl.

Cyanoalkyl includes, for example, cyanomethyl (methylnitrile), cyanoethyl (ethylnitrile), 1-cyanoisopropyl, 1-cyano-n-propyl, 2-cyano-n-butyl, 1-cyano-iso-butyl, 1-cyano-sec-butyl, 1-cyano-tert-butyl and the various isomeric cyanopentyl and -hexyl radicals.

Aralkyl preferably contains 7 to 12 C atoms, and particularly preferably 7 to 10 C atoms. It can be, for example, benzyl, phenethyl, 3-phenylpropyl, α-methylbenzyl, phenbutyl or α,α-dimethylbenzyl.

Aryl preferably contains 6 to 10 C atoms. It can be, for example, phenyl, pentalin, indene, naphthalene, azulene or anthracene.

Heteroaryl preferably contains 4 or 5 C atoms and one or two heteroatoms from the group consisting of O, S and N. It can be, for example, pyrrole, furan, thiophene, oxazole, thiazole, pyridine, pyrazine, pyrimidine, pyridazine, indole, purine or quinoline.

Heterocycloalkyl preferably contains 4 or 5 C atoms and one or two heteroatoms from the group consisting of O, S and N. It can be, for example, oxirane, azirine, 1,2-oxathiolane, pyrazoline, pyrrolidine, piperidine, piperazine, morpholine, tetrahydrofuran or tetrahydrothiophene.

Alkoxy is, for example, methoxy, ethoxy, propyloxy, i-propyloxy, n-butyloxy, i-butyloxy, sec-butyloxy or t-butyloxy.

Alkali metal in the context of the present invention is to be understood as meaning lithium, sodium, potassium, rubidium and caesium, in particular lithium, sodium and potassium.

Alkaline earth metal in the context of the present invention is to be understood as meaning beryllium, magnesium, calcium, strontium and barium, in particular magnesium and calcium.

In the above definition, halogen is to be understood as meaning fluorine, chlorine, bromine and iodine, preferably fluorine, chlorine and bromine.

In the radicals of the formula II, $Q_2$ is preferably hydrogen.

Compounds with radicals of the formula II which are furthermore preferred are those in which the alicyclic ring which $Q_1$ forms together with the —CH=CQ$_2$— group has 3 to 16, more preferably 3 to 12, and particularly preferably 3 to 8 ring atoms, where the fused ring system can be monocyclic, bicyclic, tricyclic or tetracyclic.

The process according to the invention can be carried out particularly advantageously with those compounds with radicals of the formula II in which $Q_1$ is a radical with at least one carbon atom which, together with the —CH=CQ$_2$— group, forms a 3- to 20-membered alicyclic ring which optionally contains one or more heteroatoms chosen from the group consisting of silicon, oxygen, nitrogen and sulfur; and which is unsubstituted or substituted by halogen, =O, —CN, —NO$_2$, $R_1R_2R_3Si$—(O)$_u$—, —COOM, —SO$_3$M, —PO$_3$M, —COO(M$_1$)$_{1/2}$, —SO$_3$(M$_1$)$_{1/2}$, —PO$_3$(M$_1$)$_{1/2}$, $C_1$–$C_{12}$alkyl, $C_1$–$C_{12}$haloalkyl, $C_1$–$C_{12}$hydroxyalkyl, $C_1$–$C_4$cyanoalkyl, $C_3$–$C_6$cycloalkyl, $C_6$–$C_{12}$aryl, $C_7$–$C_{12}$aralkyl, $C_3$–$C_6$heterocycloalkyl, $C_3$–$C_{12}$heteroaryl, $C_4$–$C_{12}$heteroaralkyl or $R_4$-X-; or in which two adjacent C atoms in this radical $Q_1$ are substituted by —CO—O—CO— or —CO—NR$_5$—CO—; or in which an aromatic or heteroaromatic ring and/or further alicyclic rings which are unsubstituted or substituted by halogen, —CN, —NO$_2$, $R_6R_7R_8Si$—, —COOM, —SO$_3$M, —PO$_3$M, —COO(M$_1$)$_{1/2}$, —SO$_3$(M$_1$)$_{1/2}$, —PO$_3$(M$_1$)$_{1/2}$, $C_1$–$C_{12}$alkyl, $C_1$–$C_{12}$–haloalkyl, $C_1$–$C_4$cyanoalkyl, $C_3$–$C_6$cycloalkyl, $C_6$–$C_{12}$aryl, $C_7$–$C_{12}$aralkyl, $C_3$–$C_6$heterocycloalkyl, $C_3$–$C_{12}$heteroaryl, $C_4$–$C_{12}$heteroaralkyl or $R_{13}$-X$_1$- are optionally fused onto adjacent carbon atoms;

X and X$_1$ independently of one another are —O—, —S—, —CO—, —SO—, —SO$_2$—, —O—C(O)—, —C(O)—O—, —C(O)—NR$_5$—, —NR$_{10}$—C(O)—, —SO$_2$—O— or —O—SO$_2$—; and $R_1$, $R_2$ and $R_3$ independently of one another are $C_1$–$C_6$alkyl, $C_1$–$C_6$perfluoroalkyl, phenyl or benzyl;

M is an alkali metal and M$_1$ is an alkaline earth metal;

$R_4$ and $R_{13}$ independently of one another are $C_1$–$C_{12}$alkyl, $C_1$–$C_{12}$haloalkyl, $C_1$–$C_{12}$hydroxyalkyl, $C_3$–$C_8$cycloalkyl, $C_6$–$C_{12}$aryl or $C_7$–$C_{12}$aralkyl;

$R_5$ and $R_{10}$ independently of one another are hydrogen, $C_1$–$C_6$alkyl, phenyl or benzyl, where the alkyl groups in turn are unsubstituted or substituted by $C_1$–$C_6$alkoxy or $C_3$–$C_6$cycloalkyl;

$R_6$, $R_7$ and $R_8$ independently of one another are $C_1$–$C_6$alkyl, $C_1$–$C_6$perfluoroalkyl, phenyl or benzyl;

u is 0 or 1;

where the alicyclic ring formed with $Q_1$ optionally contains further non-aromatic double bonds;

$Q_2$ is hydrogen, $C_1$–$C_{12}$alkyl, $C_1$–$C_{12}$haloalkyl, $C_1$–$C_6$alkoxy, halogen, —CN or $R_{11}$-X$_2$-;

$R_{11}$ is $C_1$–$C_{12}$alkyl, $C_1$–$C_{12}$haloalkyl, $C_1$–$C_{12}$hydroxyalkyl, $C_3$–$C_6$cycloalkyl, $C_6$–$C_{12}$aryl or $C_7$–$C_{12}$aralkyl;

$X_2$ is —C(O)—O— or —C(O)—NR$_{12}$; and $R_{12}$ is hydrogen, $C_1$–$C_6$alkyl, phenyl or benzyl;

and where the cycloalkyl, heterocycloalkyl, aryl, heteroaryl, aralkyl and heteroaralkyl groups are unsubstituted or substituted by $C_1$–$C_6$alkyl, $C_1$–$C_6$alkoxy, —NO$_2$, —CN or halogen, and where the heteroatoms of the heterocycloalkyl, heteroaryl and heteroaralkyl groups are chosen from the group consisting of —O—, —S—, —NR$_9$- and —N=; and $R_9$ is hydrogen, $C_1$–$C_6$alkyl, phenyl or benzyl.

Preferred compounds with a radical of the formula II from this group are those in which $Q_1$ is a radical with at least one carbon atom which, together with the —CH=CQ$_2$- group, forms a 3- to 10-membered alicyclic ring which optionally contains a heteroatom chosen from the group consisting of silicon, oxygen, nitrogen and sulfur and is unsubstituted or substituted by halogen, —CN, —NO$_2$, $R_1R_2R_3Si$—, —COOM, —SO$_3$M, —PO$_3$M, —COO(M$_1$)$_{1/2}$, —SO$_3$(M$_1$)$_{1/2}$, —PO$_3$(M$_1$)$_{1/2}$, $C_1$–$C_6$alkyl, $C_1$–$C_6$haloalkyl, $C_1$–$C_6$hydroxyalkyl, $C_1$–$C_4$cycloalkyl, $C_3$–$C_6$cycloalkyl, phenyl, benzyl or $R_4$-X-; or in which an aromatic or heteroaromatic ring which is unsubstituted or substituted by halogen, —CN, —NO$_2$, $R_6R_7R_8Si$—, —COOM, —SO$_3$M, —PO$_3$M, —COO(M$_1$)$_{1/2}$, —SO$_3$(M$_1$)$_{1/2}$, —PO$_3$(M$_1$)$_{1/2}$, $C_1$–$C_6$alkyl, $C_1$–$C_6$haloalkyl, $C_1$–$C_6$hydroxyalkyl, $C_1$–$C_4$cyanoalkyl, $C_3$–$C_6$cycloalkyl, phenyl, benzyl or $R_{13}$-X$_1$- is optionally fused onto adjacent carbon atoms;

$R_1$, $R_2$ and $R_3$ independently of one another are $C_1$–$C_4$alkyl, $C_1$–$C_4$perfluoroalkyl, phenyl or benzyl;

M is an alkali metal and M$_1$ is an alkaline earth metal;

$R_4$ and $R_{13}$ independently of one another are $C_1$–$C_6$alkyl, $C_1$–$C_6$haloalkyl, $C_1$–$C_6$hydroxyalkyl or $C_3$–$C_6$cycloalkyl;

X and X$_1$ independently of one another are —O—, —S—, —CO—, —SO— or —SO$_2$—;

$R_6$, $R_7$ and $R_8$ independently of one another are $C_1$–$C_4$alkyl, $C_1$–$C_4$perfluoroalkyl, phenyl or benzyl; and $Q_2$ is hydrogen.

The cycloolefin radical of the formula II is particularly preferably unsubstituted or substituted cyclopropenyl, cyclobutenyl, cyclopentenyl, cycloheptenyl, cyclooctenyl, cyclopentadienyl, cyclohexadienyl, cycloheptadienyl, cyclooctadienyl and norbornenyl or norbornenyl derivatives, such as, for example, 7-oxa-2,2,2-cycloheptene, and the corresponding benzo derivatives. Substituents are preferably $C_1$–$C_4$alkyl and $C_1$–$C_4$alkoxy.

Particularly suitable radicals of the formula II are norbornenyl and norbornenyl derivatives. Particularly preferred compounds from these norbornenyl derivatives are those which correspond either to the formula III

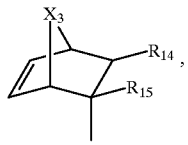

(III)

in which $X_3$ is —$CHR_{16}$—, oxygen or sulfur;

$R_{14}$ and $R_{15}$ independently of one another are hydrogen, —CN, trifluoromethyl, $(CH_3)_3Si$—O—, $(CH_3)_3Si$— or —$COOR_{17}$; and $R_{16}$ and $R_{17}$ independently of one another are hydrogen, $C_1$–$C_{12}$-alkyl, phenyl or benzyl; or to the formula IV

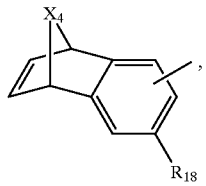

(IV)

in which $X_4$ is —$CHR_{19}$—, oxygen or sulfur;

$R_{19}$ is hydrogen, $C_1$–$C_{12}$alkyl, phenyl or benzyl; and $R_{18}$ is hydrogen, $C_1$–$C_6$alkyl or halogen.

The cycloolefin radical of the formula II is particularly preferably norbornenyl of the formula

In formula I, n is preferably an integer from 2 to 6, particularly preferably 2 to 4, and especially preferably 2 or 3.

In formula I, B is preferably an n-valent bridging group.

Possible divalent bridging groups are, for example, those of the formula V

$$—X_5—R_{20}—X_6—$$ (V), in which $X_5$ and $X_6$ independently of one another are a direct bond, —O—, —$CH_2$—O—, —C(O)O—, —O(O)C—, —$CH_2$—O(O)C—, —C(O)—$NR_{21}$—, —$R_{21}$N—(O)C—, —NH—C(O)—$NR_{21}$—, —O—C(O) —NH—, —$CH_2$—O—C(O)—NH— or —NH—C(O)—O— and $R_{20}$ is $C_2$–$C_{18}$alkylene, $C_5$–$C_8$cycloalkylene which is unsubstituted or substituted by $C_1$–$C_4$alkyl or $C_1$–$C_4$alkoxy, $C_6$–$C_{18}$arylene or $C_7$–$C_{19}$aralkylene which are unsubstituted or substituted by $C_1$–$C_4$alkyl or $C_1$–$C_4$alkoxy, or polyoxaalkylene having 2 to 12 oxaalkylene units and 2 to 6 C atoms in the alkylene, and $R_{21}$ is H or $C_1$–$C_6$alkyl.

Alkylene $R_{20}$ preferably contains 2 to 12, and particularly preferably 2 to 8 C atoms. The alkylene can be linear or branched. Preferred cycloalkylene is cyclopentylene, and in particular cyclohexylene. Some examples of arylene are phenylene, naphthylene, biphenylene, biphenylene ether and anthracenylene. An example of aralkylene is benzylene. The polyoxaalkylene preferably contains 2 to 6, and particularly preferably 2 to 4 units, and preferably 2 or 3 C atoms in the alkylene.

In a preferred embodiment, in formula V a) $X_5$ and $X_6$ are a direct bond and $R_{20}$ is $C_2$–$C_{18}$alkylene, preferably $C_2$–$C_{12}$alkylene, or b) $X_5$ and $X_6$ are —O—, —$CH_2$—O—, —C(O)O—, —O(O)C—, —$CH_2$—O(O)C—, —C(O)—$NR_{21}$—, —O—C(O)—NH— or —$CH_2$—O—C(O)—NH—, and $R_{20}$ is $C_2$—$C_{12}$alkylene, phenylene, naphthylene or benzylene which are unsubstituted or substituted by $C_1$–$C_4$alkyl or $C_1$–$C_4$alkoxy, or —$R_{22}$—(O—$R_{22}$—)$_x$ —$OR_{22}$—, in which x is a number from 2 to 4, and $R_{22}$ is —$C_2$–$C_4$alkylene.

Some examples of compounds of the formula I with a divalent bridging group are

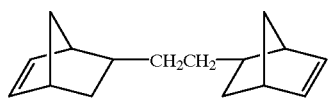

(0)

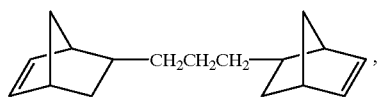

(1)

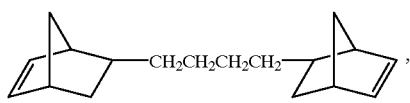 (2)
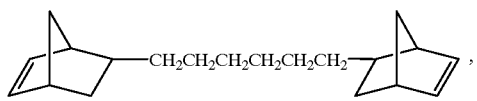 (3)
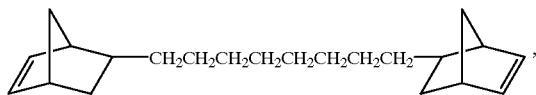 (4)
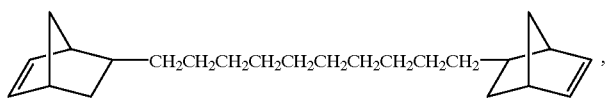 (5)
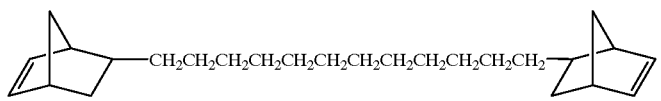 (6)
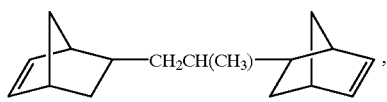 (7)
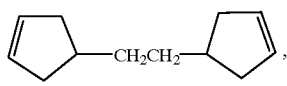 (8)
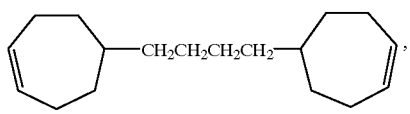 (9)
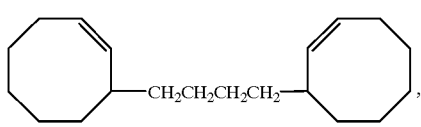 (10)
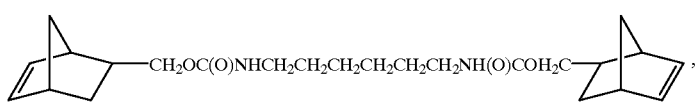 (11)
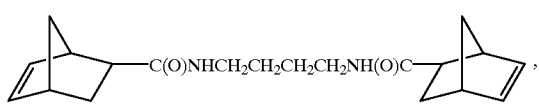 (12)
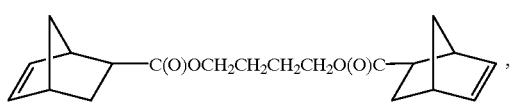 (13)

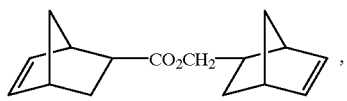 (13a)

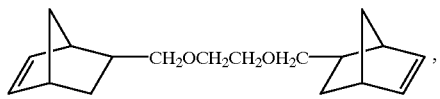 (14)

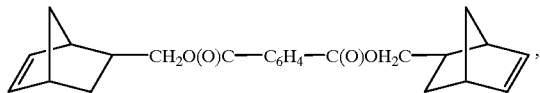 (15)

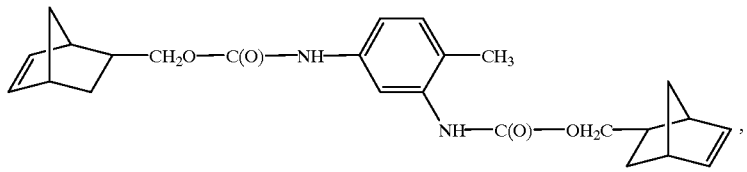 (16)

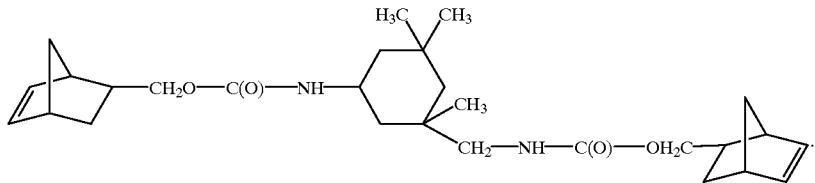 (17)

The compounds of the formula I with a bridging group of the formula V which is a pure hydrocarbon bridge are obtainable, for example, by means of Diels-Alder reaction of a cyclic diene with a linear or branched aliphatic diene (see also EP-A-0 287,762), substance mixtures which are either further used directly or separated beforehand by means of customary methods often being formed. Compounds of the formula I with a bridging group of the formula V in which $X_5$ and $X_6$ are not a direct bond are obtainable from the corresponding halides or dihalides, alcohols or diols, amines or diamines, carboxylic acids or dicarboxylic acids or isocyanates or diisocyanates in a manner known per se by etherification, esterification or amidation reactions.

Possible trivalent bridging groups are, for example, those of the formula VI

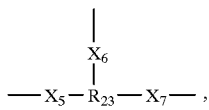 (VI)

in which $X_5$, $X_6$ and $X_7$ are —O—, —CH$_2$—O—, —C(O)O—, —O(O)C—, —CH$_2$—O(O)C—, —C(O)—NR$_{21}$—, —R$_{21}$N—(O)C—, —NH—C(O)—NR$_{21}$—, —O—C(O)—NH—, —CH$_2$—O—C(O)—NH— or —NH—C(O)—O—, and $R_{23}$ is a trivalent aliphatic hydrocarbon radical having 3 to 20, preferably 3 to 12, C atoms, a trivalent cycloaliphatic radical which has 3 to 8, preferably 5 or 6, ring C atoms and is unsubstituted or substituted by $C_1$–$C_4$alkyl or $C_1$–$C_4$alkoxy, or a trivalent aromatic radical which has 6 to 18, preferably 6 to 12, C atoms and is unsubstituted or substituted by $C_1$–$C_4$alkyl or $C_1$–$C_4$alkoxy, a trivalent araliphatic radical which has 7 to 19, preferably 7 to 12, C atoms and is unsubstituted or substituted by $C_1$–$C_4$alkyl or $C_1$–$C_4$alkoxy, or a trivalent heteroaromatic radical which has 3 to 13 C atoms and 1 to three heteroatoms from the group consisting of —O—, —N— and —S— and is unsubstituted or substituted by $C_1$–$C_4$alkyl or $C_1$–$C_4$alkoxy, and $R_{21}$ is H or $C_1$–$C_6$alkyl.

In a preferred embodiment, $X_5$, $X_6$ and $X_7$ are —O—, —CH$_2$—, —C(O)O—, —O(O)C—, —CH$_2$—O(O)C—, —C(O)—NR$_{21}$—, —O—C(O)—NH— or —CH$_2$—O—C(O)—NH—.

Preferred radicals $R_{23}$ are derived, for example, from triols, such as glycerol, trimethylolpropane, butanetriol, pentanetriol, hexanetriol, trihydroxycyclohexane, trihydroxybenzene and cyanuric acid; triamines, such as diethylenetriamine; tricarboxylic acids, such as cyclohexanetricarboxylic acid or trimellitic acid; and triisocyanates, such as benzene triisocyanate or cyanuric triisocyanate.

Some examples of compounds of the formula I with a trivalent bridging group are

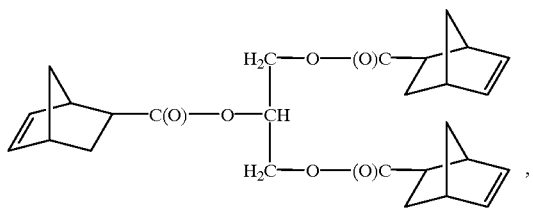
(18)

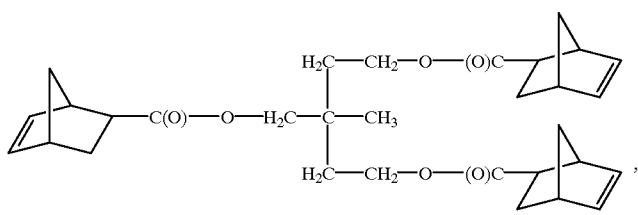
(19)

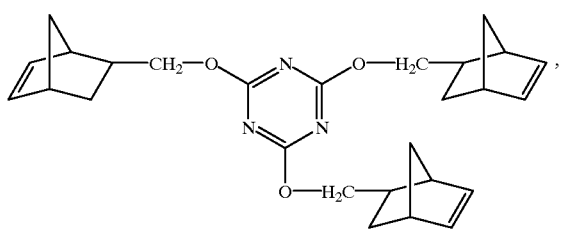
(20)

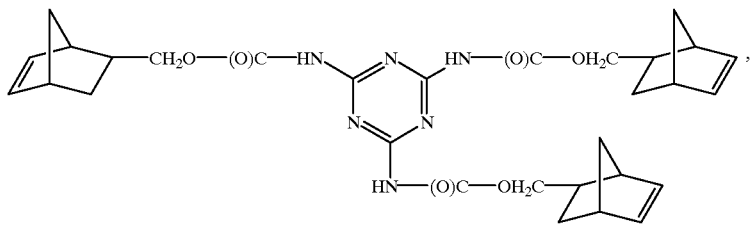
(21)

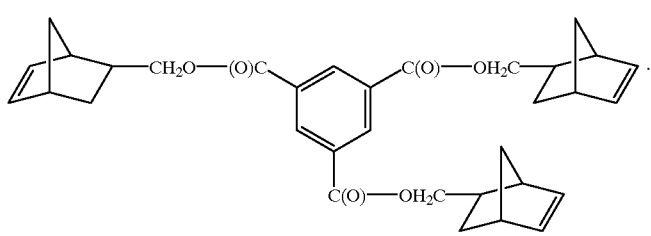
(22)

Possible tetravalent bridging groups are, for example, those of the formula VII

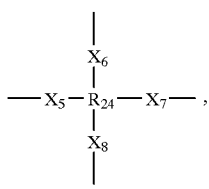
(VII)

in which $X_5$, $X_6$, $X_7$ and $X_8$ are —C(O)O—, —CH$_2$—O(O)C— or —C(O)—NR$_{21}$— and $R_{24}$ is a tetravalent aliphatic hydrocarbon radical having 4 to 20, preferably 4 to 12, C atoms, a tetravalent cycloaliphatic radical which has 4 to 8, preferably 5 or 6, ring C atoms and is unsubstituted or substituted by $C_1$–$C_4$alkyl or $C_1$–$C_4$alkoxy, or a tetravalent aromatic radical which has 6 to 18, preferably 6 to 12, C atoms and is unsubstituted or substituted by $C_1$–$C_4$alkyl or $C_1$–$C_4$alkoxy, a tetravalent araliphatic radical which has 7 to 19, preferably 7 to 12 C atoms and is unsubstituted or substituted by $C_1$–$C_4$alkyl or $C_1$–$C_4$alkoxy, or a tetravalent heteroaromatic radical which has 3 to 13 C atoms and 1 to three heteroatoms from the group consisting of —O—, —N— and —S— and is unsubstituted or substituted by $C_1$–$C_4$alkyl or $C_1$–$C_4$alkoxy, and $R_{21}$ is H or $C_1$–$C_6$alkyl.

Some examples of tetrafunctional compounds from which $R_{24}$ can be derived are pentaerythritol, pyromellitic acid and 3,4,3',4'-biphenyltetracarboxylic acid.

The same methods as for the preparation of the abovementioned compounds with a di- or trivalent radical can be used as the preparation methods.

Some examples of compounds of the formula I with a tetravalent bridging group are (23)

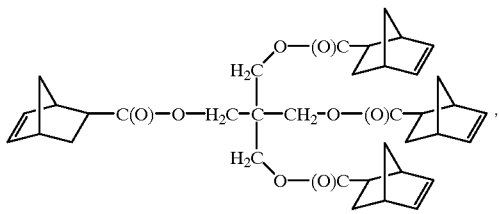

(24)

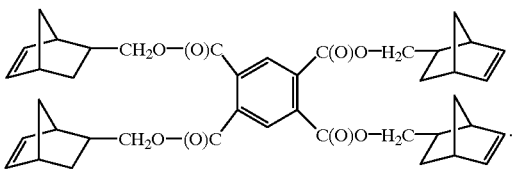

Polyols, such as dipentaerythritol or hexahydroxyhexane, which can be reacted with corresponding cycloolefinmonocarboxylic acids can be mentioned as an example of compounds which are more than tetravalent and from which the bridging group can be derived.

In a particularly preferred embodiment of the invention, the compounds of the formula I contain only carbon and hydrogen atoms, since the polymers of these are ecologically valuable inasmuch as they can be recycled by simple pyrolysis processes.

The compounds of the formula I are suitable as crosslinking agents in the thermally induced or radiation-induced polymerization of olefinically unsaturated compounds. The compounds of the formula I, by themselves or together with other monomers capable of metathesis polymerization, are outstandingly suitable for the preparation of crosslinked metathesis polymers using thermal or photochemical one-component catalysts.

The invention also relates to a composition of (a) at least one compound of the formula I $(A)_n$—B  (I), in which A is the radical of a strained cycloolefin, B is a direct bond or an n-valent bridging group and n is an integer from 2 to 8, and (b) a catalytic amount of at least one one-component catalyst for metathesis polymerization which can be activated by heat or radiction, with the exception of norbornenecarboxylic acid norbenenemethyl ester of the formula

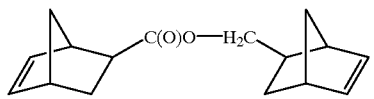

in combination with a catalytic amount of at least one heat-stable molybdenum(VI) or tungsten(VI) compound which contains, bonded to the metal, at least two methyl groups or two monosubstituted methyl groups, the substituent containing no hydrogen atom in the α position.

The abovementioned preferred meanings apply to A, B and n.

Heat stability in the context of the invention means that the photocatalytically active metal compounds form no active species for ring opening metathesis polymerization on heating. For example, the catalyst cannot initiate ring-opening metathesis polymerization at room temperature up to a slightly elevated temperature, such as about +40° C., within weeks with exclusion of light. During this period only an insignificant amount of monomer (less than 0.2% by weight) is reacted. The heat stability can be determined, for example, by storing a toluene solution with 20% by weight of monomer and 0.33% by weight of metal catalyst at 50° C. for 96 hours in the dark, and any amount of polymer formed, which is evident from the rise in viscosity and can be determined quantitatively by precipitation in a precipitant, for example ethanol, filtration and drying, is not more than 0.5% by weight and preferably not more than 0.2% by weight.

The compositions according to the invention advantageously comprise the following new thermal and/or photochemical one-component catalysts:

1. Heat-stable ruthenium or osmium compounds which can be activated by radiation and contain at least one photolabile ligand bonded to the ruthenium or osmium atom, and whose remaining coordination sites are satisfied by non-photolabile ligands.

Organic or inorganic compounds, atoms or ions which are coordinated onto a metal centre are designated as ligands for the ruthenium and osmium compounds to be used according to the invention.

Photolabile ligand in the context of the present invention means that, when the catalyst is irradiated by light in the visible or ultraviolet range of the spectrum, the ligand is dissociated from the catalyst and a catalytically active species for the metathesis polymerization is formed. Non-ionic photolabile ligands are preferred according to the invention.

The photolabile ligands can be, for example, nitrogen ($N_2$), monocyclic, polycyclic or fused arenes which have 6 to 24, preferably 6 to 18, and particularly preferably 6 to 12 C atoms and are unsubstituted or substituted by OH, $C_1$–$C_4$alkyl, $C_1$–$C_4$alkoxy, $C_6$–$C_{12}$aryl or halogen, or monocyclic heteroarenes, fused heteroarenes or fused arene-heteroarenes which have 3 to 22, preferably 4 to 16, and in particular 4 to 10 C atoms and 1 to 3 heteroatoms chosen from the group consisting of O, S and N and are unsubstituted or substituted by $C_1$–$C_4$alkyl, $C_1$–$C_4$alkoxy or halogen; or aliphatic, cycloaliphatic, aromatic or araliphatic nitriles which have 1 to 22, preferably 1 to 18, particularly preferably 1 to 12, and especially preferably 1 to 7 C atoms and are unsubstituted or substituted by $C_1$–$C_4$alkyl, $C_1$–$C_4$alkoxy or halogen. The preferred substituents are methyl, ethyl, methoxy, ethoxy, fluorine, chlorine and bromine. The arenes and heteroarenes are preferably substituted by one or two radicals and particularly preferably are unsubstituted. Preferred heteroarenes are the electron-rich heteroarenes. The arenes and heteroarenes can be both π- and σ-bonded; in the latter case, they are then the corresponding aryl and heteroaryl radicals. The aryl preferably contains 6 to 18, particularly preferably 6 to 12 C atoms. The heteroaryl preferably contains 4 to 16 C atoms.

Some examples of arenes and heteroarenes are benzene, p-cumene, biphenyl, naphthalene, anthracene, acenaphthene, fluorene, phenanthrene, pyrene, chrysene, fluoranthrene, furan, thiophene, pyrrole, pyridine, γ-pyran, γ-thiopyran, pyrimidine, pyrazine, indole, coumarone, thionaphthene, carbazole, dibenzofuran, dibenzothiophene, pyrazole, imidazole, benzimidazole, oxazole, thiazole, isoxazole, isothiazole, quinoline, isoquinoline, acridine, chromene, phenazine, phenoxazine, phenothiazine, triazine, thianthrene and purine. Preferred arenes and heteroarenes are benzene, naphthalene, thiophene and benzothiophene. The arene is especially preferably benzene, and the heteroarene is especially preferably thiophene.

The nitriles can be substituted, for example by methoxy, ethoxy, fluorine or chlorine; the nitriles are preferably unsubstituted. The alkylnitriles are preferably linear. Some examples of nitriles are acetonitrile, propionitrile, butyronitrile, pentylnitrile, hexylnitrile, cyclopentyl- and cyclohexylnitrile, benzonitrile, methylbenzonitrile, benzylnitrile and naphthyinitrile. The nitriles are preferably linear $C_1$–$C_4$alkylnitriles or benzonitrile. Of the alkylnitriles, acetonitrile is particularly preferred.

In a preferred subgroup, the photolabile ligands are $N_2$, or benzene, thiophene, benzonitrile or acetonitrile which are unsubstituted or substituted by one to three $C_1$–$C_4$alkyl.

Non-photolabile ligand (also called highly coordinating ligand) in the context of the present invention means that the ligand does not dissociate, or dissociates to only an insignificant extent, from the catalyst on irradiation of the catalyst in the visible or near ultraviolet range of the spectrum.

The non-photolabile ligands can be, for example, solvating inorganic and organic compounds which contain the heteroatoms O, S or N and are often also used as solvents, or cyclopentadienyl or indenyl which are unsubstituted or substituted by $C_1$–$C_4$alkyl, $C_1$–$C_4$alkoxy, $(C_1$–$C_4$alkyl$)_3$Si or $(C_1$–$C_4$alkyl$)_3$SiO—. Examples of such compounds are $H_2O$, $H_2S$, $NH_3$; optionally halogenated, in particular fluorinated or chlorinated, aliphatic or cycloaliphatic alcohols or mercaptans having 1 to 18, preferably 1 to 12, and particularly preferably 1 to 6 C atoms, aromatic alcohols or thiols having 6 to 18, preferably 6 to 12 C atoms, araliphatic alcohols or thiols having 7 to 18, preferably 7 to 12 C atoms; aliphatic, cycloaliphatic, araliphatic or aromatic ethers, thioethers, sulfoxides, sulfones, ketones, aldehydes, carboxylic acid esters, lactones, optionally N-$C_1$–$C_4$mono- or -dialkylated carboxylic acid amides having 2 to 20, preferably 2 to 12, and in particular 2 to 6 C atoms, and optionally N-$C_1$–$C_4$alkylated lactams; aliphatic, cycloaliphatic, araliphatic or aromatic primary, secondary and tertiary amines having 1 to 20, preferably 1 to 12, and particularly preferably 1 to 6 C atoms; and optionally cyclopentadienyls, such as, for example, cyclopentadienyl, indenyl and mono- or polymethylated or trimethylsilylated cyclopentadienyls or indenyls.

Examples of such non-photolabile ligands are methanol, ethanol, n- and i-propanol, n-, i- and t-butanol, 1,1,1-trifluoroethanol, bistrifluoromethylmethanol, tristrifluoromethylmethanol, pentanol, hexanol, methyl- or ethylmercaptan, cyclopentanol, cyclohexanol, cyclohexylmercaptan, phenol, methylphenol, fluorophenol, phenylmercaptan, benzylmercaptan, benzyl alcohol, diethyl ether, dimethyl ether, diisopropyl ether, di-n- or di-t-butyl ether, tetrahydrofuran, tetrahydropyran, dioxane, diethyl thioether, tetrahydrothiophene, dimethyl sulfoxide, diethyl sulfoxide, tetra- and pentamethylene sulfoxide, dimethyl sulfone, diethyl sulfone, tetra- and pentamethylene sulfone, acetone, methyl ethyl ketone, diethyl ketone, phenyl methyl ketone, methyl isobutyl ketone, benzyl methyl ketone, acetaldehyde, propionaldehyde, trifluoroacetaldehyde, benzaldehyde, ethyl acetate, butyrolactone, dimethylformamide, dimethylacetamide, pyrrolidone and N-methylpyrrolidone, indenyl, cyclopentadienyl, methyl- or dimethyl- or pentamethylcyclopentadienyl and trimethylsilylcyclopentadienyl.

The primary amines can correspond to the formula $R_{25}NH_2$, the secondary amines can correspond to the formula $R_{25}R_{26}NH$ and the tertiary amines can correspond to the formula $R_{25}R_{26}R_{27}N$ in which $R_{25}$ is $C_1$–$C_{18}$alkyl, $C_5$- or $C_6$cycloalkyl which is unsubstituted or substituted by $C_1$–$C_4$alkyl or $C_1$–$C_4$alkoxy, or $C_6$–$C_{18}$aryl or $C_7$–$C_{12}$aralkyl which are unsubstituted or substituted by $C_1$–$C_4$alkyl or $C_1$–$C_4$alkoxy, $R_{26}$ independently has the meaning of $R_{25}$, or $R_{25}$ and $R_{26}$ together are tetramethylene, pentamethylene, 3-oxa-1,5-pentylene or —$CH_2$—$CH_2$—NH—$CH_2$—$CH_2$— or —$CH_2$—$CH_2$—N($C_1$–$C_4$alkyl)—$CH_2$—$CH_2$—, $R_{25}$ and $R_{26}$ independently of one another are as defined above [sic] and $R_{27}$ independently has the meaning of $R_{25}$. The alkyl preferably contains 1 to 12, and particularly preferably 1 to 6 C atoms. The aryl preferably contains 6 to 12 C atoms and the aralkyl preferably contains 7 to 9 C atoms. Examples of amines are methyl-, dimethyl-, trimethyl-, ethyl-, diethyl-, triethyl-, methyl-ethyl-, dimethyl-ethyl-, n-propyl-, di-n-propyl-, tri-n-butyl-, cyclohexyl-, phenyl- and benzylamine, and pyrrolidine, N-methylpyrrolidine, piperidine, piperazine, morpholine and N-methylmorpholine.

In a preferred subgroup, the non-photolabile ligands are $H_2O$, $NH_3$ and $C_1$–$C_4$alkanols which are unsubstituted or partly or completely fluorinated. $H_2O$, $NH_3$, cyclopentadienyl, methanol and ethanol are especially preferred.

The ruthenium and osmium compounds to be used according to the invention can be mono- or polynuclear, for example those with two or metal centres. The metal atoms here can be bonded via a bridging group or metal-metal bonds. Preferred compounds with several metal centres are those of the formula VIII

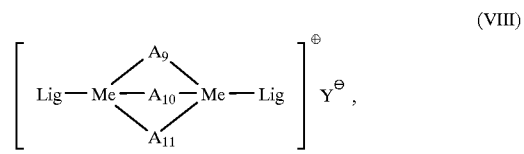

in which Lig is a photolabile ligand and Me is Ru or Os, $A_9$, $A_{10}$ and $A_{11}$ are a bivalent bridging group, and $Y^{\ominus}$ is a monovalent non-coordinating anion. The bridging group is preferably ionic and particularly preferably a halide, especially preferably chloride, bromide or iodide. The photolabile ligand is preferably identical or different arenes and $Y^{\ominus}$ can be the anions listed below, and especially chloride, bromide or iodide. One example of such complexes is $[C_6H_6Ru(Cl)_3RuC_6H_6]Cl$.

Preferred catalysts according to the invention correspond to the formula IX

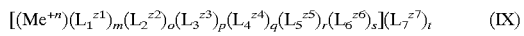

in which

Me is ruthenium or osmium;

n is 0, 1,2,3,4,5,6,7 or 8;

$L_1$ is a photolabile ligand;

$L_2$, $L_3$, $L_4$, $L_5$ and $L_6$ independently of one another are a non-photolabile or a photolabile ligand;

m is 1, 2, 3, 4, 5, or 6;

o, p, q, r, and s independently of one another are 0, 1, 2, 3, 4 or 5;

$z_1, z_2, z_3, Z_4, z_5, z_6$ and $z_7$ independently of one another are −4, −3, −2, −1,0, +1 or +2; and $L_7$ is a non-coordinating cation or anion;

the sum of m+o+p+q+r+s being an integer from 2 to 6 and t being the quotient of $(n+m \cdot z_1 + o \cdot z_2 + p \cdot z_3 + q \cdot z_4 + r \cdot z_5 + s \cdot z_6)/z_7$.

In the formula IX, $L_7$ is preferably halogen (for example Cl, Br and I), the anion of an oxygen acid, $BF_4$, $PF_6$, $SiF_6$ or $AsF_6$.

The anions of oxygen acids can be, for example, sulfate, phosphate, perchlorate, perbromate, periodate, antimonate, arsenate, nitrate, carbonate, the anion of a $C_1$–$C_8$carboxylic acid, such as, for example, formate, acetate, propionate, butyrate, benzoate, phenylacetate or mono-, di- or trichloro- or -fluoroacetate, sulfonates, such as, for example, methylsulfonate, ethylsulfonate, propylsulfonate, butylsulfonate, trifluoromethylsulfonate (triflate) or phenylsulfonate or benzylsulfonate which are optionally substituted by $C_1$–$C_4$alkyl, $C_1$–$C_4$alkoxy or halogen, in particular fluorine, chlorine or bromine, such as, for example, tosylate, mesylate, brosylate, p-methoxy- or p-ethoxyphenylsulfonate, pentafluorophenylsulfonate or 2,4,6-triisopropylsulfonate, and phosphonates, such as, for example, methylphosphonate, ethylphosphonate, propylphosphonate, butylphosphonate, phenylphosphonate, p-methylphenylphosphonate or benzylphosphonate.

In formula IX, Me is preferably ruthenium, in particular $Ru^{2+}$.

A group of compounds of the formula IX which is to be singled out in particular is that in which the ligands $L_1$, $L_2$, $L_3$, $L_4$, $L_5$ and $L_6$ independently of one another are aliphatic, cycloaliphatic, aromatic or araliphatic nitriles which have 1 to 22 C atoms and are unsubstituted or substituted by $C_1$–$C_4$alkyl, $C_1$–$C_4$alkoxy or halogen, or $C_6$–$C_{18}$aryl; or $L_1$, $L_2$ and $L_3$ together are monocyclic, polycyclic or fused arenes which have 6 to 24, preferably 6 to 18, and particularly preferably 6 to 12 C atoms and are unsubstituted or substituted by —OH, $C_1$–$C_4$alkyl, $C_1$–$C_4$alkoxy, $C_6$–$C_{12}$aryl or halogen, or monocyclic heteroarenes, fused heteroarenes or fused arene-heteroarenes which have 4 to 22 C atoms and 1 to 3 heteroatoms chosen from the group consisting of O, S and N and are unsubstituted or substituted by —OH, $C_1$–$C_4$alkyl, $C_1$–$C_4$alkoxy or halogen, and $L_4$, $L_5$ and $L_6$ together have the same meaning, or individually independently of one another are $N_2$ or the said nitrile or the said $C_6$–$C_{18}$aryl.

A preferred subgroup of the above compounds of the formula IX are those in which the ligands $L_1$, $L_2$, $L_3$, $L_4$, $L_5$ and $L_6$ independently of one another are $N_2$, $C_1$–$C_{20}$alkylnitrile $C_6$–$C_{12}$aryinitrile, $C_7$–$C_{12}$aralkylnitrile or $C_6$–$C_{12}$aryl, or $L_1$, $L_2$ and $L_3$ in each case to the groups $A_1$ or $A_2$

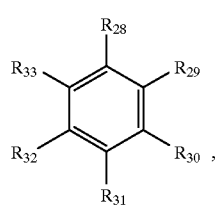

(A₁)

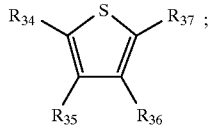

(A₂)

in which $R_{28}$, $R_{29}$, $R_{30}$, $R_{31}$, $R_{32}$, $R_{33}$, $R_{34}$, $R_{35}$, $R_{36}$ and $R_{37}$ independently of one hydrogen, $C_1$–$C_{20}$alkyl, $C_1$–$C_{20}$alkoxy, aryl or $SiR_{38}R_{39}R_{40}$, where, in the groups $A_1$ and $A_2$, aromatic or heteroaromatic ring, the heteroatoms of which are chosen from oxygen, sulfur and nitrogen, can be fused onto adjacent carbon atoms; and $R_{38}$, $R_{39}$ and $R_{40}$ independently of one another are $C_1$–$C_{12}$alkyl, $C_5$- or $C_6$-cycloalkyl, or phenyl or benzyl which are unsubstituted or substituted by $C_1$–$C_6$alkyl or $C_1$–$C_6$alkoxy, preferably $C_1$–$C_8$alkyl, phenyl or benzyl, particularly preferably $C_1$–$C_4$alkyl, phenyl or benzyl, and $L_4$, $L_5$ and $L_6$ likewise together have this meaning, or each individually are $N_2$, the said nitriles or the said $C_6$–$C_{12}$aryl, or an arene or heteroarene.

From this group of compounds of the formula IX which are to be singled out, preferred compounds are those in which $L_1$, $L_2$, $L_3$, $L_4$, $L_5$ and $L_6$ independently of one another are $C_1$–$C_{12}$alkylnitrile or $C_6$–$C_{12}$aryinitrile, or $L_1$, $L_2$ and $L_3$ in each case together are the groups $A_1$ or $A_2$ and $L_4$, $L_5$ and $L_6$ likewise together have this meaning or in each case individually are $N_2$, the said nitriles or the said arene or heteroarene of the formulae $A_1$ and $A_2$, in which $R_{28}$, $R_{29}$, $R_{30}$, $R_{31}$, $R_{32}$, $R_{33}$, $R_{34}$, $R_{35}$, $R_{36}$ and $R_{37}$ independently of one another are hydrogen, $C_1$–$C_6$alkyl, $C_1$–$C_6$alkoxy, $SiR_{38}R_{39}R_{40}$ or phenyl, where, in the groups $A_1$ and $A_2$, a benzene ring can be fused onto adjacent carbon atoms, and $R_{38}$, $R_{39}$ and $R_{40}$ are methyl, ethyl or phenyl.

In an especially preferred embodiment of the process according to the invention, the catalyst used corresponds to the formula IX in which $L_1$, $L_2$, $L_3$, $L_4$, $L_5$ and $L_6$ independently of one another are methylnitrile, ethylnitrile or phenylnitrile, or $L_1$, $L_2$ and $L_3$ in each case together are the groups $A_1$ or $A_2$ and $L_4$, $L_5$ and $L_6$ likewise together have this meaning or in each case individually are the said nitriles, in which $R_{28}$, $R_{29}$, $R_{30}$, $R_{31}$, $R_{32}$, $R_{33}$, $R_{34}$, $R_{35}$, $R_{36}$ and $R_{37}$ independently hydrogen, methyl, methoxy or phenyl where, in the groups $A_1$ and $A_2$, a benzene ring can be fused onto adjacent carbon atoms.

Another particularly preferred subgroup of the compounds of the formula IX are those in which $L_1$, $L_2$ and $L_3$ together are monocyclic, polycyclic or fused arenes which have 6 to 24, preferably 6 to 18, and particularly preferably 6 to 12 C atoms and are unsubstituted or substituted by $C_1$–$C_4$alkyl, $C_1$–$C_4$alkoxy, $C_6$–$C_{12}$aryl or halogen, or monocyclic heteroarenes, fused heteroarenes or fused arene-heteroarenes which have 4 to 22, preferably 4 to 16, and particularly 4 to 10 C atoms and 1 to 3 heteroatoms chosen from the group consisting of O, S and N and are unsubstituted or substituted by $C_1$–$C_4$alkyl, $C_1$–$C_4$alkoxy or halogen, and $L_4$, $L_5$ and $L_6$ are a non-photolabile ligand, the previous preferred meanings also applying here.

In this subgroup, $L_1$, $L_2$ and $L_3$ are preferably benzene or naphthalene, and the non-photolabile ligand is preferably $H_2O$, $NH_3$, $C_1$–$C_4$alkanol or -alkanethiol which is unsubstituted or substituted by fluorine, aliphatic ethers, thioethers, sulfoxides and sulfones having 2 to 8 C atoms, dimethylformamide or N-methylpyrrolidone.

In another preferred subgroup of compounds of the formula X, the compounds are ruthenium and osmium compounds of the formula X

in which $L_1$ is a photolabile ligand and $L_8$ is a non-photolabile ligand, Me is Ru or Os, $Y_1$ is a non-coordinating anion and x is the numbers 1, 2 or 3. For the photolabile ligands, non-photolabile ligands, Me and $Y_1$, the abovementioned preferred meanings apply. Particularly preferably, $L_1$ is $N_2$ or a nitrile, such as, for example, $C_1$–$C_4$alkylnitrile (acetonitrile), benzonitrile or benzylnitrile, $L_8$ is $NH_3$ or an amine having 1 to 12 C atoms, $Y_1$ is a non-coordinating anion and x is the number 1 or 2.

Catalysts which are particularly suitable for the present invention are (tos is tosylate and tis is 2,4,6-triisopropylphenylsulfonate): $Ru(CH_3CN)_6(tos)_2$, $Ru(CH_3CH_2CN)_6(tos)_2$, $Ru(CH_3CN)_6(CF_3SO_3)_2$, $Ru(CH_3CH_2CN)_6(CF_3SO_3)_2$, $Ru(C_6H_6)_2(tos)_2$, $[Ru(C_6H_6)(C_6H_5OCH_3)](BF_4)_2$, $[Ru(C_6H_6)(C_6H_5i\text{-propyl})](BF_4)_2$, $[Ru(C_6H_6)(1,3,5\text{-trimethylphenol})](BF_4)_2$, $[Ru(C_6H_6)(hexamethylbenzene)](BF_4)_2$, $[Ru(C_6H_6)(biphenyl)](BF_4)_2$, $[Ru(C_6H_6)(chrysene)](BF_4)_2$, $[Ru(C_6H_6)(naphthalene)](BF_4)_2$, $[Ru(cyclopentadienyl)(4\text{-methylcumyl})]PF_6$, $[Ru(cyanophenyl)_6](tos)_2$, $[Ru(cyanophenyl)_6](CF_3SO_3)_2$, $[Ru(C_6H_6)(tetramethylthiophene)_3](tos)_2$, $[Ru(C_6H_6)(CH_3CN)_3](tos)_2$, $[Ru(C_6H_6)(tetramethylthiophene)_3](CF_3SO_3)_2$, $[Ru(C_6H_6)(CH_3CN)3](CF_3SO_3)_2$, $[Ru(C_6H_6)(CH_3OH)_3](tos)_2$, $[Ru(C_6H_6)(CH_3OH)_3](tis)_2$, $[Os(NH_3)_5N_2](PF_6)_2$, $[Ru(NH_3)_5N_2](PF_6)_2$, $[Ru(NH_3)_5(CH_3CN)]BF_4$, $[Ru(C_6H_6(NH_3)_3](tis)_2$, $[Ru(C_6H_6(tetrahydrothiophene)_3](CF_3SO_3)_2$, $[Ru((CH_3)_2S)_3C_6H_6](tos)_2$, $[Ru(dimethyl sulfoxide)_3C_6H_6](PF_6)_2$, $[Ru(dimethylformamide)_3C_6H_6](PF_6)_2$, $[Ru(C_6H_6)Cl_2]_2$ and $[Os(C_6H_6)Cl_2]_2$.

Ruthenium and osmium catalysts to be used according to the invention are either known and in some cases commercially obtainable, or can be prepared analogously to known processes. Such catalysts and their preparation are described, for example, in Gilkerson, W. R., Jackson, M. D., J. Am. Chem. Soc. 101:4096–411 (1979), Bennett, M. A., Matheson, T. W., J. Organomet. Chem. 175:87–93 (1979), Moorehouse, S., Wilkinson, G., J. Chem. Soc.; Dalton Trans., 2187–2190 (1974) and Luo, S., Rauchfuss, T. B., Wilson, S. R., J. Am. Chem. Soc. 114:8515–8520 (1992).

2. Heat-stable molybdenum(VI) or tungsten(VI) compounds which can be activated thermally or with radiation and contain, bonded to the metal, at least two methyl groups or two monosubstituted methyl groups, the substituent containing no hydrogen atom in the α position.

The other valencies of the molybdenum and tungsten are preferably satisfied by heat-stable neutral ligands, a large number of which are known. The number of neutral ligands can exceed the stoichiometrically possible number (solvates). Heat stability has been explained above. At temperatures above 50° C., for example 60 to 300° C., these molybdenum and tungsten compounds can also be activated thermally.

The molybdenum and tungsten compounds to be used according to the invention can be those which contain one metal atom, or two metal atoms which are bonded via a single, double or triple bond. The methyl group or monosubstituted methyl group which is bonded to the metal is bonded at least twice, particularly preferably two to six times, and especially preferably two to four times, as a ligand. The other valencies of the molybdenum and tungsten are preferably satisfied by heat-stable neutral ligands, the definition of heat stability having been given above. This ligand preferably corresponds to the formula XI

in which R is H, —$CF_3$, —$SiR_{38}R_{39}R_{40}$, —$CR_{41}R_{42}R_{43}$, $C_6$–$C_{16}$aryl which is unsubstituted or substituted by $C_1$–$C_6$alkyl or $C_1$–$C_6$alkoxy or $C_4$–$C_{15}$heteroaryl having 1 to 3 heteroatoms from the group consisting of O, S and N; and $R_{41}$, $R_{42}$ and $R_{43}$ independently of one another are $C_1$–$C_{10}$alkyl, which is unsubstituted or substituted by $C_1$–$C_{10}$alkoxy, or $R_{41}$ and $R_{42}$ have this meaning and $R_{43}$ is $C_6$–$C_{10}$aryl or $C_4$–$C_9$heteroaryl, which is unsubstituted or substituted by $C_1$–$C_6$alkyl or $C_1$–$C_6$alkoxy; and $R_{38}$, $R_{39}$ and $R_{40}$ have the abovementioned meanings.

Alkyl $R_{38}$ to $R_{43}$ can be linear or branched and can preferably contain 1 to 8 and particularly preferably 1 to 4 C atoms. Aryl $R_{38}$ to $R_{43}$ is preferably phenyl or naphthyl.

Aryl R in formula XI is preferably phenyl or naphthyl.

Heteroaryl R in formula XI is preferably pyridinyl, furanyl, thiophenyl or pyrrolyl.

Preferred substituents for $R_{38}$ to $R_{43}$ in the context of the definitions are methyl, ethyl, methoxy and ethoxy. Examples of the radicals $R_{38}$ to $R_{43}$ have been given above under the compounds of the formula I.

In a preferred embodiment, the group R in formula XI is H, —$C(CH_3)_3$, —$C(CH_3)_2C_6H_5$, phenyl which is unsubstituted or substituted by methyl, ethyl, methoxy or ethoxy, —$CF_3$ or —$Si(CH_3)_3$.

The other valencies of the Mo(VI) and W(VI) atoms are optionally satisfied with identical or different ligands from the group consisting of =O, =N—$R_{44}$, secondary amines having 2 to 18 C atoms, $R_{45}$O—, $R_{45}$S—, halogen, optionally substituted cyclopentadienyl, bridged biscyclopentadienyl, tridentate monoanionic ligands and neutral ligands, such as, for example, ethers, nitriles, CO and tertiary phosphines and amines, in which the $R_{45}$ independently of one another are linear or branched $C_1$–$C_{18}$alkyl which is unsubstituted or substituted by $C_1$–$C_6$alkoxy or halogen, $C_5$- or $C_6$cycloalkyl which is unsubstituted or substituted by $C_1$–$C_6$alkyl, $C_1$–$C_6$alkoxy or halogen, phenyl which is unsubstituted or substituted by $C_1$–$C_6$alkyl, $C_1$–$C_6$alkoxy, $C_1$–$C_6$alkoxymethyl, $C_1$–$C_6$alkoxyethyl or halogen, or benzyl or phenylethyl which are unsubstituted or substituted by $C_1$–$C_6$alkyl, $C_1$–$C_6$alkoxy, $C_1$–$C_6$alkoxymethyl, $C_1$–$C_6$alkoxyethyl or halogen; and $R_{44}$ is linear or branched $C_1$–$C_{18}$alkyl which is unsubstituted or substituted by $C_1$–$C_6$alkoxy, $C_5$- or $C_6$cycloalkyl which is unsubstituted or substituted by $C_1$–$C_6$alkyl, $C_1$–$C_6$alkoxy or halogen, phenyl which is unsubstituted or substituted by $C_1$–$C_6$alkyl, $C_1$–$C_6$alkoxy, $C_1$–$C_6$alkoxymethyl, $C_1$–$C_6$alkoxyethyl, di($C_1$–$C_6$alkyl)amino, di($C_1$–$C_6$alkyl)amino-$C_1$–$C_3$alkyl or halogen, or benzyl or phenylethyl which are unsubstituted or substitued by $C_1$–$C_6$alkyl, $C_1$–$C_6$alkoxy, $C_1$–$C_6$alkoxymethyl, $C_1$–$C_6$alkoxyethyl or halogen.

Secondary amines are preferably those of the formula $R_{46}R_{47}N$—, in which $R_{46}$ and $R_{47}$ independently of one another are linear or branched $C_1$–$C_{18}$alkyl; $C_5$- or $C_6$cycloalkyl; benzyl or phenylethyl which are unsubstituted or substituted by $C_1$–$C_6$alkoxy or halogen, or $(C_1$–$C_6$alkyl)$_3$Si; or $R_{46}$ and $R_{47}$ together are tetramethylene, pentamethylene or 3-oxapentane-1,5-diyl. The alkyl preferably contains 1 to 12, and particularly preferably 1 to 6 C atoms. Some examples are dimethyl-, diethyl-, di-n-propyl-, di-i-propyl-, di-n-butyl-, methylethyl-, dibenzyl-, benzyl-methyl-, diphenyl- and phenylmethylamino and di(trimethylsilyl)amino.

Halogen as a ligand or a substituent is preferably F or Cl and particularly preferably Cl.

The cyclopentadienyl can be unsubstituted or substituted by one to five $C_1$–$C_4$alkyl, in particular methyl or —Si ($C_1$–$C_4$alkyl) [sic], in particular Si(CH$_3$)$_3$. Bridged cyclopentadienyls are, in particular, those of the formula $R_{48}$—A—$R_{48}$, in which $R_{48}$ is cyclopentadienyl which is unsubstituted or substituted by one to five $C_1$–$C_4$alkyl, in particular methyl or —Si($C_1$–$C_4$alkyl) [sic], in particular —Si(CH$_3$)$_3$, and A is —CH$_2$—, —CH$_2$—CH$_2$—, —Si (CH$_3$)$_2$—, —Si(CH$_3$)$_3$)$_2$—Si(CH$_3$)$_2$— or —Si(CH$_3$)$_2$—O—Si(CH$_3$)$_2$—.

Ethers as neutral ligands can be dialkyl ethers having 2 to 8 C atoms or cyclic ethers having 5 or 6 ring members. Some examples are diethyl ether, methyl ethyl ether, diethyl ether, di- n-propyl ether, di-i-propyl ether, di-n-butyl ether, ethylene glycol dimethyl ether, tetrahydroforan [sic] and dioxane.

Nitriles as neutral ligands can be aliphatic or aromatic nitriles having 1 to 12, preferably 1 to 8 C atoms. Some examples are acetonitrile, propionitrile, butylnitrile, benzonitrile and benzylnitrile.

Tertiary amines and phosphines as neutral ligands can be those having 3 to 24, preferably 3 to 18 C atoms. Some examples are trimethylamine and -phosphine, triethylamine and -phosphine, tri-n-propylamine and -phosphine, tri-n-butylamine and -phosphine, triphenylamine and -phosphine, tricyclohexylamine and -phosphine, phenyidimethylamine and -phosphine, benzyldimethylamine and -phosphine and 3,5-dimethylphenyl- dimethylamine and -phosphine.

The tridentate monoanionic ligands can be, for example, hydro(trispyrazol-1-yl)borates or alkyl(trispyrazol-1-yl) borates, which are unsubstituted or substituted by one to three $C_1$–$C_4$alkyl [cf. Trofimenko, S., Chem. Rev., 93:943–980 (1993)], or $[C_5(R'_5)Co(R_{50}R_{51}P=O)_3]^{\ominus}$, in which R' is H or methyl and $R_{50}$ and $R_{51}$ independently of one another are $C_1$–$C_4$alkyl, $C_1$–$C_4$alkoxy or phenyl [cf. Kläui, W., Angew. Chem. 102:661–670 (1990)].

Halogen as a substituent for the radicals $R_{44}$ and $R_{45}$ is preferably fluorine, and particularly preferably chlorine. The substituents alkyl, alkoxy or alkoxy in alkoxymethyl or -ethyl preferably contain 1 to 4, and in particular 1 or 2 C atoms. Examples are methyl, ethyl, n- and i-propyl, n-, i- and t-butyl, methoxy, ethoxy, n- and i-propyloxy and n-, i- and t-butyloxy.

Alkyl $R_{44}$ and $R_{45}$ preferably contain 1 to 12, particularly preferably 1 to 8, and especially preferably 1 to 4 C atoms. Alkyl is preferably branched alkyl. Some examples of $R_{44}$ are methoxy, ethoxy, n- and i-propyloxy, n-, i- and t-butyloxy, hexafluoro-i-propyloxy and hexa- and perfluorobutyloxy.

Some examples of substituted phenyl and benzyl $R_{44}$ and $R_{45}$ are p-methylphenyl or benzyl [sic], p-fluoro- or p-chlorophenyl or -benzyl, p-ethylphenyl or -benzyl, p-n- or i-propylphenyl or -benzyl, p-i-butylphenyl or -benzyl, 3-methyl-phenyl or -benzyl, 3-i-propylphenyl or -benzyl, 2,6-dimethylphenyl or -benzyl, 2,6-di-i-propylphenyl or -benzyl, 2,6-di-n- or -t-butylphenyl and -benzyl. $R_{45}$ is particularly preferably phenyl which is unsubstituted or substituted by $C_1$–$C_4$alkyl or $C_1$–$C_4$alkoxy.

In a preferred embodiment, the molybdenum and tungsten compounds correspond, in particular, to one of the formulae XII to XIIc

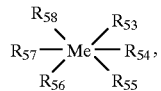
(XII)

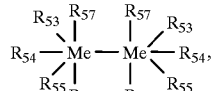
(XIIa)

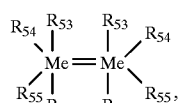
(XIIb)

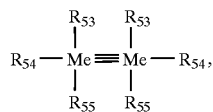
(XIIc)

in which

Me is Mo(VI) or W(VI);

at least two, preferably 2 to 4, of the radicals $R_{53}$ to $R_{58}$ are a radical —CH$_2$—R of the formula XI, in which R has the abovementioned meanings;

in each case two of the other radicals of $R_{53}$ to $R_{58}$ are =O or =N—$R_{44}$, and $R_{44}$ has the abovementioned meanings; and/or the other radicals from $R_{53}$ to $R_{58}$ are secondary amino having 2 to 18 C atoms, $R_{45}$O— or $R_{45}$S—, halogen, cyclopentadienyl or bridged biscyclopentadienyl or a neutral ligand, in which $R_{45}$ has the abovementioned meanings. The preferred meanings given above apply to the radicals R and $R_{38}$ to $R_{45}$.

In a particularly preferred embodiment, molybdenum and tungsten compounds of the formula XII which are used in the composition according to the invention are those in which a) $R_{53}$ to $R_{58}$ are a radical of the formula XI —CH$_2$—R, or b) $R_{53}$ and $R_{54}$ are a radical of the formula XI —CH$_2$—R, $R_{55}$ and $R_{56}$ together are the radical =N—$R_{44}$, and $R_{57}$ and $R_{58}$ together independently of one another are $R_{45}$—O— or halogen, or c) $R_{53}$ and $R_{54}$ together and $R_{55}$ and $R_{56}$ together are the radical =N—$R_{44}$, and $R_{57}$ and $R_{58}$ are a radical of the formula XI —CH$_2$—R, where R, $R_{44}$ and $R_{45}$ have the above meanings. The above preferred meanings apply to R, $R_{44}$ and $R_{45}$.

Particularly preferred compounds of the formula XIIc are those in which $R_{53}$, $R_{54}$ and $R_{55}$ are a radical of the formula XI, the radical of the formula XI particularly preferably being —CH$_2$—Si($C_1$–$C_4$alkyl)$_3$.

Molybdenum or tungsten compounds which are especially preferably used in the composition according to the invention are those of the formulae XIII, XIIIa or XIIIb

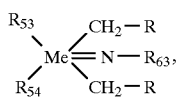 (XIII)

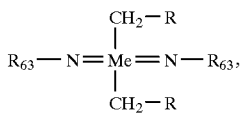 (XIIIa)

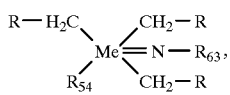 (XIIIb)

in which

Me is Mo(VI) or W(VI),

R is H, —C(CH$_3$)$_3$, —C(CH$_3$)$_2$—C$_6$H$_5$, —C$_6$H$_5$ or —Si(C$_1$–C$_4$alkyl)$_3$, R$_{63}$ is phenyl or phenyl which is substituted by 1 to 3 C$_1$–C$_4$alkyl or C$_1$–C$_4$alkoxy, R$_{53}$ is linear or branched C$_1$–C$_4$alkoxy which is unsubstituted or substituted by fluorine and R$_{54}$ has the same meaning as R$_{53}$ or is F, Cl or Br. R$_{53}$ is particularly preferably branched alkoxy, which is optionally partly or completely substituted by F, for example i-propyloxy, i- and t-butyloxy, hexafluoropopyloxy [sic] and nonafluoropropyloxy. R$_{54}$ is preferably Cl.

Some examples of molybdenum and tungsten compounds are:

W(=N—C$_6$H$_5$)(OC(CH$_3$)$_3$)(Cl)[(CH$_2$Si(CH$_3$)$_3$)]$_2$, [(CH$_3$)$_3$SiCH$_2$]$_3$Mo≡Mo[CH$_2$Si(CH$_3$)$_3$]$_3$,

W(=N—C$_6$H$_5$)(OC(CF$_3$)$_2$CH$_3$)$_2$[(CH$_2$Si(CH$_3$)$_3$)]$_2$, W(=NC$_6$H$_5$)[CH$_2$Si(CH$_3$)$_3$]$_3$Cl,

Mo(=N—2,6-dimethylC$_6$H5)$_2$[(CH$_2$–C$_6$H$_5$)]$_2$, W[2,6—(CH$_3$)$_2$C$_6$H$_3$N]$_2$(CH$_2$–C$_6$H$_5$)$_2$, Mo(=N—2,6-diisopropylC$_6$H$_3$)$_2$[(CH$_2$–C$_6$H$_5$)]$_2$, Mo(=N—2,6-diisopropylC$_6$H$_3$)$_2$[(CH$_2$C(CH$_3$)$_2$—C$_6$H$_5$)]$_2$ and Mo(=N—2,6-dimethylC$_6$H$_3$)$_2$(CH$_3$)$_2$(tetrahydrofuran)

The molybdenum and tungsten catalysts to be used according to the invention are known or can be prepared by known and analogous processes starting from the metal halides by means of Grignard reactions [see, for example, Huq, F., Mowat, W., Shortland, A., Skapski, A. C., Wilkinson, G., J. Chem. Soc., Chem. Commun. 1079–1080 (1971) or Schrock, R. R., Murdzeck, J. S., Bazan, G. C., Robbins, J., DiMare, M., O'Regan, M., J. Am. Chem. Soc., 112:3875–3886 (1990)].

3. Heat-stable titanium(IV), niobium(V), tantalum(V), molybdenum(VI) or tungsten(VI) compounds in which a silylmethyl group and at least one halogen are bound to the metal. These one-component catalysts are particularly photocatalytically active.

The titanium(IV), niobium(V) and tantalum(V) compounds to be used according to the invention are those which contain one metal atom. The molybdenum(VI) and tungsten (VI) compounds to be used according to the invention can be those which contain one metal atom, or two metal atoms which are bonded via a single, double or triple bond. The other valencies of the titanium, niobium, tantalum, molybdenum and tungsten are preferably satisfied with heat-stable neutral ligands, the definition of heat stability having been given above. The halogen bound to the metal atom is preferably F, Cl, Br and I, more preferably F, Cl and Br, and particularly preferably F or Cl. The silylmethyl ligand preferably corresponds to the formula XIV

 (XIV), in which

R$_{38}$, R$_{39}$ and R$_{40}$ independently of one another are C$_1$–C$_{18}$-alkyl, C$_5$- or C$_6$cycloalkyl or phenyl or benzyl which are unsubstituted or substituted by C$_1$–C$_6$alkyl or C$_1$–C$_6$alkoxy.

Alkyl R$_{38}$ to R$_{40}$ can be linear or branched and can preferably contain 1 to 12, particularly preferably 1 to 8, and in particular 1 to 4 C atoms. Methyl and ethyl are the particularly preferred alkyl.

Preferred substituents for phenyl and benzyl R$_{38}$ to R$_{40}$ in the context of the definitions are methyl, ethyl, methoxy and ethoxy.

In a preferred embodiment, R$_{38}$ to R$_{40}$ in the group of the formula XIV are C$_1$–C$_4$alkyl, phenyl or benzyl.

Some examples of the group of the formula XIV are —CH$_2$—Si(CH$_3$)$_3$, —CH$_2$—Si(C$_2$H$_5$)$_3$, —CH$_2$—Si(n—C$_3$H$_7$)$_3$, —CH$_2$—Si(n—C$_4$H$_9$)$_3$, —CH$_2$—Si(CH$_3$)$_2$(n—C$_4$H$_9$), —CH$_2$—Si(CH$_3$)$_2$(t—C$_4$H$_9$), —CH$_2$—Si(CH$_3$)$_2$(C$_2$H$_5$), —CH$_2$—Si(CH$_3$)$_2$[C(CH$_3$)$_2$CH(CH$_3$)$_2$, —CH$_2$—Si(CH$_3$)$_2$(n—C$_{12}$H$_{25}$), —CH$_2$—Si(CH$_3$)$_2$(n—C$_{18}$H$_{37}$), —CH$_2$—Si(C$_6$H$_5$)$_3$, —CH$_2$—Si(CH$_2$–C$_6$H$_5$)$_3$, —CH$_2$—Si$_2$—Si(—C$_6$H$_5$)(CH$_3$)$_2$ and —CH$_2$—Si(CH$_2$–C$_6$H$_5$)(CH$_3$)$_2$. —CH$_2$—Si(CH$_3$)$_3$ is especially preferred.

The other valencies of the Ti(IV), Nb(V), Ta(V), Mo(VI) and W(VI) atoms are optionally satisfied by identical or different neutral ligands, for example selected from the group consisting of =O, =N—R$_{44}$, secondary amines having 2 to 18 C atoms, R$_{45}$O—, R$_{45}$S—, halogen, optionally substituted cyclopentadienyl, bridged biscyclopentadienyl, tridentate monoanionic ligands and neutral ligands, such as, for example, ethers, nitriles, CO and tertiary phosphines and amines, in which the R$_{45}$ independently of one another are linear or branched C$_1$–C$_{18}$alkyl which is unsubstituted or substituted by C$_1$–C$_6$alkoxy or halogen, C5- or C$_6$cycloalkyl which is unsubstituted or substituted by C$_1$–C$_6$alkyl, C$_1$–C$_6$alkoxy or halogen, phenyl which is unsubstituted or substituted by C$_1$–C$_6$alkyl, C$_1$–C$_6$alkoxy, C$_1$–C$_6$alkoxymethyl, C$_1$–C$_6$alkoxyethyl or halogen, or benzyl or phenylethyl which are unsubstituted or substituted by C$_1$–C$_6$alkyl, C$_1$–C$_6$alkoxy, C$_1$–C$_6$alkoxymethyl, C$_1$–C$_6$alkoxyethyl or halogen, with the proviso that in the case of the titanium compounds, the ligand is not =O or =N—R$_{44}$. linear or branched C$_1$–C$_8$alkyl which is unsubstituted or substituted by C$_1$–C$_6$alkoxy, C$_5$— or C$_6$cycloalkyl which is unsubstituted or substituted by C$_1$–C$_6$alkyl, C$_1$–C$_6$alkoxy or halogen, phenyl which is unsubstituted or substituted by C$_1$–C$_6$alkyl, C$_1$–C$_6$alkoxy, C$_1$–C$_6$alkoxymethyl, C$_1$–C$_6$alkoxyethyl, di(C$_1$–C$_6$alkyl) amino, di(C$_1$–C$_6$alkyl)amino-C$_1$–C$_3$alkyl or halogen, or benzyl or phenylethyl which are unsubstituted or substituted by C$_1$–C$_6$alkyl, C$_1$–C$_6$alkoxy, C$_1$–C$_6$alkoxymethyl, C$_1$–C$_6$alkoxyethyl or halogen, with the proviso that in the case of the The meanings and preferred meanings of R$_{44}$ and R$_{45}$, of secondary amines, of halogen as a further ligand on the metal atoms or as a substituent, of cyclopentadienyl, ethers, nitriles, tertiary amines and phosphines as neutral ligands and of tridentate monoanionic ligands have been given above. The meanings and preferred meanings of alkyl, alkoxy or alkoxy as a substituent in alkoxymethyl or -ethyl have likewise been given above. In a preferred embodiment, the metal compounds correspond, in particular, to the formulae XV, XVa or XVb

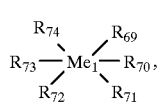  (XV)

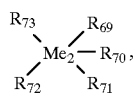  (XVa)

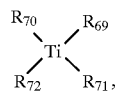  (XVb)

in which $Me_1$ is Mo(VI) or W(VI);

$Me_2$ is Nb(V) or Ta(V);

one of the radicals $R_{69}$ to $R_{74}$ is a radical —$CH_2$—$SiR_{38}R_{39}R_{40}$ of the formula XIV;

at least one of the radicals $R_{69}$ to $R_{74}$ is F, Cl or Br;

$R_{38}$, $R_{39}$ and $R_{40}$ independently of one another are $C_1-C_6$alkyl, $C_5$- or $C_6$cycloalkyl, or phenyl or benzyl which are unsubstituted or substituted by $C_1-C_6$alkyl or $C_1-C_6$alkoxy;

in formula XV two or in each case two and in formula XVa two of the other radicals of $R_{69}$ to $R_{74}$ each together are =O or =N—$R_{44}$, and $R_{44}$ is linear or branched $C_1-Cl_8$alkyl which is unsubstituted or substituted by $C_1-C_6$alkoxy, $C_5$- or $C_6$cycloalkyl which is unsubstituted or substituted by $C_1-C_6$alkyl, $C_1-C_6$alkoxy or halogen, phenyl which is unsubstituted or substituted by $C_1-C_6$alkyl, $C_1-C_6$alkoxy, $C_1-C_6$alkoxymethyl, $C_1-C_6$alkoxyethyl, di($C_1-C_6$alkyl)amino, di($C_1-C_6$alkyl)amino-$C_1-C_3$alkyl or halogen, or benzyl or phenylethyl which are unsubstituted or substituted by $C_1-C_6$alkyl, $C_1-C_6$alkoxy, $C_1-C_6$alkoxymethyl, $C_1-C_6$alkoxyethyl, di($C_1-C_6$alkyl)amino, di($C_1-C_6$alkyl)amino-$C_1-C_3$alkyl or halogen, and the other radicals are secondary amino having 2 to 18 C atoms, $R_{45}$O— or $R_{45}$S—, halogen, unsubstituted or substituted cyclopentadienyl or bridged biscyclopentadienyl or a neutral ligand, in which the $R_{45}$ independently of one another are linear or branched $C_1-C_{18}$alkyl which is unsubstituted or substituted by $C_1-C_6$alkoxy or halogen, $C_5$- or $C_6$cycloalkyl which is unsubstituted or substituted by $C_1-C_6$alkyl, $C_1-C_6$alkoxy or halogen, phenyl which is unsubstituted or substituted by $C_1-C_6$alkyl, $C_1-C_6$alkoxy, $C_1-C_6$alkoxymethyl, $C_1-C_6$alkoxyethyl, di($C_1-C_6$alkyl)amino, di($C_1-C_6$alkyl)amino-$C_1-C_3$alkyl or halogen, or benzyl or phenylethyl which are unsubstituted or substituted by $C_1-C_6$alkyl, $C_1-C_6$alkoxy, $C_1-C_6$alkoxymethyl, $C_1-C_6$alkoxyethyl, di($C_1-C_6$alkyl)amino, di($C_1-C_6$alkyl)amino-$C_1-C_3$alkyl or halogen; or in the formulae XV, XVa and XVb the other radicals independently of one another are secondary amino having 2 to 18 C atoms, $R_{45}$O— or $R_{45}$S—, halogen, unsubstituted or substituted cyclopentadienyl or bridged biscyclopentadienyl or a neutral ligand in which the $R_{45}$ independently of one another are linear or branched $C_1-C_{18}$alkyl which is unsubstituted or substituted by $C_1-C_6$alkoxy or halogen, $C_5$- or $C_6$cycloalkyl which is unsubstituted or substituted by $C_1-C_6$alkyl, $C_1-C_6$alkoxy or halogen, phenyl which is unsubstituted or substituted by $C_1-C_6$alkyl, $C_1-C_6$alkoxy, $C_1-C_6$alkoxymethyl, $C_1-C_6$alkoxyethyl, $C_1-C_6$alkyl)amino, di($C_1-C_6$alkyl)amino-$C_1-C_3$alkyl or halogen, or benzyl or phenylethyl which are unsubstituted or substituted by $C_1-C_6$alkyl, $C_1-C_6$alkoxy, $C_1-C_6$alkoxymethyl, $C_1-C_6$alkoxyethyl, di($C_1-C_6$alkyl)amino, di($C_1-C_6$alkyl)amino-$C_1-C_3$alkyl or halogen.

The preferred meanings given above apply to the radicals $R_{69}$ to $R_{73}$.

In a particularly preferred embodiment, metal compounds which are used in the process according to the invention are those of the formulae XV, XVa or XVb in which $R_{69}$ is a radical of the formula XIV —$CH_2SiR_{38}R_{39}R_{40}$ and $R_{70}$ is F, Cl or Br; and (a) in formula XV $R_{71}$ and $R_{72}$, and $R_{73}$ and $R_{74}$, in each case together, are the radical =N—$R_{44}$, or $R_{71}$ and $R_{72}$ together are the radical =N—$R_{44}$ and $R_{73}$ and $R_{74}$ independently of one another are unsubstituted or substituted cyclopentadienyl, $R_{45}$—O— or halogen, or (b) in formula XVa $R_7$ and $R_{72}$ together are the radical =N—$R_{44}$, and $R_{44}$ is unsubstituted or substituted cyclopentadienyl, $R_{45}$—O— or halogen, or in formula XVa $R_{71}$, $R_{72}$ and $R_{73}$ independently of one another are unsubstituted or substituted cyclopentadienyl, $R_{45}$—O— or halogen, or (c) in formula XVb $R_{71}$ and $R_{72}$ independently of one another are unsubstituted or substituted cyclopentadienyl, $R_{45}$—O— or halogen, where $R_{38}$ to $R_{44}$ have the above meanings. The above preferred meanings apply to $R_{38}$, $R_{39}$, $R_{40}$, $R_{44}$ and $R_{45}$.

Metal compounds which are especially preferably used in the process according to the invention are those of the formulae XVI, XVIa, XVIb, XVIc or XVId $$R_{74} \begin{array}{c} CH_2-R_{75} \\ | \\ Me_1=N-R_{63}, \\ | \\ R_{73} \; Z \end{array}$$  (XVI)

$$\begin{array}{c} CH_2-R_{75}, \\ | \\ R_{74} \diagdown \quad \diagup R_{71} \\ Me_1 \\ R_{73} \diagup \; | \; \diagdown R_{72} \\ Z \end{array}$$  (XVIa)

$$R_{73} - \begin{array}{c} CH_2-R_{75} \\ | \\ Me_2=N-R_{63}, \\ | \\ Z \end{array}$$  (XVIb)

$$R_{73} - \begin{array}{c} CH_2-R_{75}, \\ | \\ \diagup R_{71} \\ Me_2 \\ | \diagdown R_{72} \\ Z \end{array}$$  (XVIc)

(XVId)

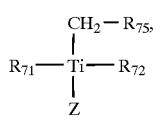

in which

Me$_1$ is Mo(VI) or W(VI);

Me$_2$ is Nb(V) or Ta(V);

R$_{75}$ is —Si(C$_1$–C$_4$alkyl)$_3$;

Z is Cl or Br;

R$_{63}$ is phenyl or phenyl which is substituted by 1 to 3 C$_1$–C$_4$alkyl or C$_1$–C$_4$alkoxy, (a) R$_{73}$ and R$_{74}$ in formula XVI together are the group —NR$_{63}$ or individually independently of one another are F, Cl, Br, linear or branched C$_1$–C$_4$alkoxy which is unsubstituted or substituted by fluorine, phenyloxy which is unsubstituted or substituted by C$_1$–C$_4$alkyl or C$_1$–C$_4$alkoxy, or cyclopentadienyl which is unsubstituted or substituted by C$_1$–C$_4$alkyl;

(b) R$_{71}$, R$_{72}$, R$_{73}$ and R$_{74}$ in formula XVIa independently of one another are F, Cl, Br, linear or, in particular, branched C$_1$–C$_4$alkyl which is unsubstituted or substituted by fluorine, phenyloxy which is unsubstituted or substituted by C$_1$–C$_4$alkyl or C$_1$–C$_4$alkoxy, or cyclopentadienyl which is unsubstituted or substituted by C$_1$–C$_4$alkyl;

(c) R$_{73}$ in formula XVIb is F, Cl, Br, linear or branched C$_1$–C$_4$alkoxy which is unsubstituted or substituted by fluorine, phenyloxy which is unsubstituted or substituted by C$_1$–C$_4$alkyl or C$_1$–C$_4$alkoxy, or cyclopentadienyl which is unsubstituted or substituted by C$_1$–C$_4$alkyl;

(d) R$_{71}$, R$_{72}$ and R$_{73}$ in formula XVIc independently of one another are F, Cl, Br, linear or, in particular, branched C$_1$–C$_4$alkoxy which is unsubstituted or substituted by fluorine, phenyloxy which is unsubstituted or substituted by C$_1$–C$_4$alkyl or C$_1$–C$_4$alkoxy, or cyclopentadienyl which is unsubstituted or substituted by C$_1$–C$_4$alkyl; and (e) R$_{71}$ and R$_{72}$ in formula XVId independently of one another are F, Cl, Br, linear or, in particular, branched C$_1$–C$_4$alkoxy which is unsubstituted or substituted by fluorine, phenyloxy which is unsubstituted or substituted by C$_1$–C$_4$alkyl or C$_1$–C$_4$alkoxy, or cyclopentadienyl which is unsubstituted or substituted by C$_1$–C$_4$alkyl. The alkoxy is particularly preferably branched alkoxy which is optionally partly or completely substituted by F, for example i-propyloxy, i- and t-butyloxy, hexafluoropopyloxy [sic] and nonafluoropropyloxy. The phenyloxy radical is, in particular, phenyloxy which is substituted by C$_1$–C$_4$alkyl in the 2,6-positions, for example 2,6-dimethylphenyloxy. Examples of substituted cyclopentadienyl radicals are mono- to pentamethylcyclopentadienyl and trimethylsilylcyclopentadienyl. R$_{63}$ is preferably phenyl or phenyl which is substituted by C$_1$–C$_4$alkyl, in particular phenyl or 3,5-dimethyl-, 2,6-dimethyl-, 3,5-diethyl- and 2,6-diethylphenyl.

Especially preferred compounds in the process according to the invention are those of the formulae XVII, XVIIa, XVIIb, XVIIc and XVIId

(XVII)

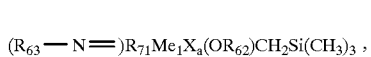
(XVIIa)

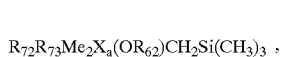
(XVIIb)

(XVIIc)

(XVIId)

in which

Me$_1$ is Mo(VI) or W(VI);

Me$_2$ is Nb(V) or Ta(V);

X$_a$ is F or Cl;

R$_{63}$ is phenyl or phenyl which is substituted by 1 or 2 C$_1$–C$_4$alkyl groups;

R$_{62}$ is branched C$_3$- or C$_4$alkyl which is optionally partly or completely substituted by fluorine, or phenyloxy, or phenyloxy which is substituted by 1 to 3 methyl or ethyl groups;

R$_{72}$ and R$_{73}$ independently of one another are cyclopentadienyl which is unsubstituted or substituted by 1 to 5 methyl groups, X$_a$ or R$_{62}$O—; and R$_{71}$ is cyclopentadienyl which is unsubstituted or substituted by 1 to 5 methyl groups, X$_a$ or R$_{72}$O—.

Some examples of titanium(IV), niobium(V), tantalum (V), molybdenum(VI) and tungsten(VI) compounds are [Cp is cyclopentadienyl and Me is Nb(V) or Ta(V)]: Ti[CH$_2$Si (CH$_3$)$_3$]Cl$_3$, Ti[CH$_2$Si(CH$_3$)$_3$]Br$_3$, Cp$_2$Ti[CH$_2$Si(CH$_3$)$_3$]Cl, (CH$_3$)$_2$Ti[CH$_2$Si(CH$_3$)$_3$]Cl, Cp$_2$Ti[CH$_2$Si(CH$_3$)$_3$]Br, Cp$_2$Ti [CH$_2$Si(Ch$_3$)$_3$]I CpTi[CH$_2$Si(CH$_3$)$_3$][CH$_3$]Cl, CpTi[CH$_2$Si (CH$_3$)$_3$]Br$_2$, [(CH$_3$)$_2$CHO]$_2$Ti[CH$_2$Si(CH$_3$)$_3$]Cl, [(CF$_3$)$_2$ CHO]$_2$Ti[CH$_2$Si(CH$_3$)$_3$]Cl, [(CF$_3$)$_2$CHO]CpTi[CH$_2$Si (CH$_3$)$_3$]Cl, [(CH$_3$)$_2$CHO]CpTi[CH$_2$Si(CH$_3$)$_3$]Cl, (C$_6$H$_5$O) CpTi[CH$_2$Si(CH$_3$)$_3$]Cl, (2,6-dimethyl-C$_6$H$_5$O)CpTi[CH$_2$Si (CH$_3$)$_3$]Cl, (2,6-dimethyl-C$_6$H$_5$O)$_2$Ti[CH$_2$Si(CH$_3$)$_3$]Cl, (2,6-dimethyl-C$_6$H$_5$O)Ti[CH$_2$Si(CH$_3$)$_3$]$_2$Br, [(CH$_3$)$_3$CO] CpTi[CH$_2$Si(CH$_3$)$_3$]Cl [(CF$_3$)$_2$(CH$_3$)CO]CpTi[CH$_2$Si(CH$_3$)$_3$]Cl, Me(=N—C$_6$H$_5$) [OCH(CH$_3$)$_2$][CH$_2$Si(CH$_3$)$_3$]Cl, Cp$_2$Me[(CH$_2$Si(CH$_3$)$_3$Cl$_2$, Me(=N—C$_6$H$_5$)[OCH(CF$_3$)$_2$][(CH$_2$Si(CH$_3$)$_3$]Cl, Me(=N-2,6-diisopropylC$_6$H$_3$)[(CH$_2$Si(CH$_3$)$_3$]Cl$_2$, Me(=N-2,6-diisopropylC$_6$H$_3$)[(CH$_3$)$_2$CHO][(CH$_2$Si(CH$_3$)$_3$]Cl, Me(=N-2,6-dimethylC$_6$H$_3$)(2,6-dimethyl-C$_6$H$_5$O)[CH$_2$Si (CH$_3$)$_3$]Cl, Me(=N-2,6-dimethylC$_6$H$_3$)((CF$_3$)$_2$CHO) [CH$_2$Si(CH$_3$)$_3$]Cl, (=N-2,6-dimethylC$_6$H$_3$)CpMe[(CH$_2$Si (CH$_3$)$_3$]Cl, (C$_6$H$_5$O)$_2$CpMe[(CH$_2$Si(CH$_3$)$_3$]Cl, (=N-3,5-dimethylC$_6$H$_3$)Me[2,6-dimethylC$_6$H$_3$O)][(CH$_2$Si(CH$_3$)$_3$)] Cl, CpMe[OCH(CH$_3$)$_2$]$_2$[(CH$_2$Si(CH$_3$)$_3$]Br, CpMe[OCH (CH$_3$)$_2$]$_2$[(CH$_2$Si(CH$_3$)$_3$]Cl, CpMe[OCH(CF$_3$)$_2$]$_2$[(CH$_2$Si (CH$_3$)$_3$]Cl, Cp$_2$Me(Methyl)[(CH$_2$Si(CH$_3$)$_3$]Cl, Cp$_2$Me [OCH(CH$_3$)$_2$][(CH$_2$Si(CH$_3$)$_3$]Cl, [OCH(CH$_3$)$_2$]$_2$Me[CH$_2$Si (CH$_3$)$_3$]Cl$_2$, Me(2,6-dimethylphenyloxy)(CH$_3$O)$_2$[(CH$_2$Si (CH$_3$)$_3$]Cl, Me[CH$_2$Si(CH$_3$)$_3$][OCH(CH$_3$)](CF$_3$O)$_2$Cl, W(=N—C$_6$H$_5$)[(OC(CH$_3$)$_3$][CH$_2$—Si(CH$_3$)$_3$]Cl$_2$, (2,6-diisopropylphenyloxY)$_2$Me[CH$_2$Si(CH$_3$)$_3$]Cl$_2$, Cp$_2$Me[OC (CH$_3$)$_3$][(CH$_2$Si(CH$_3$)$_3$]Cl, CpMe[OC(CH$_3$)(CF$_3$)$_2$]$_2$ [(CH$_2$Si(CH$_3$)$_3$]Cl, Mo$_2$[(CH$_2$—Si(CH$_3$)$_3$)(OCH$_2$C(CH$_3$)$_3$) Cl]$_2$, Mo(=N-2,6-diisopropylC$_6$H$_3$)2]CH$_2$—Si(CH$_3$)$_3$]Cl, W(=N—C$_6$H$_5$)[(OC(CH$_3$)$_3$]$_2$[CH$_2$—Si(CH$_3$)$_3$]Cl, Mo(=N—C$_6$H$_5$)$_2$[CH$_2$—Si(CH$_3$)$_3$]Cl, Mo(=N-2,6-diisopropylc$_6$H$_3$)[(OCH$_2$C(CH$_3$)$_3$]$_2$[CH$_2$—Si(CH$_3$)$_3$CL.

The titanium, niobium, tantalum, molybdenum and tungsten compounds to be used according to the invention are known or can be prepared by known and analogous processes starting from optionally correspondingly substituted metal halides by means of Grignard reactions [Schrock, R. R., Murdzeck, J. S., Bazan, G. C., Robbins, J., DiMare, M., O'Regan, M., J. Am. Chem. Soc., 112:3875–3886 (1990)].

4. Other suitable photoactive one-component catalysts are niobium(V) or tantalum(V) compounds which contain at least two methyl groups or two monosubstituted methyl groups bonded to the metal, the substituent containing no hydrogen atom in the a position. These compounds are also thermal catalysts.

The niobium(V) and tantalum(V) compounds to be used according to the invention contain one metal atom. The methyl group or monosubstituted methyl group which is bonded to the metal is bonded at least twice, particularly preferably two to five times, and especially preferably two or three times, as a ligand. This ligand preferably corresponds to the formula XI

—CH$_2$—R   (XI)

where R has the meanings and preferred meanings given above.

The other valencies of the niobum and tantalum atom are preferably satisfied with heat stable neutral ligands, a large number of which are known. The number of neutral ligands can also exceed the stoichiometrically possible number (solvates). The definition of heat stability has been given in the introduction.

The meanings and preferred meanings of neutral ligands have been given above.

In a preferred embodiment, the niobium and tantalum compounds correspond, in particular, to the formula XVIII

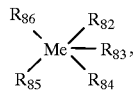

(XVIII)

in which

Me is Nb(V) or Ta(V), at least two, preferably 2 or 3, of the radicals $R_{82}$ to $R_{86}$ are a radical —CH$_2$—R of the formula XI, in which R has the meanings and preferred meanings given above, two of the other radicals from $R_{82}$ to $R_{86}$ together are =O or =N—$R_{44}$, and $R_{44}$ is linear or branched $C_1$–$C_{18}$alkyl which is unsubstituted or substituted by $C_1$–$C_6$alkoxy, $C_5$- or $C_6$cycloalkyl which is unsubstituted or substituted by $C_1$–$C_6$alkyl, $C_1$–$C_6$alkoxy or halogen, phenyl which is unsubstituted or substituted by $C_1$–$C_6$alkyl, $C_1$–$C_6$alkoxy, $C_1$–$C_6$alkoxymethyl, $C_1$–$C_6$alkoxyethyl, di($C_1$–$C_6$alkyl)amino, di($C_1$–$C_6$alkyl)amino-$C_1$–$C_3$alkyl or halogen, or benzyl or phenylethyl which are unsubstituted or substituted by $C_1$–$C_6$alkyl, $C_1$–$C_6$alkoxy, $C_1$–$C_6$alkoxymethyl, $C_1$–$C_6$alkoxyethyl, di($C_1$–$C_6$alkyl)amino, di($C_1$–$C_6$alkyl)amino-$C_1$–$C_3$alkyl or halogen; and/or the other radicals from $R_{82}$ to $R_{86}$ independently of one another are secondary amino having 2 to 18 C atoms, $R_{45}$O—, $R_{45}$S—, halogen, cyclopentadienyl or bridged biscyclopentadienyl or a neutral ligand, in which the $R_{45}$ independently of one another are linear or branched $C_1$–$C_{18}$alkyl which is unsubstituted or substituted by $C_1$–$C_6$alkoxy or halogen, $C_5$- or $C_6$cycloalkyl which is unsubstituted or substituted by $C_1$–$C_6$alkyl, $C_1$–$C_6$alkoxy or halogen, phenyl which is unsubstituted or substituted by $C_1$–$C_6$alkyl, $C_1$–$C_6$alkoxy, $C_1$–$C_6$alkoxymethyl, $C_1$–$C_6$alkoxyethyl, di($C_1$–$C_6$alkyl)amino, di($C_1$–$C_6$alkyl)amino-$C_1$–$C_3$alkyl or halogen, or benzyl or phenyethyl which are unsubstituted or substituted by $C_1$–$C_6$alkyl, $C_1$–$C_6$alkoxy, $C_1$–$C_6$alkoxymethyl, $C_1$–$C_6$alkoxyethyl, di($C_1$–$C_6$alkyl)amino, di($C_1$–$C_6$alkyl)amino-$C_1$–$C_3$alkyl or halogen.

In a particularly preferred embodiment, the niobium and tantalum compounds of the formula XVIII used are those in which a) $R_{82}$ to $R_{86}$ are each a radical of the formula XI —CH$_2$—R, or b) $R_{82}$ and $R_{83}$ are each a radical of the formula XI —CH$_2$—R, $R_{84}$ and $R_{85}$ together are the radical =N—$R_{44}$, and $R_{86}$ is unsubstituted or substituted cyclopentadienyl, $R_{45}$—O— or halogen, or c) $R_{82}$, $R_{83}$ and $R_{84}$, are each a radical of the formula XI —CH$_2$—R, and $R_{85}$ and $R_{86}$ together are the radical =N—$R_{44}$, or $R_{82}$, $R_{83}$, $R_{84}$ and $R_8$, are a radical of the formula XI —CH$_2$—R and $R_{86}$ is unsubstituted or substituted cyclopentadienyl, $R_{45}$—O— or halogen, where R, $R_{44}$ and $R_{45}$ have the above meanings. The above preferred meanings apply to R, $R_{44}$ and $R_{45}$.

Niobium and tantalum compounds which are especially preferably used in the process according to the invention are those of the formulae IXX, IXXa or IXXb

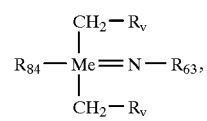

(IXX)

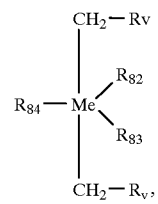

(IXXa)

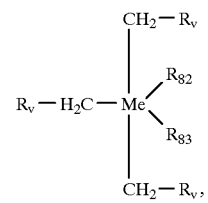

(IXXb)

in which

Me is Nb(V) or Ta(V), $R_v$ is H, —C(CH$_3$)$_3$, —C(CH$_3$)$_2$—C$_6$H$_5$, —C$_6$H or —Si(C$_1$–C$_4$alkyl)$_3$, $R_{63}$ is phenyl or phenyl which is substituted by 1 to 3 $C_1$–$C_4$alkyl or $C_1$–$C_4$alkoxy, $R_{84}$ in formula IXX is the group —CH$_2$—R or F, Cl, Br, linear or, in particular, branched $C_1$–$C_4$alkoxy which is unsubstituted or substituted by fluorine, phenyloxy which is unsubstituted or substituted by $C_1$–$C_4$alkyl or $C_1$–$C_4$alkoxy, or cyclopentadienyl which is unsubstituted or substituted by $C_1$–$C_4$alkyl;

$R_{82}$, $R_{83}$ and $R_{84}$ in formula IXXa independently of one another are F, Cl, Br, linear or, in particular, branched $C_1$–$C_4$alkoxy which is unsubstituted or substituted by fluorine, phenyloxy which is unsubstituted or substituted by $C_1$–$C_4$alkyl or $C_1$–$C_4$alkoxy, or cyclopentadienyl which is unsubstituted or substituted by $C_1$–$C_4$alkyl; and $R_{82}$ and $R_{83}$ in formula IXXb independently of one another are F, Cl, Br, linear or, in particular, branched $C_1$–$C_4$alkoxy which is unsubstituted or substituted by fluorine, phenyloxy which is unsubstituted or substituted by $C_1$–$C_4$alkyl or $C_1$–$C_4$alkoxy, or cyclopentadienyl which is unsubstituted or substituted by $C_1$–$C_4$alkyl. The alkoxy is particularly preferably branched alkoxy, which is optionally partly or completely substituted by F, for example i-propyloxy, i- and t-butyloxy, hexafluoropopyloxy [sic] or nonafluoropropyloxy.

Some examples of niobium(V) and tantalum(V) compounds are [Cp is cyclopentadienyl and Me is Nb(V) or Ta(V)]: $Me[CH_2Si(CH_3)_3]_5$, $Cp_2Me[(CH_2C(CH_3)_2—C_6H_5)]_3$, $Me(=N-2,6-dimethylC_6H_3)(CH_3)_3$, $Me(=N—C_6H_5)[OC(CH_3)_3][CH_2Si(CH_3)_3)]_2$, $Me(=N-2,6-diisopropylC_6H_3)[(CH_2—C_6H_5)]_3$, $Me(=N—C_6H_5)[OCCH_3(CF_3)_2][(CH_2Si(CH_3)_3)]_2$, $CpMe[OCCH_3(CF_3)_2]_2[(CH_2—C_6H_5)]_2$, $Me(=N-2,6-diisopropylC_6H_3)[(CH_2C(CH_3)_2—C_6H_5)]_2Cl$, $Cp_2Me(CH_3)_2[OCH(CH_3)_2]$, $Me(=N-2,6-dimethylC_6H_3)[(CH_2—C_6H_5)]_3$, $CpMe[OCH(CH_3)_2]_2[(CH_2Si(CH_3)_3)_3)]_2$, $Cp_2Me[(CH_2—C_6H_5)_3$, $Me[CH_2Si(CH_3)_3]_3Cl_2$, $Me[CH_2Si(CH_3)_3]_3[OCH_2C(CH_3)_3]_2$, $Cp_2Me[3,5-dimethylC_6H_3O)][(CH_2Si(CH_3)_3)]_2$, $Me(2,6-diisopropylphenyloxy)_2(CH_3)_3$, $Cp_2Me(CH_3)_3$, $Me(2,6-dimethylphenyloxy)_2(CH_3)_3$, $Me[CH_2Si(CH_3)_3]_3CpMe[OC(CH_3)_3]_2[(CH_2—C_6H_5)]_2$ and $Cp_2Me[(CH_2Si(CH_3)_3)]_3]$.

The niobium and tantalum compounds to be used according to the invention are known or can be prepared by known and analogous processes starting from the optionally substituted metal halides via Grignard reactions and/or substitution reactions [Schrock, R. R., Murdzeck, J. S., Bazan, G. C., Robbins, J., DiMare, M., O'Regan, M., J. Am. Chem. Soc., 112:3875–3886 (1990)].

5. Other suitable photoactive one-component catalysts are titanium(IV) compounds which contain, bonded to the metal, at least two methyl groups or two monosubstituted methyl groups, the substituent containing no hydrogen atom in the a position. These compounds are also thermal catalysts.

The titanium(IV) compounds to be used according to the invention contain one metal atom. The methyl group or monosubstituted methyl group which is bonded to the metal is bonded at least twice, particularly preferably two to four times, and especially preferably two or three times, as a ligand. This ligand preferably corresponds to the formula XI

—CH$_2$—R (XI)

where R has the meanings and preferred meanings given above.

The other valencies of the titanium atom are preferably satisfied with heat-stable neutral ligands, a large number of which are known. The number of neutral ligands can also exceed the stoichiometrically possible number (solvates). The definition of heat stability has been given in the introduction.

The neutral ligands are, advantageously, identical or different ligands, for example from the group consisting of secondary amines having 2 to 18 C atoms, $R_{45}O$—, $R_{45}S$—, halogen, cyclopentadienyl, bridged biscyclopentadienyl, tridentate monoanionic ligands and neutral ligands, for example ethers and amines, in which the $R_{62}$ independently of one another are linear or branched $C_1$–$C_{18}$alkyl which is unsubstituted or substituted by $C_1$–$C_6$alkoxy or halogen, $C_5$- or $C_6$cycloalkyl which is unsubstituted or substituted by $C_1$–$C_6$alkyl, $C_1$–$C_6$alkoxy or halogen, phenyl which is unsubstituted or substituted by $C_1$–$C_6$alkyl, $C_1$–$C_6$alkoxy, $C_1$–$C_6$alkoxymethyl, $C_1$–$C_6$alkoxyethyl or halogen, or benzyl or phenylethyl which are unsubstituted or substituted by $C_1$–$C_6$alkyl, $C_1$–$C_6$alkoxy, $C_1$–$C_6$alkoxymethyl, $C_1$–$C_6$alkoxyethyl or halogen.

The meanings and preferences of $R_{45}$, of secondary amines, of halogen as a further ligand on the metal atoms or as a substituent, of cyclopentadienyl, ethers, nitriles, tertiary amines and phosphines as neutral ligands and of tridentate monoanionic ligands have been given above. The meanings and meanings of alkyl, alkoxy or alkoxy as a substituent in alkoxymethyl or -ethyl have likewise been given above.

In a preferred embodiment, the titanium(IV) compounds correspond, in particular, to the formulae XX

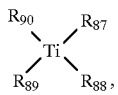

(XX)

in which at least two, preferably 2 or 3, of the radicals $R_{87}$ to $R_{90}$ are a radical —CH$_2$—R of the formula XI, in which R has the meanings and preferred meanings given above; and the other radicals $R_{87}$ to $R_{90}$ are secondary amino having 2 to 18 C atoms, $R_{45}O$—, $R_{45}S$—, halogen, cyclopentadienyl or bridged biscyclopentadienyl or a neutral ligand, in which the $R_{45}$ independently of one another are linear or branched $C_1$–$C_{18}$alkyl which is unsubstituted or substituted by $C_1$–$C_6$alkoxy or halogen, $C_5$- or $C_6$cycloalkyl which is unsubstituted or substituted by $C_1$–$C_6$alkyl, $C_1$–$C_6$alkoxy or halogen, phenyl which is unsubstituted or substituted by $C_1$–$C_6$alkyl, $C_1$–$C_6$alkoxy, $C_1$–$C_6$alkoxymethyl, $C_1$–$C_6$alkoxyethyl, di($C_1$–$C_6$alkyl)amino, di($C_1$–$C_6$alkyl)amino-$C_1$–$C_3$alkyl or halogen, or benzyl or phenylethyl which are unsubstituted or substituted by $C_1$–$C_6$alkyl, $C_1$–$C_6$alkoxy, $C_1$–$C_6$alkoxymethyl, $C_1$–$C_6$alkoxyethyl, di($C_1$–$C_6$alkyl)amino, di($C_1$–$C_6$alkyl)amino$C_1$–$C_3$alkyl or halogen.

In a particularly preferred embodiment, the titanium(IV) compounds of the formula XX which are used in the process according to the invention are those in which a) $R_{87}$ to $R_{90}$ are a radical of the formula XI —CH$_2$—R, or b) $R_{87}$ and $R_{88}$ are a radical of the formula XI —CH$_2$—R, and $R_{89}$ and $R_{90}$ independently of one another are unsubstituted or substituted cyclopentadienyl, $R_{45}$—O— or halogen, or c) $R_{87}$, $R_{88}$ and $R_{89}$ are a radical of the formula XI —CH$_2$—R, and $R_{90}$ is unsubstituted or substituted cyclopentadienyl, $R_{45}$—O— or halogen, where R and $R_{45}$ have the above meanings. The above preferred meanings apply to R and $R_{45}$.

Titanium(IV) compounds which are especially preferably used in the process according to the invention are those of the formulae XXIa or XXIb

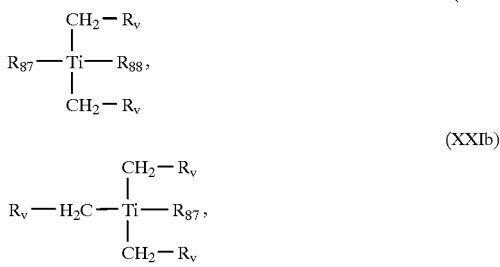

(XXIa)

(XXIb)

in which

R$_v$ is H, —C(CH$_3$)$_3$, —C(CH$_3$)$_2$—C$_6$H$_5$, —C$_6$H$_5$ or —Si(C$_1$–C$_4$alkyl)$_3$, and R$_{87}$ and R$_{88}$ independently of one another are F, Cl, Br, linear or, in particular, branched C$_1$–C$_4$alkoxy which is unsubstituted or substituted by fluorine, phenyloxy which is unsubstituted or substituted by C$_1$–C$_4$alkyl or C$_1$–C$_4$alkoxy, or cyclopentadienyl which is unsubstituted or substituted by C$_1$–C$_4$alkyl. The alkoxy is particularly preferably branched alkoxy, which is unsubstituted or partly or completely substituted by F, for example i-propyloxy, i- and t-butyloxy, hexafluoropropyloxy and nonafluoropropyloxy.

In a preferred embodiment of the invention, the titanium (IV) compounds contain a halogen atom, in particular Cl or Br, bonded to the titanium if the radical R in the group —CH$_2$—R is —SiR$_{38}$R$_{39}$R$_{40}$. Compounds which are especially preferred are then those of the formula XXII

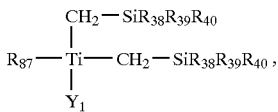

(XXII)

in which

Y$_1$ is F, Cl or Br,

R$_{38}$, R$_{39}$ and R$_{40}$ independently of one another are C$_1$–C$_{18}$alkyl, C$_5$- or C$_6$-cycloalkyl or phenyl or benzyl which are unsubstituted or substituted by C$_1$–C$_6$alkyl or C$_1$–C$_6$alkoxy; and R$_{87}$ is the group —CH$_2$—SiR$_{38}$R$_{39}$R$_{40}$, F, Cl, Br, linear or, in particular, branched C$_1$–C$_4$alkoxy which is unsubstituted or substituted by fluorine, phenyloxy which is unsubstituted or substituted by C$_1$–C$_4$alkyl or C$_1$–C$_4$alkoxy, or cyclopentadienyl which is unsubstituted or substituted by C$_1$–C$_4$alkyl. R$_{38}$, R$_{39}$ and R$_{40}$ are preferably C$_1$–C$_4$alkyl, phenyl or benzyl, and R$_{87}$ is preferably Cl, C$_3$- or C$_4$-alkyl which is unsubstituted or substituted by fluorine, or phenyl or benzyl which are unsubstituted or substituted by C$_1$–C$_4$alkyl or C$_1$–C$_4$alkoxy, Some examples of titanium(IV) compounds are [Cp is cyclopentadienyl]: Ti[CH$_2$Si(CH$_3$)$_3$]$_4$, Ti[OCH(CF$_3$)$_2$]$_2$[(CH$_2$Si(CF$_3$)$_3$]$_2$, CpTi[(CH$_2$C(CH$_3$)$_2$-C$_6$H$_5$)]$_2$Cl, CpTi[(CH$_2$-C$_6$H$_5$)]$_3$, TiCl$_2$[CH$_2$Si(CH$_3$)$_3$)]$_2$, [OCH(CF$_3$)$_2$]Ti[(CH$_2$-C$_6$H$_5$)]$_3$, CpBrTi[(CH$_2$C(CH$_3$)$_2$-C$_6$H$_5$)]$_2$, CpTi[2,6-dimethylC$_6$H$_3$O)][(CH$_2$Si(CH$_3$)$_3$)]$_2$, Ti[OCH(CH$_3$)$_2$]$_2$[(CH$_2$-C$_6$H$_5$)]$_2$, ClTi[OCH(CH$_3$)$_2$][(CH$_2$Si(CH$_3$)$_3$)]$_2$, CpTi[OCH(CF$_3$)$_2$][(CH$_2$-C$_6$H$_5$)]$_2$, CpTi(methyl)$_3$, CpTi(methyl)$_2$[OCH(CH$_3$)$_2$], Ti[CH$_2$Si(CH$_3$)$_3$]$_2$Br$_2$, Ti(2,6-dimethylphenyloxy)$_2$(CH$_3$)$_2$, Cp$_2$Ti(CH$_3$)$_2$, Ti[CH$_2$Si(CH$_3$)$_3$]$_3$[OCH(CH$_3$)] and Ti(2,6-diisopropylphenyloxy)$_2$(CH$_3$)$_2$.

The titanium(IV) compounds to be used according to the invention are known or can be prepared by known and analogous processes starting from the metal halides by Grignard reactions or other known substitution reactions [see Clauss, K., Bestian, H., Justus Liebigs Ann. Chem., 654:8–19 (1962)].

6. Other suitable photocatalytically active compounds are ruthenium or osmium compounds which contain at least one phosphine group, at least one photolabile ligand, and optionally neutral ligands bonded to the metal atom, a total of 2 to 5 ligands being bonded, and which contain acid anions for balancing the charge. Total in the context of the invention means the sum of the phosphine groups, photolabile ligands and neutral ligands. The neutral ligands are also called non-photolabile ligands. Preferably 2 to 4, and particularly preferably 2 or 3, ligands are bonded in total.

The osmium compounds are also thermally active catalysts. The ruthenium compounds are also thermal catalysts if the phosphine group contains no linear alkyl or alkoxy group, but bulky groups, for example secondary and tertiary alkyl or alkoxy groups (i-propyl or i- and t-butyl), or cycloalkyl groups, or phenyl groups or phenyloxy groups which are unsubstituted or substituted by 1 to 3 C$_1$–C$_4$alkyl or -alkoxy.

The phosphine group is preferably tertiary phosphines having 3 to 40, more preferably 3 to 30 and particularly preferably 3 to 24 C atoms.

The other valencies of the ruthenium and osmium are preferably satisfied with heat-stable neutral ligands, a large number of which are known. The number of neutral ligands can also exceed the stoichiometrically possible number (solvates).

In the ruthenium and osmium compounds to be used according to the invention, a monophosphine can be bonded one to three times and preferably two or three times and a diphosphine can be bonded once to the metal atom. Preferably 1 or 2 photolabile ligands are bonded in the ruthenium and osmium catalysts. The phosphine ligands preferably correspond to the formulae XXIII and XXIIIa

 (XXIII),

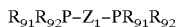 (XXIIIa), in which R$_{91}$, R$_{92}$ and R$_{93}$ independently of one another are H, C$_1$–C$_{20}$alkyl, C$_4$–C$_{12}$cycloalkyl which is unsubstituted or substituted by C$_1$–C$_6$alkyl, C$_1$–C$_6$haloalkyl or C$_1$–C$_6$alkoxy, or C$_6$–C$_{16}$aryl which is unsubstituted or substituted by C$_1$–C$_6$alkyl, C$_1$–C$_6$haloalkyl or C$_1$–C$_6$alkoxy, or C$_7$–C$_{16}$aralkyl which is unsubstituted or substituted by C$_1$–C$_6$alkyl, C$_1$–C$_6$haloalkyl or C$_1$–C$_6$alkoxy; the radicals R$_{91}$ and R$_{92}$ together are tetra- or pentamethylene which is unsubstituted or substituted by C$_1$–C$_6$alkyl, C$_1$–C$_6$haloalkyl or C$_1$–C$_6$alkoxy, or tetra- or pentamethylene which is unsubstituted or substituted by C$_1$–C$_6$alkyl, C$_1$–C$_6$haloalkyl or C$_1$–C$_6$alkoxy and fused with 1 or 2 1,2-phenylene, and R$_{93}$ has the meaning given above; and Z$_1$ is linear or branched C$_2$–C$_{12}$alkylene which is unsubstituted or substituted by C$_1$–C$_4$alkoxy, 1,2- or 1,3-cycloalkylene which has 4 to 8 C atoms and is unsubstituted or substituted by C$_1$–C$_4$alkyl or C$_1$–C$_4$alkoxy, or 1,2 or 1,3-heterocycloalkylene which has 5 or 6 ring members and one heteroatom from the group consisting of O or N and is unsubstituted or substituted by C$_1$–C$_4$alkyl or C$_1$–C$_4$alkoxy.

The radicals $R_{91}$, $R_{92}$ and $R_{93}$ are preferably identical radicals.

If $R_{91}$, $R_{92}$ and $R_{93}$ are substituted, the substituents are preferably $C_1$–$C_4$alkyl, $C_1$–$C_4$haloalkyl or $C_1$–$C_4$alkoxy. Halogen is preferably Cl and particularly preferably F. Examples of preferred substituents are methyl, methoxy, ethyl, ethoxy and trifluoromethyl. $R_{91}$, $R_{92}$ and $R_{93}$ are preferably substituted by 1 to 3 substituents. Substituents are preferably in one or both ortho and/or meta positions relative to the C atom of the P—C bond in the phosphine.

Alkyl $R_{91}$, $R_{92}$ and $R_{93}$ can be linear or branched and can preferably contain 1 to 12, more preferably 1 to 8, and particularly preferably 1 to 6 C atoms. Examples of alkyl are methyl, ethyl, n- and i-propyl, n-, i- and t-butyl and the isomers of pentyl, hexyl, heptyl, octyl, nonyl, decyl, undecyl, dodecyl, tridecyl, tetradecyl, pentadecyl, hexadecyl, heptadecyl, octadecyl and eicosyl. Preferred examples are methyl, ethyl, n- and i-propyl, n-, i- and t-butyl, 1-, 2- or 3-pentyl and 1-, 2-, 3- or 4-hexyl.

Cycloalkyl $R_{91}$, $R_{92}$ and $R_{93}$ are preferably $C_5$–$C_8$cycloalkyl, and particularly preferably $C_5$- or $C_6$cycloalkyl. Some examples are cyclobutyl, cycloheptyl, cyclooctyl and, in particular, cyclopentyl and cyclohexyl. Examples of substituted cycloalkyl are methyl-, dimethyl-, trimethyl-, methoxy-, dimethoxy-, trimethoxy-, trifluoromethyl-, bistrifluoromethyl and tristrifluoromethyl-cyclopentyl and -cyclohexyl.

Aryl $R_{91}$, $R_{92}$ and $R_{93}$ are preferably $C_6$–$C_{12}$aryl, and particularly preferably phenyl or naphthyl. Examples of substituted aryl are methyl-, dimethyl-, trimethyl-, methoxy-, dimethoxy-, trimethoxy-, trifluoromethyl-, bistrifluoromethyl and tristrifluoromethylphenyl.

Aralkyl $R_{91}$, $R_{92}$ and $R_{93}$ are preferably $C_7$–$C_{13}$aralkyl, where the alkylene group in the aralkyl is preferably methylene. The aralkyl is particularly preferably benzyl. Examples of substituted aralkyl are methyl-, dimethyl-, trimethyl-, methoxy-, dimethoxy-, trimethoxy-, trifluoromethyl-, bistrifluoromethyl and tristrifluoromethyl-benzyl.

Examples of optionally substituted or fused tetra- or pentamethylene bonded to the P atom are

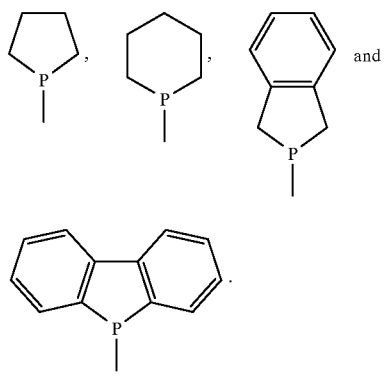

Other suitable phosphines are cycloaliphatics which have 6 to 8 ring carbon atoms and are bridged with a =PRa group, for example

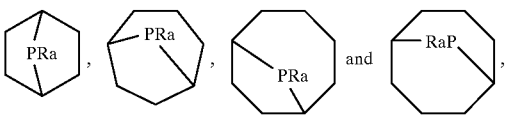

in which Ra is $C_1$–$C_6$alkyl, cyclohexyl, benzyl, or phenyl which is unsubstituted or substituted by 1 or 2 $C_1$–$C_4$alkyl.

Linear or branched alkylene $Z_1$ is preferably 1,2-alkylene or 1,3-alkylene having preferably 2 to 6 C atoms, for example ethylene, 1,2-propylene or 1,2-butylene.

Examples of cycloalkylene $Z_1$ are 1,2- and 1,3-cyclopentylene and 1,2- or 1,3-cyclohexylene. Examples of heterocycloalkylene $Z_1$ are 1,2- and 1,3-pyrrolidine, 1,2- and 1,3-piperidine and 1,2- and 1,3-tetrahydrofuran.

In a preferred embodiment, the phosphine ligands correspond to the formula XXIII in which $R_{91}$, $R_{92}$ and $R_{93}$ independently of one another are H, $C_1$–$C_6$alkyl, cyclopentyl or cyclohexyl which are unsubstituted or substituted by $C_1$–$C_4$alkyl, or phenyl which is unsubstituted or substituted by $C_1$–$C_4$alkyl, $C_1$–$C_4$alkyl [sic] $C_1$–$C_4$alkoxy or trifluoromethyl, or benzyl which is unsubstituted or substituted by $C_1$–$C_4$alkyl, $C_1$–$C_4$alkyl [sic] $C_1$–$C_4$alkoxy or trifluoromethyl. Particularly preferred examples of phosphine ligands of the formula XXIII are $(C_6H_5)_3P$, $(C_6H_5CH_2)_3P$, $(C_5H_{11})_3P$, $(CH_3)_3P$, $(C_2H_5)_3P$, $(n-C_3H_7)_3P$, $(i-C_3H_7)_3P$, $(n-C_4H_9)_3P$, $(C_6H_5)_2HP$, $(C_6H_5CH_2)_2HP$, $(C_5H_{11})_2HP$, $(C_2H_5)_2HP$, $(n-C_3H_7)_2HP$, $(i-C_3H_7)_2HP$, $(n-C_4H_9)_2HP$, $(C_6H_5)H_2P$, $(n-C_4H_9)H_2P$, $(C_6H_5CH_2)H_2P$, $(C_5H_{11})H_2P$, $(CH_3)H_2P$, $(CH_3)_2HP$, $(C_2H_5)H_2P$, $(n-C_3H_7)H_2P$, $(i-C_3H_7)H_2P$, $PH_3$ (2-methyl-$C_6H_4)_3P$, (3-$CH_3$—$C_6H_4)_3$ P, (4-$C_2H_5$—$C_6H_4)_3P$, (4-$CH_3$—$C_6H_4)_3P$, (2,4-di-$CH_3$—$C_6H_3)_3P$, (2,6-di-$CH_3$—$C_6H_3)_3P$, (2-$C_2H_5$—$C_6H_4)_3P$, (3-$C_2H_5$—$C_6H_4)_3P$, (2-n-$C_3H_7$—$C_6H_4)_3P$, (3-n-$C_3H_7$—$C_6H_4)_3P$, (4-n-$C_3H_7$—$C_6H_4)_3P$, (2-i-$C_3H_7$—$C_6H_4)_3P$, (3-i-$C_3H_7$—$C_6H_4)_3P$, (4-i-$C_3H_7$—$C_6H_4)_3P$, (2-n-$C_4H_9$—$C_6H_4)_3P$, (2-i-$C_4H_9$—$C_6H_4)_3P$, (3-n-$C_4H_9$—$C_6H_4)_3P$, (4-n-$C_4H_9$—$C_6H_4)_3P$, (2-i-$C_4H_9$—$C_6H_4)_3P$, 3-i-$C_4H_9$—$C_6H_4)_3P$, (4-i-$C_4H_9$—$C_6H_4)_3P$, (2-t-$C_4H_9$—$C_6H_4)_3P$, (3-t-$C_4H_9$—$C_6H_4)_3P$, (4-t-$C_4H_9$—$C_6H_4)_3P$, (2-$CH_3$-6-t-$C_4H_9$—$C_6H_3)_3P$, (3-$CH_3$-6-t-$C_4H_9$—$C_6H_3)_3P$, (3-$CH_3$-6-t-$C_4H_9$—$C_6H_3)_3P$, (2,6-di-t-$C_4H_9$—$C_6H_3)_3P$, (2,3-di-t-$C_4H_9$—$C_6H_3)_3P$ and (2,4-di-t-$C_4H_9$—$C_6H_3)_3P$.

Organic or inorganic compounds, atoms or ions which are coordinated onto a metal centre are designed as ligands for the ruthenium and osmium compounds to be used according to the invention.

The meanings and preferred meanings of photolabile ligands and non-photolabile ligands (also called highly coordinating ligands) have been mentioned above.

In a preferred embodiment, the Ru and Os catalysts to be used according to the invention contain only photolabile ligands, phosphine groups and anions for balancing the charge. The catalysts which contain an arene group as photolabile ligands, a tertiary phosphine group, and mono- or bivalent anions for balancing the charge are especially preferred.

Suitable anions of inorganic or organic acids are, for example, hydride ($H^\ominus$), halide (for example $F^\ominus$, $Cl^\ominus$, $Br^\ominus$ and $I^\ominus$), the anion of an oxygen acid and $BF_4^\ominus$, $PF_6^\ominus$, $SbF_6^\ominus$ or $AsF_6^\ominus$. It should be mentioned that the abovementioned cyclopentadienyl is a ligand and an anion.

Further suitable anions are $C_1$–$C_{12}$-, preferably $C_1$–$C_6$-, and particularly preferably $C_1$–$C_4$alcoholates, which, in particular, are branched, for example correspond to the formula $R_xR_yR_zC$—$O^\ominus$, in which $R_x$ is H or $C_1$–$C_{10}$alkyl, $R_y$ is $C_1$–$C_{10}$alkyl and $R_z$ is $C_1$–$C_{10}$alkyl or phenyl, and the sum of the C atoms of $R_x$, $R_y$ and $R_z$ is 11. Examples are, in particular, i-propyloxy and t-butyloxy.

Other suitable anions are $C_3$–$C_{18}$-, preferably $C_5$–$C_{14}$-, and particularly preferably $C_5$–$C_{12}$acetylides, which can correspond to the formula $R_w$—C≡C$^\ominus$, in which $R_w$ is $C_1$–$C_{16}$alkyl, preferably α-branched $C_3$–$C_{12}$alkyl, for example of the formula $R_xR_yR_zC$—, or is phenyl or benzyl which are unsubstituted or substituted by 1 to 3 $C_1$–$C_4$alkyl or $C_1$–$C_4$alkoxy. Some examples are i-propyl-, i- and t-butyl-, phenyl-, benzyl-, 2-methyl-, 2,6-dimethyl-, 2-i-propyl-, 2-i-propyl-6-methyl-, 2-t-butyl-, 2,6-di-t-butyl- and 2-methyl-6-t-butylphenylacetylide.

The meanings and preferred meanings of anions of oxygen acids have been mentioned above.

$H^\ominus$, $F^\ominus$, $Cl^\ominus$, $Br^\ominus$, $BF_4^\ominus$, $PF_6^\ominus$, $SbF_6^\ominus$, $AsF_6^\ominus$, $CF_3SO_3^\ominus$, $C_6H_5$—$SO_3^\ominus$, 4-methyl-$C_6H_5$-$SO_3^\ominus$, 2,6-dimethyl-$C_6H_5$—$SO_3^\ominus$, 2,4,6-trimethyl-$C_6H_5$—$SO_3^\ominus$ and 4-$CF_3$—$C_6H_5$—$SO_3^\ominus$ and cyclopentadienyl ($Cp^\ominus$) are particularly preferred.

The number of non-photolabile ligands depends on the number of phosphine groups, the size of the non-photolabile ligands and the number of photolabile ligands.

In a preferred embodiment, the ruthenium and osmium compounds particularly preferably correspond to one of the formulae XXIV to XXIVf $R_{97}L_1Me^{2+}(Z^{n-})_{2/n}$ (XXXIV), $R_{97}L_2L_3Me^{2+}(Z^{n-})_{2/n}$ (XXIVa), $(R_{97})_2L_2Me^{2+}(Z^{n-})_{2/n}$ (XXIVb), $(R_{97})_3L_2Me^{2+}(Z^{n-})_{2/n}$ (XXIVc), $R_{97}L_1L_2Me^{2+}(Z^{n-})_{2/n}$ (XXIVd), $R_{97}L_2L_2Me^{2+}(Zn-)_{2/n}$ (XXIVe), $R_{97}L_1L_3Me^{2+}(Z^{n-})$ (XXIVf), in which $R_{97}$ is a tertiary phosphine of the formula XXIII or XXIIIa;

Me is Ru or Os;

n is the numbers 1, 2 or 3;

Z is the anion of an inorganic or organic acid;

(a) $L_1$ is an arene or heteroarene ligand;

(b) $L_2$ is a monovalent photolabile ligand different from $L_1$; and (c) $L_3$ is a monovalent non-photolabile ligand.

For $R_{97}$, $L_8$, $L_9$ and $L_{10}$ [sic], the preferred meanings stated above for the individual meanings apply.

In the formulae XXIV to XXIVf, n is preferably 1 or 2 and especially 1. For $R_{97}$, the preferred meanings stated for the phosphine ligands of the formula XXIII apply, and in particular the phosphines are tertiary phosphines.

Ruthenium and osmium compounds which are especially preferably used in the process according to the invention are those of one of the formulae XXV to XXVf $(R_{94}R_{95}R_{96}P)L_8Me^{2+}(Z^{1-})_2$ (XXV), $(R_{94}R_{95}R_{96}P)_2L_9Me^{2+}(Z^{1-})_2$ (XXVa), $(R_{94}R_{95}R_{96}P)L_9L_{10}Me^{2+}(Z^{1-})_2$ (XXVb), $(R_{94}R_{95}R_{96}P)_3L_9Me^{2+}(Z^{1-})_2$ (XXVc), $(R_{94}R_{95}R_{96}P)L_9L_9Me^{2+}(Z^{1-})_2$ (XXVd), $(R_{94}R_{95}R_{96}P)L_8L_{10}Me^{2+}(Z^{1-})_2$ (XXVe), $(R_{94}R_{95}R_{96}P)L_8(L_9)_mMe^{2+}(Z^{1-})_2$ (XXVf)

n which

Me is Ru or Os;

Z in formulae XXV to XXVe is $H^\ominus$, cyclopentadienyl, $Cl^\ominus$, $Br^\ominus$, $BF_4^\ominus$, $PF_6^\ominus$, $SbF_6^\ominus$, $AsF_6^\ominus$, $CF_3SO_3^\ominus$, $C_6H_5$—$SO_3^\ominus$, 4-methyl-$C_6H_5$—$SO_3^\ominus$, 3,5-dimethyl-$C_6H_5$—$SO_3^\ominus$, 2,4,6-trimethyl-$C_6H_5$—$SO_3^\ominus$ and 4-$CF_3$—$C_6H_5$—$SO_3^\ominus$ and in formula XXVf is $H^\ominus$, cyclopentadienyl, $BF_4^\ominus$, $PF_6^\ominus$, $SbF_6^\ominus$, $AsF_6^\ominus$, $CF_3SO_3^\ominus$, $C_6H_5$—$SO_3^\ominus$, 4-methyl-$C_6H_5$—$SO_3^\ominus$, 2,6-dimethyl-$C_6H_5$—$SO_3^\ominus$, 2,4,6-trimethyl-$C_6H_5$—$SO_3^\ominus$ or 4-$CF_3$—$C_6H_5$—$SO_3^\ominus$, $R_{94}$, $R_{95}$ and $R_{96}$ independently of one another are $C_1$–$C_6$alkyl or -alkoxy, cyclopentyl or cyclohexyl or cyclopentyloxy or cyclohexyloxy which are unsubstituted or substituted by 1 to 3 $C_1$–$C_4$alkyl, or phenyl or benzyl or phenyloxy or benzyloxy which are unsubstituted or substituted by 1 to 3 $C_1$–$C_4$alkyl;

$L_8$ is $C_6$–$C_{16}$arene or $C_5$–$C_{16}$heteroarene which are unsubstituted or substituted by 1 to 3 $C_1$–$C_4$alkyl, $C_1$–$C_4$alkoxy, —OH, —F or Cl;

$L_9$ is $C_1$–$C_6$alkyl-CN, benzonitrile or benzylnitrile; and $L_{10}$ is $H_2O$ or $C_1$–$C_6$alkanol.

Preferred arenes and heteroarenes are benzene, toluene, xylene, trimethylbenzene, naphthalene, biphenyl, anthracene, acenaphthene, fluorene, phenanthrene, pyrene, chrysene, fluoranthrene, furan, thiophene, pyrrole, pyridine, γ-pyran, γ-thiopyran, pyrimidine, pyrazine, indole, coumarone, thionaphthene, carbazole, dibenzofuran, dibenzothiophene, pyrazole, imidazole, benzimidazole, oxazole, thiazole, isoxazole, isothiazole, quinoline, isoquinoline, acridine, chromene, phenazine, phenoxazine, phenothiazine, triazines, thianthrene and purine. More preferred arenes and heteroarenes are benzene, naphthalene, cumene, thiophene and benzothiophene. The arene is especially preferably benzene or a benzene which is substituted by $C_1$–$C_4$alkyl, such as, for example, toluene, xylene, isopropylbenzene, tert-butylbenzene or cumene, and the heteroarene is preferably thiophene.

If the preparation of the ruthenium and osmium catalysts is carried out in solvents which can coordinate to a metal atom, such as, for example, alkanols, solvated Ru/Os cation complexes which are also included in the scope of the use according to the invention can form.

Some examples of ruthenium and osmium compounds to be used according to the invention are [Tos is tosylate]: $(C_6H_{11})_2HPRu(p\text{-cumene})Cl_2$, $(C_6H_{11})_3PRu(p\text{-cumene})Cl_2$, $(C_6H_{11})_3PRu(p\text{-cumene})(Tos)_2$, $(C_6H_{11})_3PRu(p\text{-cumene})Br_2$, $(C_6H_{11})_3PRu(p\text{-cumene})ClF$, $(C_6H_{11})_3PRu(C_6H_6)(Tos)_2$, $(C_6H_{11})_3PRu(CH_3\text{—}C_6H_5)(Tos)_2$, $(C_6H_{11})_3PRu(i\text{-}C_3H_7\text{—}C_6H_5)(Tos)_2$, $(C_6H_{11})_3PRu(\text{chrysene})(Tos)_2$, $(C_6H_{11})_3PRu(\text{biphenyl})(Tos)_2$, $(C_6H_{11})_3PRu(\text{anthracene})(Tos)_2$, $(C_6H_{11})_3PRu(C_{10}H_8)(Tos)_2$, $(i\text{-}C_3H_7)_3PRu(p\text{-cumene})Cl_2$, $(CH_3)_3PRu(p\text{-cumene})Cl_2$, $(n\text{-}C_4H_9)_3PRu(p\text{-cumene})Cl_2$, $[(C_6H_{11})_3P]_2RuCH_3\text{-CN)(Tos)}_2$, $(C_6H_{11})_3PRu(CH_3\text{-CN})(C_2H_5\text{-OH})(Tos)_2$, $(C_6H_{11})_3PRu(p\text{-cumene})(CH_3\text{-CN})_2(PF_6)_2$, $(C_6H_{11})_3PRu(p\text{-cumene})(CH_3\text{-CN})_2(Tos)_2$, $(n\text{-}C_4H_9)_3PRu(p\text{-cumene})(CH_3\text{-CN})_2(Tos)_2$, $(C_6H_{11})_3PRu(CH_3\text{-CN})_2Cl_2$, $(C_6H_{11})_3PRu(CH_3\text{-CN})_2Cl_2$, $(C_6H_{11})_3PRu(p\text{-cumene})(C_2H_5OH(BF_4))_2$, $(C_6H_{11})_3PRu(p\text{-cumene})(C_2H_5OH(BF_4))_2$, $(C_6H_{11})_3PRu(p\text{-cumene})(C_2H_5OH_2(PF_6))_2$, $(C_6H_{11})_3Pru(C_6H_{11})(C_2H_5OH$ (Tos)$_2$, (C$_6$H$_{11}$)$_3$POs(p-cumene)Cl$_2$, (i-C$_3$H$_7$)$_3$POs(p-cumene)Cl$_2$, (CH$_3$)$_3$POs(p-cumene)Cl$_2$, (C$_6$H$_5$)$_3$POs(p-cumene)Cl$_2$ and RuCl$_2$(p-cumene)[(C$_6$H$_{11}$)$_2$PCH$_2$CH$_2$P(C$_6$H$_{11}$)$_2$].

The ruthenium and osmium compounds to be used according to the invention are known or can be prepared by known and analogous processes starting from the metal halides (for example MeX$_3$ or [Me-areneX$_2$]$_2$ and reaction with phosphines and ligand-forming agents.

7. Other suitable one-component catalysts are divalent-cationic ruthenium or osmium compounds with a metal atom to which are bonded, acts [sic], 1 to 3 tertiary phosphine ligands with, in the case of the ruthenium compounds, sterically exacting substituents, optionally non-photolabile neutral ligands and anions for charge balancing, with the proviso that in ruthenium (trisphenylphosphine) dihalides or hydride-halides, the phenyl groups are substituted by C$_1$–C$_{18}$alkyl, C$_1$–C$_{18}$haloalkyl or C$_1$–C$_{18}$alkoxy.

The ruthenium and osmium compounds preferably contain 2 or 3 tertiary phosphine groups. Phosphine groups in the context of the invention are understood as meaning tertiary phosphines. The number of additional non-photolabile neutral ligands depends on the one hand on the number of phosphine ligands and on the other hand on the valency of the neutral ligands. Monovalent neutral ligands are preferred.

In a preferred embodiment, the divalent-cationic ruthenium and osmium compounds to be used according to the invention contain 3 phosphine groups and 2 monovalent anions for charge balancing; or 3 phosphine groups, two monovalent or one divalent non-photolabile neutral ligand and two monovalent anions for charge balancing; or 2 phosphine groups, one monoanionic, additionally monovalent non-photolabile neutral ligands and one monovalent anion for charge balancing.

The meanings and preferred meanings of non-photolabile ligands (also called highly coordinating ligands) have been mentioned above.

Sterically exacting substituents in the context of the invention are understood as meaning those which shield the ruthenium and osmium atoms sterically. It has thus been found, surprisingly, that linear alkyl groups as substituents in the phosphine ligands give ruthenium compounds without any thermal activity for metathesis polymerization of strained cycloolefins. It has also been found that in the case of osmium compounds, linear alkyl groups as substituents in the phosphine ligands surprisingly have an excellent thermocatalytic activity for the metathesis polymerization of strained cycloolefins; however, phosphine ligands with sterically exacting substituents are also preferably used for the osmium compounds. It has furthermore been found that the steric shielding of triphenylphosphine ligands is inadequate in ruthenium dihalides and ruthenium hydride-halides, and such catalysts have only a moderate catalytic activity for the metathesis polymerization of strained cycloolefins. Surprisingly, the catalytic activity can be increased considerably if the tertiary phosphine groups contain phenyl which is substituted by alkyl or alkoxy groups.

The meanings and preferred meanings of phosphine ligands have been mentioned above. With particular preference, alkyl R$_{91}$, R$_{92}$ and R$_{93}$ are α-branched alkyl, for example of the formula —CR$_b$R$_c$R$_d$, in which R$_b$ is H or C$_1$–C$_{12}$alkyl, R$_c$ is C$_1$–C$_{12}$alkyl and R$_d$ is C$_1$–C$_{12}$alkyl or unsubstituted or C$_1$–C$_4$alkyl- or C$_1$–C$_4$alkoxy-substituted phenyl, and the sum of the C atoms in the radical —CR$_b$R$_c$R$_d$ is from 3 to 18.

In the osmium compounds used, R$_{91}$, R$_{92}$ and R$_{93}$ can also be linear alkyl having 1 to 18, preferably 1 to 12, more preferably 1 to 8, and particularly preferably 1 to 6 C atoms, for example, methyl, ethyl, n-propyl, n-butyl, n-pentyl, n-hexyl, n-heptyl and n-octyl.

In a preferred embodiment, the phosphine ligands correspond to the formula XXIII, in which R$_{91}$, R$_{92}$ and R$_{93}$ independently of one another are α-branched C$_3$–C$_8$alkyl, cyclopentyl or cyclohexyl which are unsubstituted or substituted by C$_1$–C$_4$alkyl, or phenyl which is unsubstituted or substituted by C$_1$–C$_4$alkyl, C$_1$–C$_4$alkyl [sic] C$_1$–C$_4$alkoxy or trifluoromethyl. Particularly preferred examples of phosphine ligands of the formula XXIII are (C$_6$H$_5$)$_3$P, (C$_5$H$_9$)$_3$P, (i-C$_3$H$_7$)$_3$P, (C$_6$H$_{11}$)3P, (i-C$_4$H$_9$)$_3$P, (t-C$_4$H$_9$)$_3$P, [C$_2$H$_5$CH(CH$_3$)]$_3$P, [C$_2$H$_5$-CH(CH$_3$)$_2$]$_3$P, (2-methylphenyl)$_3$P, (2,3-dimethylphenyl)$_3$P, (2,4-dimethylphenyl)$_3$P, (2,6-dimethylphenyl)$_3$P, (2-methyl-4-i-propylphenyl)$_3$P, (2-methyl-3-i-propylphenyl)$_3$P, (2-methyl-5-i-propylphenyl)$_3$P, (2,4-di-t-butylphenyl)$_3$P, (2-methyl-6-i-propylphenyl)$_3$P, (2-methyl-3-t-butylphenyl)$_3$P, (2,5-di-t-butylphenyl)$_3$P, (2-methyl4-t-butylphenyl)$_3$P, (2-methyl-5-i-butylphenyl)$_3$P, (2,3-di-t-butylphenyl)$_3$P and (2,6-di-t-butylphenyl)$_3$P.

Examples of and preferred meanings for suitable anions have been mentioned above.

In a preferred embodiment, the ruthenium and osmium compounds particularly preferably correspond to the formulae XXVI, XXVIa, XXVIb, XXVIc and XXVId

   (XXVI)

   (XXVIa)

   (XXVIb)

   (XXVIc)

   (XXVId)

in which

Me is Ru or Os;

Y$_1$ is the anion of a monobasic acid;

L$_{11}$ is a phosphine of the formula XXIII or XXIIIa,

L$_{12}$ is a neutral ligand;

L$_{13}$ is a cyclopentadienyl which is unsubstituted or substituted by C$_1$–C$_4$alkyl; and L$_{14}$ is CO.

The above preferred meanings apply to the individual meanings of L$_{11}$, L$_{12}$, L$_{13}$ and Y$_1$.

In a particularly preferred embodiment, L$_{12}$ in formula XXVI is a C$_1$–C$_4$alkanol, Y$_1$ in formula XXVIb is Cl or Br, Y$_1$ in formula XXVIc is H, and L$_{11}$ in the formulae XXVI to XXVIc is tri-i-propylphosphine, tricyclohexylphosphine, triphenylphosphine or triphenylphosphine which is substituted by 1 to 3 C$_1$–C$_4$alkyl in the phenyl groups.

The ruthenium and osmium compounds to be used according to the invention are known or can be prepared by known and analogous processes starting from the metal halides (for example MeX$_3$, [Me(diolefin)X$_2$]$_2$ or [Me-areneX$_2$]$_2$ and reaction with phosphines and agents which form ligands.

The composition according to the invention can additionally comprise other open-chain, strained cyclic and/or strained polycyclic fused olefins which form metathesis polymers, these olefins preferably also containing further double bonds and contributing to the formation of crosslinked polymers. The cyclic olefins can be monocyclic or polycyclic fused ring systems, for example with 2 to 4 rings, which are unsubstituted or substituted and can contain heteroatoms, such as, for example, O, S, N or Si, in one or more rings and/or fused aromatic or heteroaromatic rings, such as, for example, o-phenylene, o-naphthylene, o-pyridinylene or o-pyrimidinylene. The individual cyclic rings can contain 3 to 16, preferably 3 to 12, and particularly preferably 3 to 8 ring members. The cyclic olefins can contain further nonaromatic double bonds, preferably 2 to 4 such additional double bonds, depending on the ring size. The ring substituents are those which are inert, that is to say do not impair the chemical stability of the one-component catalysts. A large number of such olefins and cycloolefins are known, and they are obtainable in a simple manner by Diels-Alder reactions of cyclodienes and cycloolefins or polycyclic or polycyclic fused olefins. These cycloolefins can correspond, for example, to the formula IIa

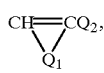
(IIa)

in which $Q_1$ and $Q_2$ have the meanings given for radicals of the formula II, including the preferred meanings.

Some preferred examples of compounds of the formula IIa are norbornene and norbornene derivatives. Specific examples are:

(25)

(26)

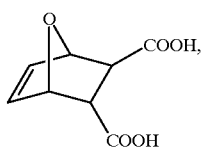
(27)

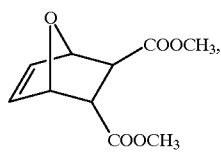
(28)

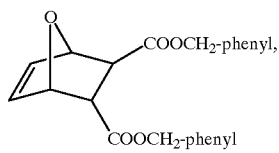
(29)

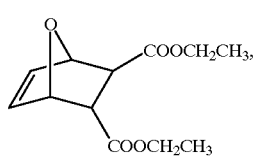

-continued

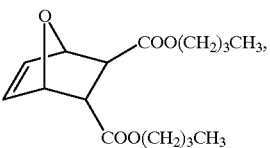
(30)

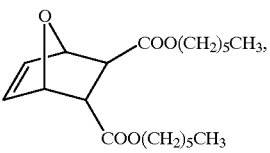
(31)

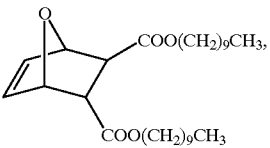
(32)

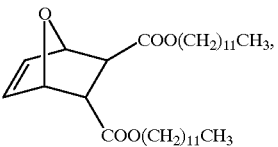
(33)

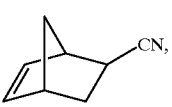
(34)

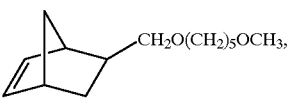
(35)

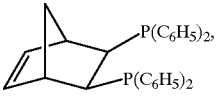
(36)

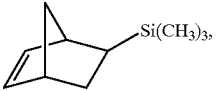
(37)

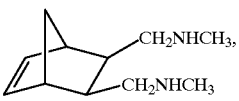
(38)

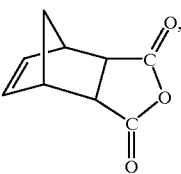
(39)

(40) 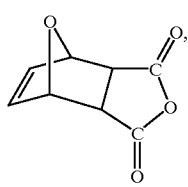
(41) 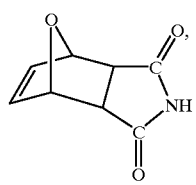
(42) 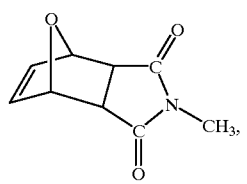
(43) 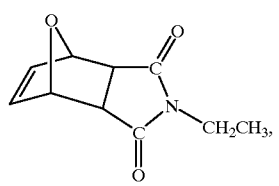
(44) 
(45) 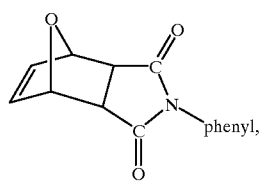
(46) 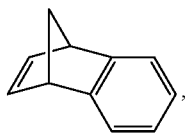
(47) 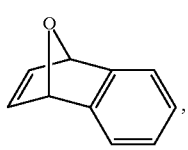
(48) 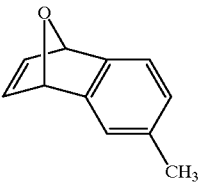
(49) 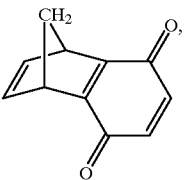
(50) 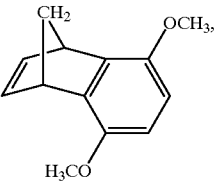
(51) 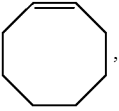
(52) 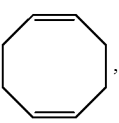
(53) 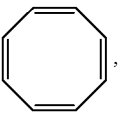
(54) 
(55) 
(56) 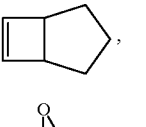

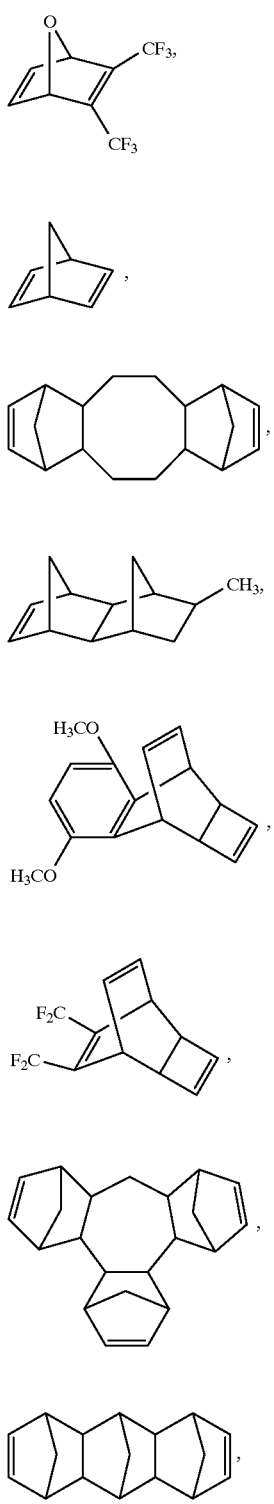

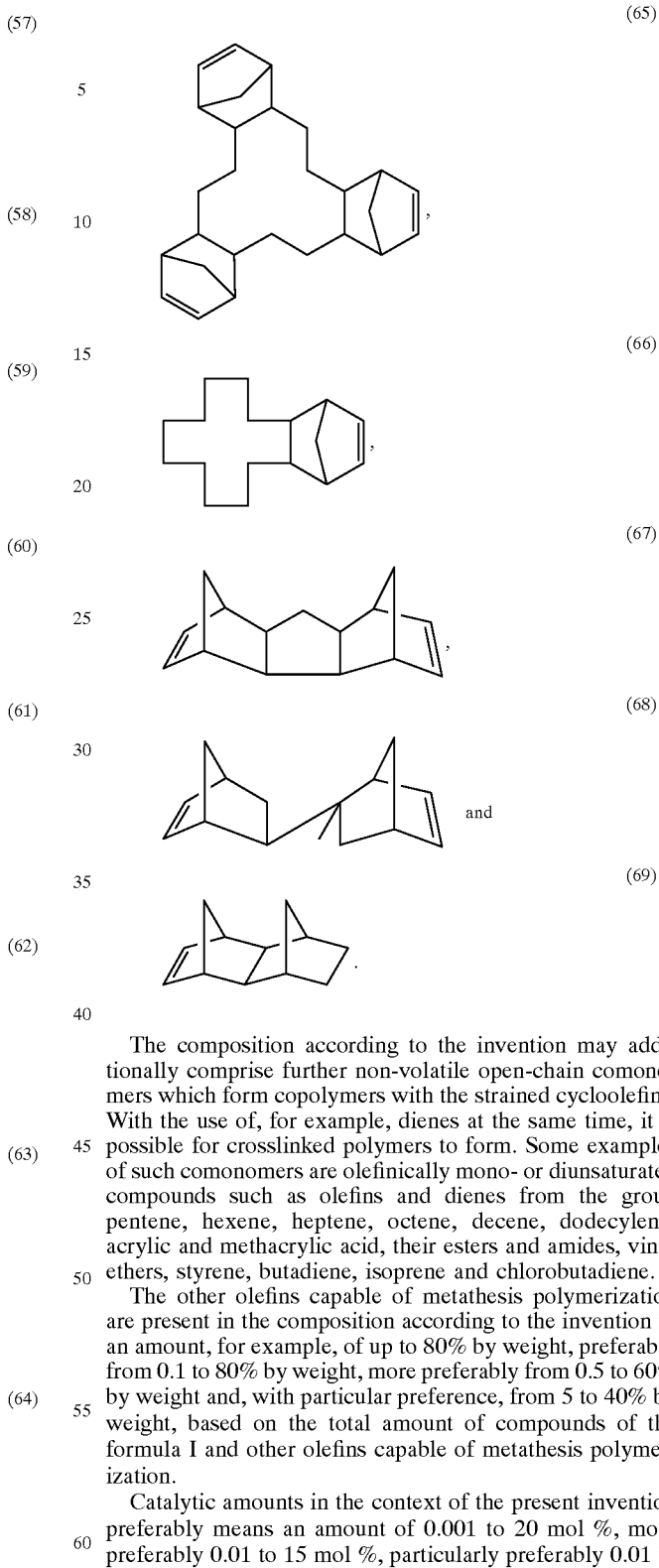

The composition according to the invention may additionally comprise further non-volatile open-chain comonomers which form copolymers with the strained cycloolefins. With the use of, for example, dienes at the same time, it is possible for crosslinked polymers to form. Some examples of such comonomers are olefinically mono- or diunsaturated compounds such as olefins and dienes from the group pentene, hexene, heptene, octene, decene, dodecylene, acrylic and methacrylic acid, their esters and amides, vinyl ethers, styrene, butadiene, isoprene and chlorobutadiene.

The other olefins capable of metathesis polymerization are present in the composition according to the invention in an amount, for example, of up to 80% by weight, preferably from 0.1 to 80% by weight, more preferably from 0.5 to 60% by weight and, with particular preference, from 5 to 40% by weight, based on the total amount of compounds of the formula I and other olefins capable of metathesis polymerization.

Catalytic amounts in the context of the present invention preferably means an amount of 0.001 to 20 mol %, more preferably 0.01 to 15 mol %, particularly preferably 0.01 to 10 mol %, and especially preferably 0.01 to 5 mol %, based on the amount of the monomer. Because of the high photocatalytic activity of ruthenium and osmium catalysts containing phosphine groups, amounts of 0.001 to 2 % by weight are especially preferred in this case.

The composition according to the invention can comprise solvents, especially if they are [sic] used for the production of coatings.

Suitable inert solvents are, for example, protic polar and aprotic solvents, which can be used by themselves or in mixtures of at least two solvents. Examples are: ethers (dibutyl ether, tetrahydrofuran, dioxane, ethylene glycol monomethyl or dimethyl ether, ethylene glycol monoethyl or diethyl ether, diethylene glycol diethyl ether, triethylene glycol dimethyl ether), halogenated hydrocarbons (methylene chloride, chloroform, 1,2-dichloroethane, 1,1,1-trichloroethane, 1,1,2,2-tetrachloroethane), carboxylic acid esters and lactones (ethyl acetate, methyl propionate, ethyl benzoate, 2-methoxyethyl acetate, γ-butyrolactone, δ-valerolactone, pivalolactone), carboxylic acid amides and lactams (N,N-dimethylformamide, N,N-diethylformamide, N,N-dimethylacetamide, tetramethylurea, hexamethylphosphoric acid triamide, γ-butyrolactam, ε-caprolactam, N-methylpyrrolidone, N-acetylpyrrolidone, N-methylcaprolactam), sulfoxides (dimethyl sulfoxide), sulfones (dimethyl sulfone, diethyl sulfone, trimethylene sulfone, tetramethylene sulfone), tertiary amines (N-methylpiperidine, N-methylmorpholine), aliphatic and aromatic hydrocarbons, such as, for example, petroleum ether, pentane, hexane, cyclohexane, methylcyclohexane, benzene or substituted benzenes (chlorobenzene, o-dichlorobenzene, 1,2,4-trichlorobenzene, nitrobenzene, toluene, xylene) and nitriles (acetonitrile, propionitrile, benzonitrile, phenylacetonitrile). Preferred solvents are aprotic polar and non-polar solvents.

The choice of solvents depends chiefly on the properties of the one-component catalysts, which should not be deactivated by the solvents used. Ruthenium and osmium catalysts can be used together with polar protic solvents, such as, for example, water or alkanols. These catalysts are also insensitive to air, oxygen and moisture, and corresponding crosslinkable compositions can be processed without particular protective measures. In the case of the other one-component catalysts, the exclusion of oxygen and moisture is advisable. The compositions are storage-stable, storage in the dark being advisable because of the sensitivity to light. The composition according to the invention can comprise formulation auxiliaries. Known auxiliaries are antistatics, antioxidants, light stabilizers, plasticizers, dyes, pigments, fillers, reinforcing fillers, lubricants, adhesion promoters, viscosity-increasing agents and mould release auxiliaries. The fillers can be present in surprisingly high proportions without adversely affecting the polymerization, for example in amounts of up to 70% by weight, preferably from 1 to 70% by weight, more preferably from 5 to 60% by weight, with particular preference from 10 to 50% by weight and, especially preferably, from 10 to 40% by weight, based on the composition. Fillers and reinforcing fillers for improving the optical, physical, mechanical and electrical properties have been disclosed in large numbers. Some examples are glass and quartz in the form of powders, spheres and fibres, metal oxides and semi-metal oxides, carbonates such as $MgCO_3$, $CaCO_3$, dolomite, metal sulfates such as gypsum and heavy spar, natural and synthetic silicates such as talc, zeolites, wollastonite, felspars, aluminas such as china clay, ground minerals, whiskers, carbon fibres, polymer fibres or polymer powders, and carbon black. Viscosity-increasing agents are, in particular, metathesis polymers which have olefinically unsaturated groups and can be incorporated into the polymer in the course of polymerization. Such metathesis polymers are known and are obtainable commercially, for example, under the trade name Vestenamere®. Other viscosity-increasing agents are polybutadiene, polyisoprene or polychlorobutadiene, and also copolymers of butadiene, isoprene and chloroprene with olefins. The viscosity-increasing agents can be present in an amount of from 0.1 to 50% by weight, preferably from 1 to 30% by weight, and with particular preference, from 1 to 20% by weight based on the composition. When fillers are used it is judicious to obtain optical transparency for the polymerization or to carry out the polymerization in thin layers.

The invention also relates to a process for the preparation of crosslinked polymers by metathesis polymerization, which is characterized in that a composition of (a) at least one compound of the formula I $$(A)_n\text{---}B \qquad\qquad (I),$$ 

in which A is the radical of a strained cycloolefin, B is a direct bond or an n-valent bridging group and n is an integer from 2 to 8, and (b) a catalytic amount of at least one one-component catalyst for a metathesis polymerization which can be activated by heat or radiation, with the exception of norbornenecarboxylic acid (norbornenemethyl) ester of the formula

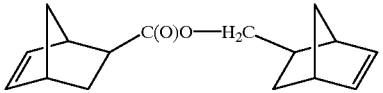

in combination with a catalytic amount of at least one heat-stable molybdenum(VI) or tungsten(VI) compound which contains at least two methyl groups or two monosubstituted methyl groups bonded to the metal, the substituent containing no hydrogen atom in the α position, (c) is subjected to polymerization by heating, (d) is subjected to polymerization by irradiation, (e) is subjected to polymerization by heating and irradiation, (f) the one-component catalyst is activated by brief heating and the polymerization is ended by irradiation, or (g) the one-component catalyst is activated by brief irradiation and the polymerization is ended by heating.

Heating can mean a temperature of 50 to 300° C., preferably 60 to 250° C., particularly preferably 60 to 200° C., and especially preferably 60 to 150° C. The polymerization times especially depend on the catalyst activity, and the time can extend from minutes to several hours.

In the process according to the invention, it is not necessary to maintain the irradiation of the reaction mixture over the entire duration of the reaction. Once the polymerization has been initiated photochemically, the subsequent course of the reaction takes place independently, even in the dark. The irradiation is advantageously carried out with light having a wavelength in the range from 50 nm to 1000 nm, preferably in the range from 200 nm to 500 nm and especially preferably in the UV range. The duration of the irradiation depends on the nature of the light source. Suitable sources of irradiation are, for example, the sun; laser, X-ray and, in particular, UV radiation sources. UV lasers or UV lamps are preferably employed according to the invention. The catalyst can be irradiated both before or during as well as after addition of the monomer.

Suitable irradiation times are from one second to several hours, in particular minutes to hours. The sequence of addition of monomers and catalyst is not critical. The monomer can be both initially introduced into the reaction vessel and added after introduction of catalyst. Likewise, the catalyst can be pre-irradiated and the monomer can then be added. It is furthermore also possible to irradiate the solution comprising catalyst and monomer.

In the case of irradiation, the process according to the invention is preferably carried out at room temperature to slightly elevated temperature. An increase in temperature serves to increase the rate of reaction. The catalysts used initiate thermal metathesis polymerization per se, with crosslinking, at the temperatures chosen only in exceptional cases. At the temperatures chosen to accelerate the reaction, photopolymerization therefore chiefly takes place. However, it should be mentioned that the catalysts can be converted into thermoactive catalysts by adequate irradiation.

In particular, the process according to the invention is carried out with irradiation preferably at temperatures of −20 to +110° C., particularly preferably 20 to 80° C.

The duration of irradiation especially depends on the desired reaction procedure. Brief irradiation is chosen, for example, if the polymerization is to be only initiated by irradiation and is to be ended by heating. Brief can mean an irradiation time of up to 60 seconds, preferably 5 to 60 seconds, and particularly preferably 10 to 40 seconds. A longer irradiation time is chosen, for example, if the polymerization is to be carried out chiefly with irradiation and the final polymerization is to be ended only by after-heating.

A quite particular and surprising advantage of the process according to the invention is that the one-component catalysts used act as thermal catalysts after the irradiation. This results in the possibility of continuing and ending the polymerization by supplying heat after a short irradiation time, which offers economic and industrial advantages in various areas of the production of shaped articles or coatings.

The present invention furthermore relates to crosslinked metathesis polymers of at least one compound of the formula I

$(A)_n$—B  (I)

in which A is the radical of a strained cycloolefin, B is a direct bond or an n-valent bridging group and n is an integer from 2 to 8, and if appropriate other monomers capable of metathesis polymerization, with the exception of norbornenecarboxylic acid norbornenemethyl ester.

Materials for production of shaped articles by machining, or, directly, all types of shaped articles, as well as coatings and images in relief, can be produced by the process according to the invention.

The polymers according to the invention can have very different properties, depending on the monomer used. Some are distinguished by a very high permeability to oxygen, low dielectric constants, good heat stability and low absorption of water. Others have outstanding optical properties, such as, for example, high transparency and low refractive indices. The low shrinkage is furthermore to be emphasized in particular. They can therefore be used in very different industrial fields.

As layers on the surfaces of carrier materials, the compositions according to the invention are distinguished by a high adhesive strength. The coated materials are furthermore distinguished by a very high surface smoothness and gloss. Of the good mechanical properties, the low shrinkage and the high impact strength are to be emphasized in particular, as well as the heat stability. Easy removal from the mould during processing in moulds and the high resistance to solvents are furthermore to be mentioned.

These polymers are suitable for the production of medical equipment, implants or contact lenses; for the production of electronic components; as binders for coatings; as photocurable compositions for model construction or as adhesives for gluing substrates with low surface energies (for example Teflon, polyethylene and polypropylene), as well as a photopolymerizable composition in stereolithography. The compositions according to the invention can also be used for the production of coatings by photopolymerization, it being possible on the one hand for clear (transparent) and even pigmented compositions to be used. Both white and colored pigments can be used.

The compositions according to the invention are particularly suitable for the production of protective coatings and images in relief. The invention also relates to a variant of the process according to the invention for the production of coated materials or relief images on carrier materials in which a composition according to the invention and optionally solvent is applied as a layer to a carrier, for example by dipping, brushing, pouring, rolling, knife-coating or whirler pouring processes, the solvent is removed, if appropriate, and the layer is irradiated or heated for polymerization, or the layer is irradiated through a photomask and the non-irradiated portions are then removed with a solvent. This can be followed by thermal conditioning. Surfaces of substrates can be modified or protected by this process, or, for example, printed circuits, printing plates or printing rolls can be produced. In the production of printed circuits, the compositions according to the invention can also be employed as solder resists. Other possible uses are the production of screen printing masks and the use as radiation-curable printing inks for offset, screen and flexographic printing.

The present invention furthermore relates to a coated carrier material, which is characterized in that a layer of a composition according to the invention is applied to a substrate.

The present invention also relates to a coated substrate with a cured layer of a composition according to the invention. The exceptionally high adhesive strength of the layers, even on metal surfaces, deserves particular emphasis, even if the polymers are pure hydrocarbon polymers.

Suitable carrier materials are, for example, those of glass, minerals, ceramics, plastics, wood, semi-metals, metals, metal oxides and metal nitrides. The layer thicknesses essentially depend on the desired use and can be, for example, 0.1 to 1000 μm, preferably 0.5 to 500 μm, particularly preferably 1 to 100 μm. The coated materials are distinguished by a high adhesive strength and good thermal and mechanical properties.

The production of the coated materials according to the invention can be carried out by known methods, such as, for example, brushing, knife-coating, pouring processes, such as curtain coating or whirler pouring.

The compositions according to the invention are also suitable for the preparation of rubber-like or thermoplastic polymers, which can be crosslinked still further if they contain reactive groups, such as, for example, (meth) acrylate or epoxide groups.

The compositions according to the invention can also be used as adhesives, which can be cured by heat or by means of radiation, for firmly joining the most diverse materials, it being possible for outstanding peel strength to be achieved.

The polymers according to the invention are in particular also distinguished by very good physico-mechanical properties, such as, for example, high heat stability, breaking and flexural strength and impact strength and outstanding electrical properties, such as, for example, low surface tensions and charges (very low $\epsilon$ and tan $\delta$ values), in addition to the high adhesive strength, the outstanding processing properties, the good surface properties (smoothness, gloss), the high crosslinking density and the resistance to solvents and other liquids. The high permeability to oxygen and the low absorption of water are furthermore to be mentioned. Polymers built up only from carbon and hydrogen are particularly valuable ecologically, since they can be recycled completely, for example by pyrrolysis [sic].

The following examples illustrate the invention in more detail.

A) Preparation of Biscycloolefins

EXAMPLE A1
Preparation of Compound No. 0 (see EP 287,762).

70 g (0.86 mol) of 1,5-hexadiene and 56 g (0.42 mol) of dicyclopentadiene are mixed in an autoclave and the mixture is heated at 190° C. for 8 hours. After cooling, the mixture is distilled in vacuo. 32.6 g (36%) of product are obtained as a colourless liquid at 80 to 110° C. under 0.28 to 0.30 mbar; $n_D^{20}=1.525$.

Elemental analysis: calculated C 89.65; H 10.35; found C 89.72; H 10.13.

EXAMPLE A2
Preparation of Compound No.2.

35 g (0.32 mol) 1,7-octadiene and 28 g (0.21 mol) of dicyclopentadiene are mixed in an autoclave and the mixture is heated at 190° C. for 8 hours. After cooling, the mixture is distilled in vacuo. 6.7 g (13%) of product are obtained as a colourless liquid at 100° C. under 0.21 mbar; $n_D^{20}=1.516$.

Elemental analysis: calculated C 89.19; H 10.81; found C 89.50; H 10.60.

EXAMPLE A3
Preparation of Compound No.3.

34.6 g (0.25 mol) of 1,5-decadiene and 33.1 g (0.25 mol) of dicyclopentadiene are mixed in an autoclave and the mixture is heated at 190° C. for 8 hours. After cooling, the mixture is distilled in vacuo. 11.4 g (17%) of product are obtained as a colourless liquid at 80 to 100° C. under 0.24 mbar; $n_D^{20}=1.504$, the liquid becoming solid at room temperature.

Elemental analysis: calculated C 88.82; H 11.18; found C 88.62; H 11.18.

EXAMPLE A4
Preparation of Compound No. 20

99.7 g (0.40 mol) of triallyl cyanurate and 79.3 g (0.6 mol) of dicyclopentadiene are mixed in an autoclave and the mixture is heated at 190° C. for 8 hours. After cooling, 160 g (89.4%) of a brownish resinous solid having a melting point of of [sic] 50° C., which is soluble in toluene and chloroform, are obtained.

Elemental analysis: calculated C 72.46; H 7.43; N 9.39. found C 72.21; H 7.52; N 9.32.

A') Preparation of Comonomers

EXAMPLE A'1
Preparation of Compound No.59

100 g (0.92 mol) of 1,5-cyclooctadiene and 200 g (1.51 mol) of dicyclopentadiene are mixed together with 0.4 g of hydrquinone [sic] monomethyl ether in an autoclave and the mixture is heated at 190° C. for 3 hours. After cooling, it is distilled in vacuo. 73.5 9 (33%) of product are obtained as a colourless liquid at 110° C. under 4.6 mbar; $n_D^{20}=1.534$. MS: M$^+$=240.

Elemental analysis: calculated C 89.92; H 10.08; found C 90.11; H 9.04.

EXAMPLE A'2
Preparation of Compound No.65

64.9 g (0.40 mol) of 1,5,9-cyclododecatriene and 79.3 g (0.60 mol) of dicyclopentadiene are mixed in an autoclave and the mixture is heated at 190° C. for 8 hours. After cooling, it is distilled in vacuo. 22.6 g (16%) of product are obtained as a colourless liquid at 50 to 60° C. under 0.04 mbar; $n_D^{20}=1.541$. MS: M$^+$=360.

Elemental analysis: calculated C 89.94; H 10.06; found C 89.96; H 9.90.

EXAMPLE A'3
Preparation of Compound No.63

92.1 g (1.00 mol) of cycloheptatriene and 198.3 g (1.50 mol) of dicyclopentadiene are mixed in an autoclave and the mixture is heated at 190° C. for 8 hours. After cooling, it is distilled in vacuo. 80.6 g (28%) of product are obtained as a colourless liquid at 75° C. under 0.12 mbar; $n_D^{20}=1.542$. MS: M$^+$=290.

Elemental analysis: calculated C 90.98; H 9.02; found C 90.71; H 9.31.

EXAMPLE A'4
Preparation of Compound No. 64

100 g (1.09 mol) of norbornadiene and 50 g (0.38 mol) of dicyclopentadiene are mixed together with 0.2 g of hydroquinone monomethyl ether in an autoclave and the mixture is heated at 190° C. for 3 hours. After cooling, it is distilled in vacuo. 25.0 g (29%) of product are obtained as a colourless liquid at 35° C. under 0.25 mbar; $n_D^{20}=1.532$. MS: M$^+$=224.

Elemental analysis: calculated C 91.01; H 8.99; found C 90.94; H 9.01.

EXAMPLE A'5
Preparation of Compound No.66

80.2 g (0.50 mol) of cyclododecene and 33.05 g (0.25 mol) of dicyclopentadiene are mixed in an autoclave and the mixture is heated at 190° C. for 8 hours. After cooling, it is distilled in vacuo. 8.10 g (7%) of product are obtained as a colourless liquid at 61° C. under 0.12 mbar; $n_D^{20}=1.528$. MS: M$^+$=232.

Elemental analysis: calculated C 87.86; H 12.14; found C 87.98; H 11.72.

EXAMPLE A'6
Preparation of Compound No. 68

104.25 g (1.5 mol) of isoprene (98%), 208.7 g (1.5 mol) of dicyclopentadiene (95%) and 1.0 g of tert-butylpyrocatechol are mixed and the mixture is heated at 200° C. for 8 h under $N_2$ with stirring in an autoclave. After cooling, the semisolid mass is distilled under a high vacuum. Boiling point: 60° C. (0.07 mbar). Yield: 202.4 g (67.4%). $n_D^{20}=1.53$ Elemental analysis: calculated C 89.94; H 10.06 found C 89.85; H 10.08

EXAMPLE A'7
Preparation of Compound No. 69

139.2 g (1.0 mol) of dicyclopentadiene (95%), 194.2 g (2.0 mol) of 2-norbornene (97%) and 3.0 g of tert-butylpyrocatechol are mixed and the mixture is heated at 230° C. for 2 h under N₂ with stirring in an autoclave. After cooling, the semisolid mass is distilled under a high vacuum. Boiling point: 65° C. (0.065 mbar). Yield: 69.0 9 (21.5%). $n_D^{20}$=1.54

Elemental analysis: calculated C 89.93; H 10.07 found C 90.07; H 9.88

B) Preparation of Crosslinked Polymers.

The catalysts used are:

A) W(=NC₆H₅)[OC(CH₃)₃]₂[CH₂Si((CH₃)₃]₂Cl
B) W(=NC₆H₅)[OCCH₃(CF₃)₂]₂[CH₂Si((CH₃)₃]₂
C) RuCl₂(p-cumene)P(C₆H₁₁)₃

EXAMPLE B1

The compound according to Example A1 is mixed with 0.7% by weight of catalyst A and the mixture is poured into a glass mould. It is then irradiated at room temperature in a UV oven for 30 minutes (4 tubes of 100 W output) and then subjected to thermal polymerization at 80° C. for 1 hour. A dimensionally stable sheet, $T_g$ 75° C. (determined by means of differential scanning calorimetry) is obtained. The polymer swells in toluene without dissolving. The low degree of swelling of 44% indicates a high crosslinking density.

EXAMPLE B2

The mixture according to Example B1 is irradiated only with a 200 W mercury medium-pressure vapour lamp. A dimensionally stable sheet, $T_g$ 60° C., is obtained. The degree of swelling in toluene is 54%.

EXAMPLE B3

The procedure is as in Example B1, but with 1% by weight of catalyst and an additional thermal after-curing at 100° C. for 30 minutes. A dimensionally stable sheet with a density of 1.06 g/cm³, a $T_g$ of 125° C. and a modulus of elasticity of 2210 N/mm² is obtained. The Shore D hardness is 85 and the degree of swelling in toluene is 54%.

EXAMPLE B4

The compound according to Example A1 is mixed with 1% by weight of catalyst B and the mixture is poured into a glass mould. It is irradiated at room temperature in a UV oven according to Example B1 for 2 hours and then polymerized at 80° C. for 30 minutes, at 100° C. for 30 minutes and at 120° C. for 30 minutes. A dimensionally stable sheet with a density of 1.06 g/cm³, a $T_g$ of 125° C. and a modulus of elasticity of 2390 N/mm² is obtained; the maximum stress is 40.4 N/mm², the maximum extension is 2.0% and the impact strength (according to Charpy) is 8.9 kJ/m². The degree of swelling in toluene is 2000%.

EXAMPLES B5 TO B13

The monomer prepared according to Example [lacuna] is mixed with 0.5% by weight of catalyst C and the mixture is poured into a glass mould. Thermal curing is carried out at 60° C. for 1 h, at 80° C. for 1 h, at 100° C. for 1 h and 120° C. for 2 h. After-curing take place at 150° C. for 2 h. The following table shows the results.

| Example | Monomer | $T_g$ | Swelling | $T_g$* | Swelling* |
|---|---|---|---|---|---|
| B5 | A1 | 104 | 34 | 117 | 16 |
| B6 | A2 | 100 | 28 | 120 | 9 |
| B7 | A3 | 1 | 180 | 8 | 172 |
| B8 | A'1 | 122 | 85 | 143 | 76 |
| B9 | A'3 | — | 45 | 15 | 44 |
| B10 | A'4 | 111 | 55 | 118 | 52 |
| B11 | A'5 | 117 | 88 | 124 | 87 |
| B12 | A'6 | 22 | 53 | 29 | 53 |
| B13 | A'7 | 135 | 81 | 156 | 90 |

$T_g$: ° C.;
swelling: in toluene;
*following after-curing

We claim:
1. A composition comprising
   a) at least one compound of formula I

$$(A)_n\text{—B} \qquad (I)$$

in which A is the radical of a strained cycloolefin, B is a direct bond or an n-valent bridging group, and n is an integer from 2 to 8, and
   b) a catalytic amount of a one-component catalyst for metathesis polymerization which can be activated by heat or radiation selected from the group consisting of ruthenium and osmium compounds which contain at least one phosphine group, at least one photolabile ligand, and optionally neutral ligands bonded to the metal atom, a total of 2 to 5 ligands being bonded, and which contain acid anions for charge balancing.
2. A composition according to claim 1, characterized in that the strained olefins are monocyclic or polycyclic fused and/or bridged ring systems which are unsubstituted or substituted and can contain heteroatoms O, S, N or Si in one or more rings and/or fused alicyclic, aromatic or heteroaromatic rings.
3. A composition according to claim 2, characterized in that the individual rings contain 3 to 16 ring members.
4. A composition according to claim 2, characterized in that the rings contain 3 to 12 ring members.
5. A composition according to claim 2, characterized in that the rings contain 3 to 8 ring members.
6. A composition according to claim 1, characterized in that the radical of a strained cycloolefin corresponds to the formula II

(II)

$Q_1$ is a radical having at least one carbon atom which, together with the —CH=CQ₂ group, forms an at least 3-membered alicyclic ring which optionally contains one or more heteroatoms chosen from the group consisting of silicon, phosphorus, oxygen, nitrogen and sulfur; and which is unsubstituted or substituted by halogen, =O, —CN, —NO₂, R₁R₂R₃Si—(O)$_u$—, —COOM, —SO₃M, —PO₃M, —COO(M₁)₁/₂, —SO₃(M₁)₁/₂, —PO₃(M₁)₁/₂, $C_1$-$C_{20}$alkly, $C_1$-$C_{20}$hydroxyalkyl, $C_1$-$C_{20}$haloalkyl, $C_1$-$C_6$cyanoalkyl, $C_3$-$C_8$cycloalkyl, $C_6$-$C_{16}$aryl, $C_7$-$C_{16}$aralkyl, $C_3$-$C_6$heterocycloalkyl, $C_3$-$C_{16}$heteroaryl, $C_4$-$C_{16}$heteroaralkyl or R₄-X-; or in which two adjacent C atoms are substituted by —CO—O—CO— or —CO—NR₅—CO—; or in which an aromatic or heteroaromatic ring and/or further alicyclic rings which is unsubstituted or substituted by halogen, —CN, —NO$_2$, R$_6$R$_7$R$_8$Si—(O)$_u$—, —COOM, —SO$_3$M, —PO$_3$M, —COO(M$_1$)$_{1/2}$, —SO$_3$(M$_1$)$_{1/2}$, —PO$_3$(M$_1$)$_{1/2}$, C$_1$–C$_{20}$alkyl, C$_1$–C$_{20}$haloalkyl, C$_1$–C$_{20}$hydroxyalkyl, C$_1$–C$_6$cyanoalkyl, C$_3$–C$_8$cycloalkyl, C$_6$–C$_{16}$aryl, C$_7$–C$_{16}$aralkyl, C$_3$–C$_6$heterocycloalkyl, C$_3$–C$_6$heteroaryl, C$_4$–C$_{16}$heteroaralkyl or R$_{13}$-X$_1$- are are optionally fused onto adjacent carbon atoms of the alicyclic ring;

X and X$_1$ independently of one another are —O—, —S—, —CO—, —SO—, —SO$_2$—, —O—C(O)—, —C(O)—O—, —C(O)—NR$_5$—, —NR$_{10}$—C(O)—, —SO$_2$—O— or —O—SO$_2$—;

R$_1$, R$_2$ and R$_3$ independently of one another are C$_1$–C$_{12}$alkyl, C$_1$–C$_{12}$perfluoroalkyl, phenyl or benzyl;

R$_4$ and R$_{13}$ independently are C$_1$–C$_{20}$alkyl, C$_1$–C$_{20}$haloalkyl, C$_1$–C$_{20}$hydroxyalkyl, C$_3$–C$_8$cycloalkyl, C$_6$–C$_{16}$aryl or C$_7$–C$_{16}$aralkyl;

R$_5$ and R$_{10}$ independently of one another are hydrogen, C$_1$–C$_{12}$alkyl, phenyl or benzyl, where the alkyl groups in turn are unsubstituted or substituted by C$_1$–C$_{12}$alkoxy or C$_3$–C$_8$cycloalkyl;

R$_6$, R$_7$ and R$_8$ independently of one another are C$_1$–C$_{12}$alkyl, C$_1$–C$_{12}$perfluoroalkyl, phenyl or benzyl;

M is an alkali metal and M$_1$ is an alkaline earth metal; and u is 0 or 1;

where the alicyclic ring formed with Q$_1$ optionally contains further non-aromatic double bonds;

Q$_2$ is hydrogen, C$_1$–C$_{20}$alkyl, C$_1$–C$_{20}$haloalkyl, C$_1$–C$_{12}$alkoxy, halogen, —CN or R$_{11}$-X$_2$;

R$_{11}$ is C$_1$–C$_{20}$alkyl, C$_1$C$_{20}$haloalkyl, C$_1$–C$_{20}$hydroxyalkyl, C$_3$–C$_8$cycloalkyl, C$_6$–C$_{16}$aryl or C$_7$–C$_{16}$aralkyl;

X$_2$ is —C(O)—O— or —C(O)—NR$_{12}$—;

R$_{12}$ is hydrogen, C$_1$–C$_{12}$alkyl, phenyl or benzyl;

where the abovementioned cycloalkyl, heterocycloalkyl, aryl, heteroaryl, aralkyl and heteroaralkyl groups are unsubstituted or substituted by C$_1$–C$_{12}$alkyl, C$_1$–C$_{12}$alkoxy, —NO$_2$, —CN or halogen, and where the heteroatoms of the abovementioned heterocycloalkyl, heteroaryl and heteroaralkyl groups are chosen from the group consisting of —O—, —S—, —NR$_9$— and —N═; and R$_9$ is hydrogen, C$_1$–C$_{12}$alkyl, phenyl or benzyl.

7. A composition according to claim 6, characterized in that, in formula II, Q$_2$ is hydrogen.

8. A composition according to claim 6, characterized in that, in formula II, the alicyclic ring which Q$_1$ forms together with the —CH═CQ$_2$— group contains 3 to 8 ring atoms, the ring being a monocyclic, bicyclic, tricyclic or tetracyclic ring system.

9. A composition according to claim 6, characterized in that the radical of a strained cycloolefin corresponds to the formula II, in which Q$_1$ is a radical with at least one carbon atom which, together with the —CH═CQ$_2$— group, forms a 3- to 20-membered alicyclic ring which optionally contains one or more heteroatoms chosen from the group consisting of silicon, oxygen, nitrogen and sulfur; and which is unsubstituted or substituted by halogen, ═O, —CN, —NO$_2$, R$_1$R$_2$R$_3$Si—(O)$_u$—, —COOM, —SO$_3$M, —PO$_3$M, —COO(M$_1$)$_{1/2}$, —SO$_3$(M$_1$)$_{1/2}$, —PO$_3$(M$_1$)$_{1/2}$, C$_1$–C$_{12}$alkyl, C$_1$–C$_{12}$haloalkyl, C$_1$–C$_{12}$hydroxyalkyl, C$_1$–C$_4$cyanoalkyl, C$_3$–C$_6$cycloalkyl, C$_6$–C$_{12}$aryl, C$_7$–C$_{12}$aralkyl, C$_3$–C$_6$heterocycloalkyl, C$_3$–C$_6$heteroaryl, C$_4$–C$_{12}$heteroaralkyl or R$_4$-X-; or in which two adjacent C atoms in this radical Q$_1$ are substituted by —CO—O—CO— or —CO—NR$_5$—CO—; or in which an a romatic or heteroaromatic ring and/or further alicyclic rings which are unsubstituted or substituted by halogen, —CN, —NO$_2$, R$_6$R$_7$R$_8$Si—, —COOM, —SO$_3$M, —PO$_3$M, —COO(M$_1$)$_{1/2}$, —SO$_3$(M$_1$)$_{1/2}$, —PO$_3$(M$_1$)$_{1/2}$, C$_1$–C$_{12}$alkyl, C$_1$–C$_{12}$haloalkyl, C$_1$–C$_{12}$hydroxyalkyl, C$_1$–C$_4$cyanoaklyl, C$_3$–C$_6$cycloalkyl, C$_6$–C$_{12}$aryl, C$_7$–C$_{12}$aralkyl, C$_3$–C$_6$heterocycloalkyl, C$_3$–C$_{12}$heteroaryl, C$_4$–C$_{12}$heteroaralkyl or R$_{13}$—X$_1$— are optionally fused onto adjacent carbon atoms;

X and X$_1$ independently of one another are —O—, —S—, —CO—, —SO—, —SO$_2$—, —O—C(O)—, —C(O)—O—, —C(O)—NR$_5$—, —NR$_{10}$—C(O)—, —SO$_2$—O— and —O—SO$_2$—; and R$_1$, R$_2$ and R$_3$ independently of one another are C$_1$–C$_6$alkyl, C$_1$–C$_6$perfluoroalkyl, phenyl or benzyl;

M is an alkali metal and M$_1$ is an alkaline earth metal;

R$_4$ and R$_{13}$ independently of one another are C$_1$–C$_{12}$alkyl, C$_1$–C$_{12}$haloalkyl, C$_1$–C$_{12}$hydroxyalkyl, C$_3$–C$_8$cycloalkyl, C$_6$–C$_{12}$aryl or C$_7$–C$_{12}$aralkyl;

R$_5$ and R$_{10}$ independently of one another are hydrogen, C$_1$–C$_6$alkyl, phenyl or benzyl, where the alkyl groups in turn are unsubstituted or substituted by C$_1$–C$_6$alkoxy or C$_3$–C$_6$cycloalkyl;

R$_6$, R$_7$ and R$_8$ independently of one another are C$_1$–C$_6$alkyl, C$_1$–C$_6$perfluoroalkyl, phenyl or benzyl;

u is 0 or 1;

where the alicyclic ring formed with Q$_1$ optionally contains further non-aromatic double bonds;

Q$_2$ is hydrogen, C$_1$–C$_{12}$alkyl, C$_1$–C$_{12}$haloalkyl, C$_1$–C$_6$alkoxy, halogen, —CN or R$_{11}$—X$_2$—;

R$_{11}$ is C$_1$–C$_{12}$alkyl, C$_1$–C$_{12}$haloalkyl, C$_1$–C$_{12}$hydroxyalkyl, C$_3$–C$_6$cycloalkyl, C$_6$–C$_{12}$aryl or C$_7$–C$_{12}$aralkyl;

X$_2$ is —C(O)—O— or —C(O)—NR$_{12}$; and

R$_{12}$ is hydrogen, C$_1$–C$_6$alkyl, phenyl or benzyl;

and where the cycloalkyl, heterocycloalkyl, aryl, heteroaryl, aralkyl and heteroaralkyl groups are unsubstituted or substituted by C$_1$–C$_6$alkyl, C$_1$–C$_6$alkoxy, —NO$_2$, —CN or halogen, and where the heteroatoms of the heterocycloalkyl, heteroaryl and heteroaralkyl groups are chosen from the group consisting of —O—, —S—, —NR$_9$— and —N═; and R$_9$ is hydrogen, C$_1$–C$_6$alkyl, phenyl or benzyl.

10. A composition according to claim 1, characterized in that the radical of a strained cycloolefin corresponds to the formula II, in which Q$_1$ is a radical with at least one carbon atom which, together with the —CH═CQ$_2$— group, forms a 3- to 10-membered alicyclic ring which optionally contains a heteroatom chosen from the group consisting of silicon, oxygen, nitrogen and sulfur and is unsubstituted or substituted by halogen, —CN, —NO$_2$, R$_1$R$_2$R$_3$Si—, —COOM, —SO$_3$M, —PO$_3$M, —COO(M$_1$)$_{1/12}$, —SO$_3$(M$_1$)$_{1/12}$, —PO$_3$(M$_1$)$_{1/12}$, C$_1$–C$_6$alkyl, C$_1$–C$_6$haloalkyl, C$_1$–C$_6$hydroxyalkyl, C$_1$–C$_4$cyanoalkyl, C$_3$–C$_6$cycloalkyl, phenyl, benzyl or R$_4$-X-; or in which an aromatic or heteroaromatic ring which is unsubstituted or substituted by halogen, —CN, —NO$_2$, R$_6$R$_7$R$_8$Si—, —COOM, —SO$_3$M, —PO$_3$M, —COO(M$_1$)$_{1/12}$, —SO$_3$(M$_1$)$_{1/12}$, —PO$_3$(M$_1$)$_{1/12}$, C$_1$–C$_6$alkyl, C$_1$–C$_6$haloalkyl, C$_1$–C$_6$hydroxyalkyl, C$_1$–C$_4$cyanoalkyl, C$_3$–C$_6$cycloalkyl, phenyl, benzyl or R$_{13}$—X$_1$— is optionally fused onto adjacent carbon atoms;

$R_1$, $R_2$ and $R_3$ independently of one another are $C_1-C_4$alkyl, $C_1-C_4$perfluoroalkyl, phenyl or benzyl;

M is an alkali metal and $M_1$ is an alkaline earth metal;

$R_4$ and $R_{13}$ independently of one another are $C_1-C_6$alkyl, $C_1-C_6$haloalkyl, $C_1-C_6$hydroxyalkyl or $C_3-C_6$cycloalkyl;

X and $X_1$ independently of one another are —O—, —S—, —CO—, —SO— or —SO$_2$—;

$R_6$, $R_7$ and $R_8$ independently of one another are $C_1-C_4$alkyl, $C_1-C_4$perfluoroalkyl, phenyl or benzyl; and $Q_2$ is hydrogen.

11. A composition according to claim 1, characterized in that the cycloolefin radical of the formula II is unsubstituted or substituted cyclopropenyl, cyclobutenyl, cyclopentenyl, cycloheptenyl, cyclooctenyl, cyclopentadienyl, cyclohexadienyl, cycloheptadienyl, cyclooctadienyl and norbornenyl or norbornenyl derivatives.

12. A composition according to claim 6, characterized in that the cycloolefin radical of the formula II is a radical of the formula III

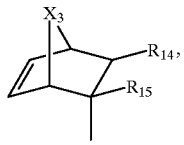
(III)

in which $X_3$ is —CHR$_{16}$—, oxygen or sulfur;

$R_{14}$ and $R_{15}$ independently of one another are hydrogen, —CN, trifluoromethyl, (CH$_3$)$_3$Si—O—, (CH$_3$)$_3$Si— or —COOR$_{17}$; and $R_{16}$ and $R_{17}$ independently of one another are hydrogen, $C_1-C_{12}$-alkyl, phenyl or benzyl; or of the formula IV

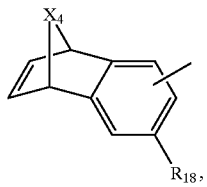
(IV)

in which $X_4$ is —CHR$_{19}$—, oxygen or sulfur;

$R_{19}$ is hydrogen, $C_1-C_{12}$alkyl, phenyl or benzyl; and $R_{18}$ is hydrogen, $C_1-C_6$alkyl or halogen.

13. A composition according to claim 6, characterized in that the cycloolefin radical of the formula II is norbornenyl of the formula

14. A composition according to claim 1, characterized in that, in formula I, n is an integer from 2 to 6.

15. A composition according to claim 1, characterized in that, in formula I, n is an integer from 2 to 4.

16. A composition according to claim 1, characterized in that, in formula I, n is the number 2 or 3.

17. A composition according to claim 1, characterized in that, in formula I, B is an n-valent bridging group.

18. A composition according to claim 1, characterized in that the bridging group corresponds to the formula V $$—X_5—R_{20}—X_6—$$ (V)

in which $X_5$ and $X_6$ independently of one another are a direct bond, —O—, —CH$_2$—O—, —C(O)O—, —O(O)C—, —CH$_2$—O(O)C—, —C(O)—NR$_{21}$—, —R$_{21}$—N—(O)C—, —NH—C(O)—NR$_{21}$—, —O—C(O)—NH—, —CH$_2$—O—C(O)—NH— or —NH—C(O)—O— and $R_{20}$ is $C_2-C_{18}$alkylene, $C_5-C_8$cycloalkylene which is unsubstituted or substituted by $C_1-C_4$alkyl or $C_1-C_4$alkoxy, $C_6-C_{18}$arylene or $C_7-C_{19}$aralkylene which are unsubstituted or substituted by $C_1-C_4$alkyl or $C_1-C_4$alkoxy, or polyoxaalkylene having 2 to 12 oxaalkylene units and 2 to 6 C atoms in the alkylene, and $R_{21}$ is H or $C_1-C_6$alkyl.

19. A composition according to claim 15, characterized in that, in formula V, a) $X_5$ and $X_6$ are a direct bond and $R_{20}$ is $C_2-C_{18}$alkylene, or b) $X_5$ and $X_6$ are —O—, —CH$_2$—O—, —C(O)O—, —O(O)C—, —CH$_2$—O(O)C—, —C(O)—NR$_{21}$—, —O—C(O)—NH— or —CH$_2$—O—C(O)—NH—, and $R_{20}$ is $C_2-C_{12}$alkylene, phenylene, naphthylene or benzylene which are unsubstituted or substituted by $C_1-C_4$alkyl or $C_1-C_4$alkoxy, or —R$_{22}$—(O—R$_{22}$—)$_x$—OR$_{22}$—, in which x is a number from 2 to 4, and $R_{22}$ is —C$_2-C_4$alkylene.

20. A composition according to claim 18, characterized in that they are chosen from the following group of compounds:

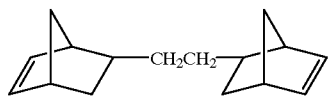
(0)

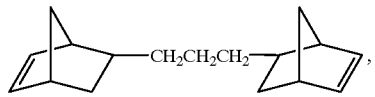
(1)

-continued
(2)
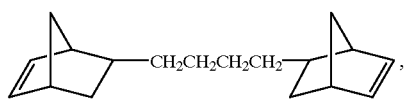
(3)
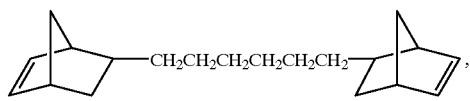
(4)
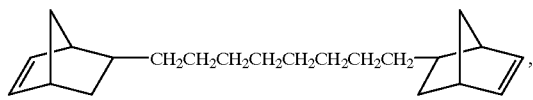
(5)
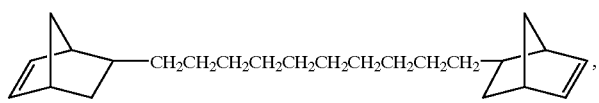
(6)
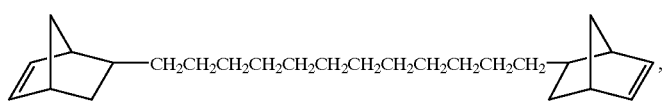
(7)
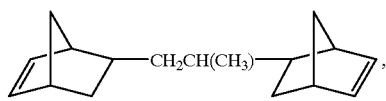
(8)
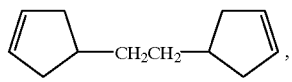
(9)
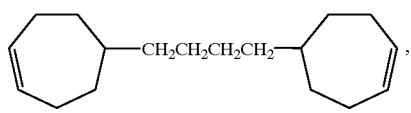
(10)
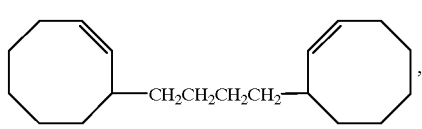
(11)
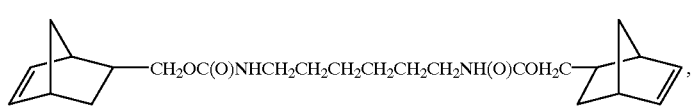
(12)
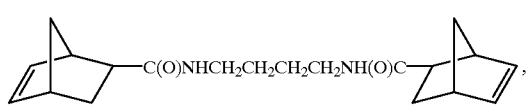
(13)
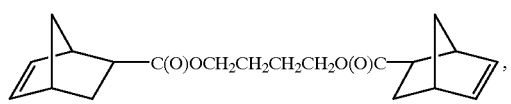

-continued (13a)
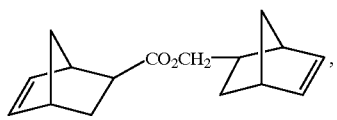

(14)
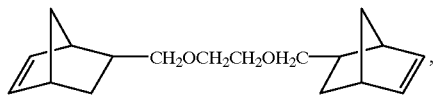

(15)
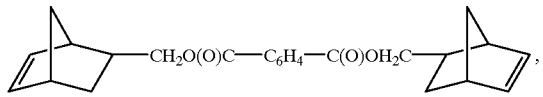

(16)
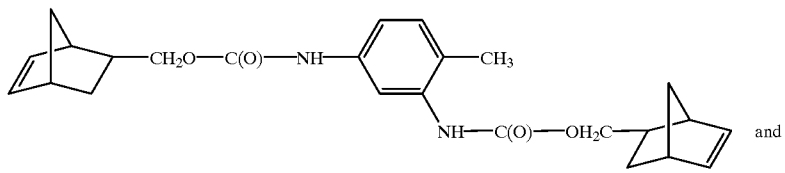
and

(17)
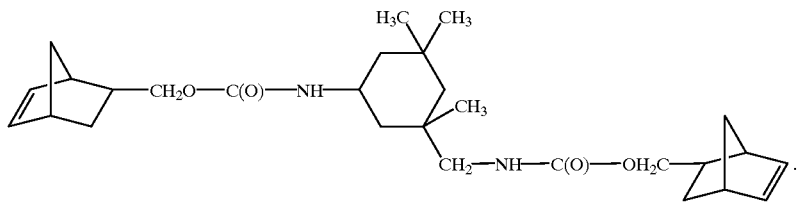

21. A composition according to claim 1, characterized in that the bridging group corresponds to the formula VI

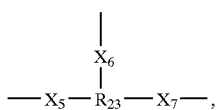
(VI)

in which $X_5$, $X_6$ and $X_7$ are —O—, —CH$_2$—O—, —C(O)O—, —O(O)C—, —CH$_2$—O(O)C—, —C(O)—NR$_{21}$—, —R$_{21}$N—(O)C—, —NH—C(O)—NR$_{21}$—, —O—C(O)—NH—, —CH$_2$—O—C(O)—NH— or —NH—C(O)—O—, and $R_{23}$ is a trivalent aliphatic hydrocarbon radical having 3 to 20 C atoms, a trivalent cycloaliphatic radical which has 3 to 8 ring C atoms and is unsubstituted or substituted by $C_1$–$C_4$alkyl or $C_1$–$C_4$alkoxy, or a trivalent aromatic radical which has 6 to 18 C atoms and is unsubstituted or substituted by $C_1$–$C_4$alkyl or $C_1$–$C_4$alkoxy, a trivalent araliphatic radical which has 7 to 19 C atoms and is unsubstituted or substituted by $C_1$–$C_4$alkyl or $C_1$–$C_4$alkoxy, or a trivalent heteroaromatic radical which has 3 to 13 C atoms and 1 to 3 heteroatoms from the group consisting of —O—, —N— and —S— and is unsubstituted or substituted by $C_1$–$C_4$alkyl or $C_1$–$C_4$alkoxy, and $R_{21}$ is H or $C_1$–$C_6$alkyl.

22. A composition according to claim 21, characterized in that $X_5$, $X_6$ and $X_7$ are —O—, —CH$_2$—O—, —C(O)O—, —O(O)C—, —CH$_2$—O(O)C—, —C(O)—NR$_{21}$—, —CH$_2$—O—C(O)—NH— or —O—C(O)—NH—.

23. A composition according to claim 21, characterized in that the radicals $R_{23}$ are derived from triols; cyanuric acid; triamines; tricarboxylic acids or triisocyanates.

24. A composition according to claim 21, characterized in that they are chosen from the following group of compounds (18)

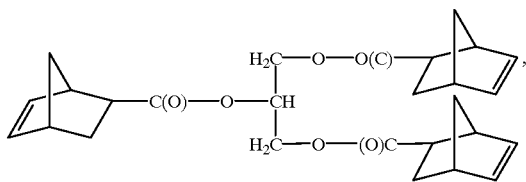

(19)

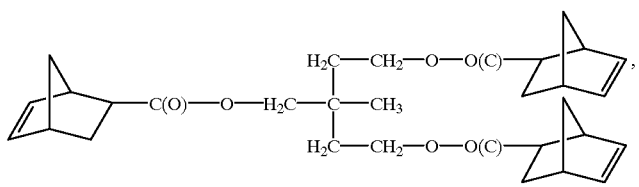

(20)

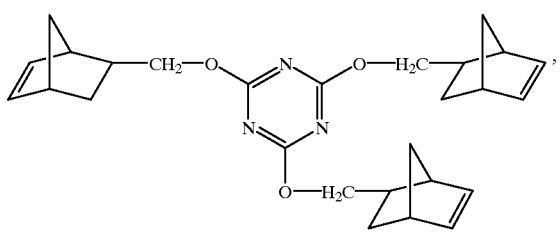

(21)

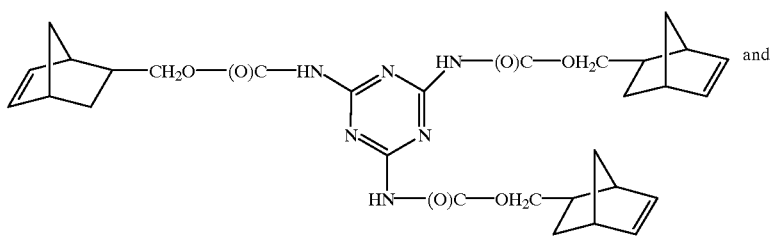 and (22)

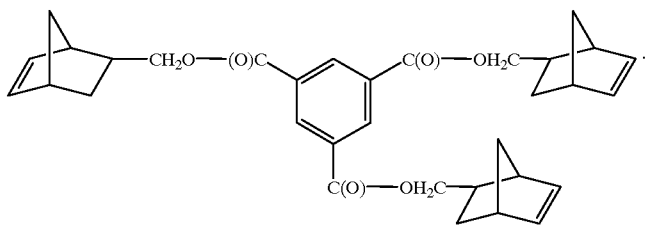

25. A composition according to claim 1, characterized in that the bridging group corresponds to the formula VII

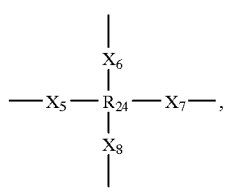
(VII)

in which $X_5$, $X_6$, $X_7$ and $X_8$ are —C(O)O—, —CH$_2$—O(O)C— or —C(O)—NR$_{21}$— and $R_{24}$ is a tetravalent aliphatic hydrocarbon radical having 4 to 20 C atoms, a tetravalent cycloaliphatic radical which has 4 to 8 ring C atoms and is unsubstituted or substituted by C$_1$–C$_4$alkyl or C$_1$–C$_4$alkoxy, or a tetravalent aromatic radical which has 6 to 18 C atoms and is unsubstituted or substituted by C$_1$–C$_4$alkyl or C$_1$–C$_4$alkoxy, a tetravalent araliphatic radical which has 7 to 19 C atoms and is unsubstituted or substituted by C$_1$–C$_4$alkyl or C$_1$–C$_4$alkoxy, or a tetravalent heteroaromatic radical which has 3 to 13 C atoms and 1 to three heteroatoms, from the group consisting of —O—, —N— and —S— and is unsubstituted or substituted by C$_1$–C$_4$alkyl or C$_1$–C$_4$alkoxy, and R$_{21}$ is H or C$_1$–C$_6$alkyl.

26. A composition according to claim 25, characterized in that the radicals $R_{24}$ are derived from pentaerythritol, pyromellitic acid and 3,4,3',4'-biphenyltetracarboxylic acid.

27. A composition according to claim 25, characterized in that they are

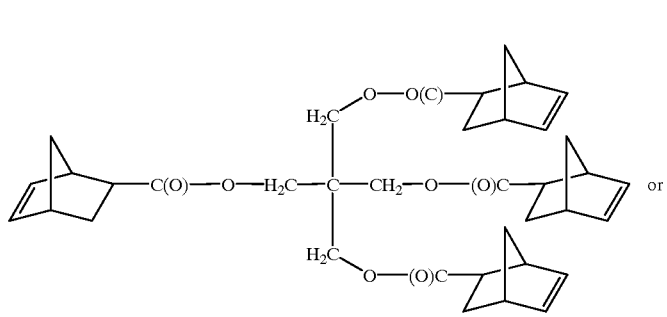
(23)

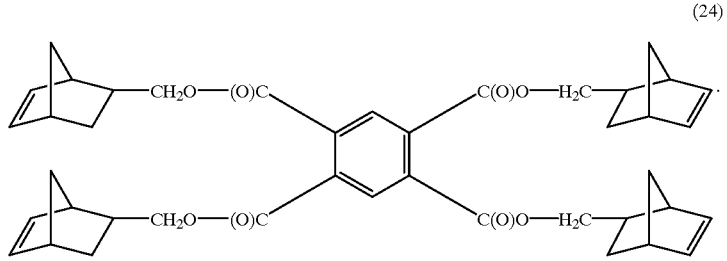
(24)

28. A composition according to claim 1, characterized in that the compounds of the formula I contain only carbon and hydrogen atoms.

29. Composition according to claim 1, characterized in that the phosphine ligands correspond to the formulae XXIII or XXIIIa.

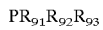 (XXIII),

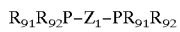 (XXIIIa)

in which $R_{91}$, $R_{92}$ and $R_{93}$ independently of one another are H, $C_1$–$C_{20}$alkyl, $C_4$–$C_{12}$cycloalkyl which is unsubstituted or substituted by $C_1$–$C_6$alkyl, $C_1$–$C_6$haloalkyl or $C_1$–$C_6$alkoxy, or $C_6$–$C_{16}$aryl which is unsubstituted or substituted by $C_1$–$C_6$alkyl, $C_1$–$C_6$haloalkyl or $C_1$–$C_6$alkoxy, or $C_7$–$C_{16}$aralkyl which is unsubstituted or substituted by $C_1$–$C_6$alkyl, $C_1$–$C_6$haloalkyl or $C_1$–$C_6$alkoxy; the radicals $R_{91}$ and $R_{92}$ together are tetra- or pentamethylene, which is unsubstituted or substituted by $C_1$–$C_6$alkyl, $C_1$–$C_6$haloalkyl or $C_1$–$C_6$alkoxy, or tetra- or pentamethylene, which is unsubstituted or substituted by $C_1$–$C_6$alkyl, $C_1$–$C_6$haloalkyl or $C_1$–$C_6$alkoxy and fused with 1 or 2 1,2-phenylene, and $R_{93}$ has the meaning given above; and $Z_1$ is linear or branched $C_2$–$C_{12}$alkylene which is unsubstituted or substituted by $C_1$–$C_4$alkoxy, 1,2-or 1,3-cycloalkylene which has 4 to 8 C atoms and is unsubstituted or substituted by $C_1$–$C_4$alkyl or $C_1$–$C_4$alkoxy, or 1,2 or 1,3-heterocycloalkylene which has 5 or 6 ring members and one heteroatom from the group consisting of O or N and is unsubstituted or substituted by $C_1$–$C_4$alkyl or $C_1$–$C_4$alkoxy.

30. Composition according to claim 1, characterized in that the one-component catalyst is a divalent-cationic ruthenium or osmium compound with a metal atom to which are bonded, 1 to 3 tertiary phosphine ligands with, in the case of the ruthenium compounds, sterically exacting substituents, optionally non-photolabile neutral ligands and anions for charge balancing, with the proviso that, in ruthenium (trisphenylphosphine) dihalides or hydride-halides, the phenyl groups are substituted by $C_1$–$C_{18}$alkyl, $C_1$–$C_{18}$haloalkyl or $C_1$–$C_{18}$alkoxy.

31. Composition according to claim 30, characterized in that the phosphine ligands correspond to the formulae XXIII or XXIIIa $PR_{91}R_{92}R_{93}$ (XXIII), $R_{91}R_{92}P-Z_1-PR_{91}R_{92}$ (XXIIIa), in which $R_{91}$, $R_{92}$ and $R_{93}$ independently of one another are H, $C_1$–$C_{20}$alkyl, $C_4$–$C_{12}$cycloalkyl which is unsubstituted or substituted by $C_1$–$C_6$alkyl, $C_1$–$C_6$haloalkyl or $C_1$–$C_6$alkoxy, or $C_6$–$C_{16}$aryl which is unsubstituted or substituted by $C_1$–$C_6$alkyl, $C_1$–$C_6$haloalkyl or $C_1$–$C_6$alkoxy, or $C_7$–$C_{16}$aralkyl which is unsubstituted or substituted by $C_1$–$C_6$alkyl, $C_1$–$C_6$haloalkyl or $C_1$–$C_6$alkoxy; the radicals $R_{91}$ and $R_{92}$ together are tetra- or pentamethylene, which is unsubstituted or substituted by $C_1$–$C_6$alkyl, $C_1$–$C_6$haloalkyl or $C_1$–$C_6$alkoxy, or tetra- or pentamethylene, which is unsubstituted or substituted by $C_1$–$C_6$alkyl, $C_1$–$C_6$haloalkyl or $C_1$–$C_6$alkoxy and fused with 1 or 2 1,2-phenylene, and $R_{93}$ has the meaning given above; and $Z_1$ is linear or branched $C_2$–$C_{12}$alkylene which is unsubstituted or substi tuted by $C_1$–$C_4$alkoxy, 1,2- or 1,3-cycloalkylene which has 4 to 8 C atoms and is unsubstituted or substituted by $C_1$–$C_4$alkyl or $C_1$–$C_4$alkoxy, or 1,2 or 1,3-heterocycloalkylene which has 5 or 6 ring members and one heteroatom from the group consisting of O or N and is unsubstituted or substituted by $C_1$–$C_4$alkyl or $C_1$–$C_4$alkoxy.

32. Composition according to claim 1, characterized in that the one-component catalyst is present in an amount of from 0.001 to 20 mol %, based on the amount of the monomer.

* * * * *